US007741536B2

(12) United States Patent
Daniell

(10) Patent No.: US 7,741,536 B2
(45) Date of Patent: Jun. 22, 2010

(54) EXPRESSION OF HUMAN SERUM ALBUMIN IN PLASTIDS

(75) Inventor: Henry Daniell, Winter Park, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 121 days.

(21) Appl. No.: 11/406,522

(22) Filed: Apr. 18, 2006

(65) Prior Publication Data

US 2006/0253935 A1 Nov. 9, 2006

Related U.S. Application Data

(63) Continuation-in-part of application No. 11/230,299, filed on Sep. 19, 2005, now abandoned, which is a continuation of application No. 09/807,742, filed on Apr. 18, 2001, now abandoned, which is a continuation-in-part of application No. 09/079,640, filed on May 15, 1998, now Pat. No. 7,129,391.

(60) Provisional application No. 60/185,987, filed on Mar. 1, 2000, provisional application No. 60/263,473, filed on Jan. 23, 2001, provisional application No. 60/263,668, filed on Jan. 23, 2001, provisional application No. 60/055,314, filed on Aug. 7, 1997, provisional application No. 60/079,042, filed on Mar. 23, 1998.

(51) Int. Cl.
*C12N 15/82* (2006.01)
(52) U.S. Cl. ............... 800/298; 435/320.1; 426/655
(58) Field of Classification Search ............. None
See application file for complete search history.

(56) References Cited

U.S. PATENT DOCUMENTS

| 4,616,078 | A |   | 10/1986 | DiMarchi |
| 4,956,282 | A |   | 9/1990 | Goodman et al. |
| 4,963,665 | A |   | 10/1990 | Rotwein et al. |
| 5,545,817 | A | * | 8/1996 | McBride et al. ......... 800/287 |
| 5,650,307 | A | * | 7/1997 | Sijmons et al. ......... 435/69.6 |
| 5,877,402 | A | * | 3/1999 | Maliga et al. .......... 800/298 |
| 6,004,782 | A |   | 12/1999 | Daniell et al. |
| 7,294,506 | B2 | * | 11/2007 | Daniell et al. ......... 435/320.1 |
| 2002/0174453 | A1 | * | 11/2002 | Daniell et al. ........ 800/288 |

FOREIGN PATENT DOCUMENTS

| WO | WO 99/10513 | 3/1999 |
| WO | WO 99/18225 | 4/1999 |
| WO | WO 00/03012 | 1/2000 |

OTHER PUBLICATIONS

Gadanii et al, Agro Food Industry Hi-Tech, (1995) vol. 6, No. 2, pp. 3-6.*
Sijmons, P. C. et al. "Production of Correctly Processed Human Serum Albumin in Transgenic Plants", *Biotechnology*, Mar. 1990, pp. 217-221, vol. 8.
Boston, R. S. et al. "Molecular Chaperones and Protein Folding in Plants", *Plant Molecular Biology*, 1996, pp. 191-222, vol. 32.
Crickmore, N. et al. "Revision of the Nomenclature for the *Bacillus thuringiensis* Pesticidal Crystal Proteins", *Microbiology and Molecular Biology Reviews*, Sep. 1998, pp. 807-813, vol. 62.
Kota, M. et al. "Overexpression of *Bacillus thuringiensis* (Bt) Cry2Aa2 Protein in Chloroplast Confers Resistance to Plants Against Susceptible and Bt-resistant Insects" *Proc. Natl. Acad. Sci. USA*, Mar. 1999, pp. 1840-1845, vol. 96.
Heifetz, P. B. "Genetic Engineering of the Chloroplast", *Biochimie*, 2000, pp. 655-666, vol. 82.
Kanno, A. et al. "A Transcription Map of the Chloroplast Genome from Rice (*Oryza sativa*)", *Curr Genet.*, Feb. 1993, pp. 166-174, vol. 23, No. 2.
McBride, K.E. et al. "Amplification of a Chimeric *Bacillus* Gene in Chloroplasts Leads to an Extraordinary Level of an insecticidal Protein in Tobacco", *Biotechnology*, Apr. 1995, pp. 362-365, vol. 13.
Zoubenko, O. V. et al. "Efficient Targeting of Foreign Genes into the Tobacco Plastid Genome", *Nucleic Acid Research*, 1994, pp. 3819-1824, vol. 22, No. 19.
Daniell, H. et al. "Containment of Herbicide Resistance Through Genetic Engineering of the Chloroplast Genome", *Nature Biotechnology*, 1998, pp. 345-348, vol. 16.
Lu, Z. et al. "Characterization of Republication Origins Flanking the 23S rRNA Gene in Tobacco Chloroplast DNA", *Plant Mol. Biol.*, 1996, pp. 693-706, vol. 32.
Staub, J.M. et al, "Long regions of homologous DNA are incorporated into the tobacco plastid genome by transformation.Plant Cell", Jan. 1992, pp. 39-45, vol. 4, No. 1.
Datta, R. et al., "Transformation of the Tobacco Chloroplast Genome with the aroA Gene to Confer Glyphosate Tolerance," *Supplement to Plant Physiology*, Jun. 1996, p. 168, vol. 111, No. 2.

* cited by examiner

*Primary Examiner*—Anne Kubelik
(74) *Attorney, Agent, or Firm*—Timothy H. Van Dyke; Beusse Wolter Sanks Mora & Maire

(57) ABSTRACT

Humans Serum Albumin (HSA) or an HSA fusion protein is expressed in plant plastids. A plastid transformation vector is made which contains an expression cassette that contains regulatory sequences, the coding region for HSA or an HSA fusion protein and a selectable marker coding sequence. The vector is used to transform a plant where the plant expresses the HSA or HSA fusion protein. HSA is isolated and purified from the plant. A preferred plant is tobacco.

8 Claims, 20 Drawing Sheets

A. Copper Stained

B. Coomassie R-250 Stained

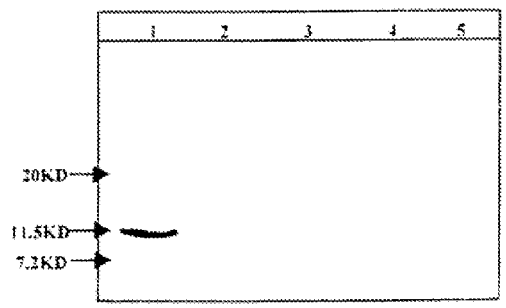
Western Blot analysis of CTB expression in *E.coli* (15% PAGE):
Lane 1: Purified bacterial CTB (0.5μg) ; 2 & 4: Transformed E.coli culture-24 h and 48 h resply. ; 3 & 5 : Untransformed E.coli culture- 24 h and 48 h resply.
FIG 3A
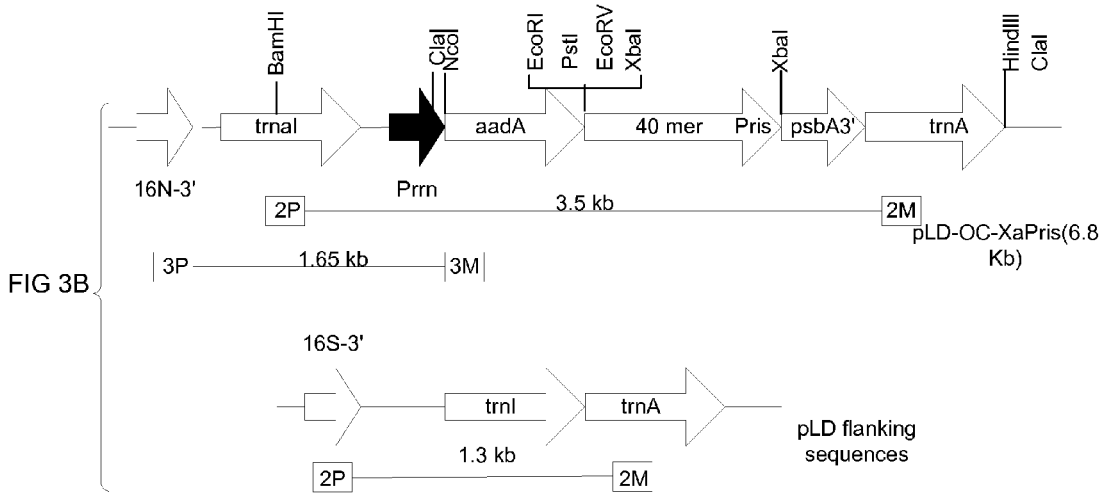
FIG 3B
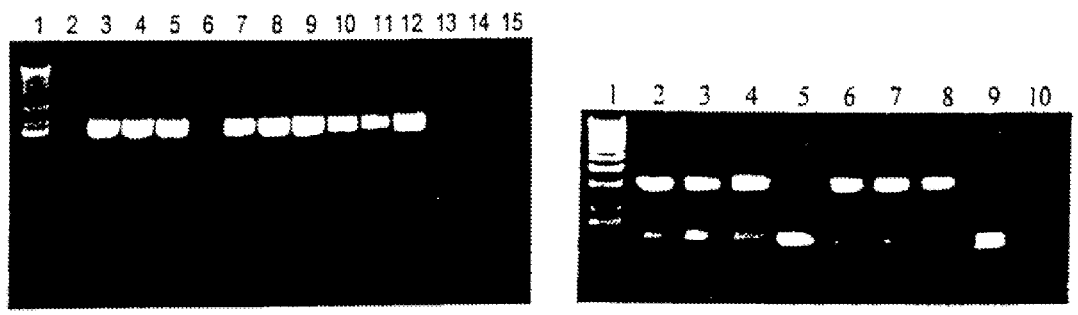
FIG 3C                    FIG 3D

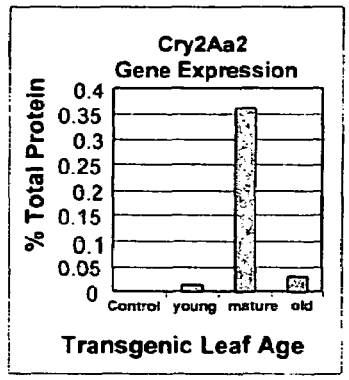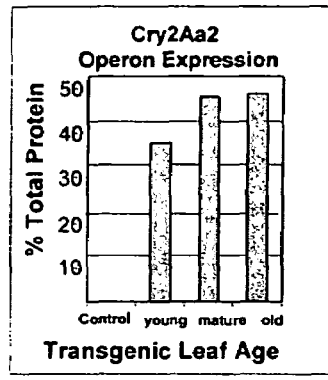
FIG 4A            FIG 4B
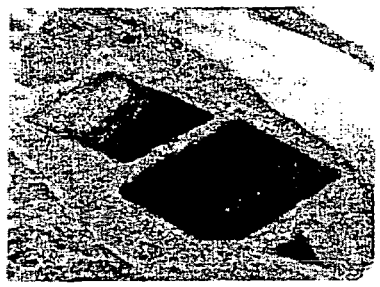
FIG 5
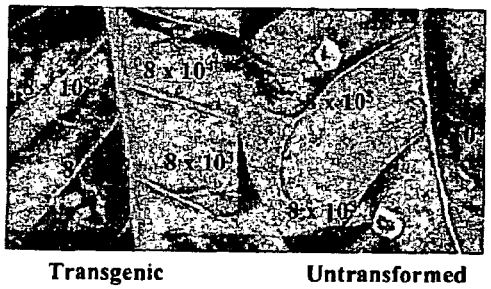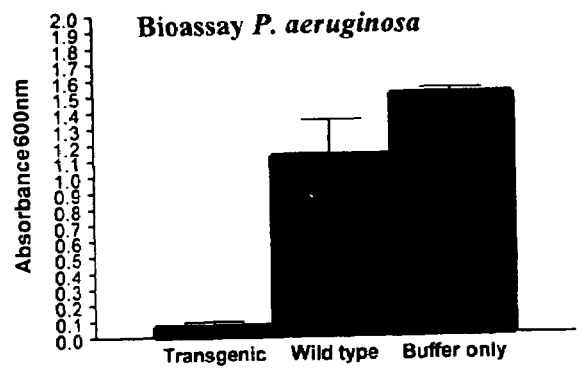
FIG 6            FIG 7

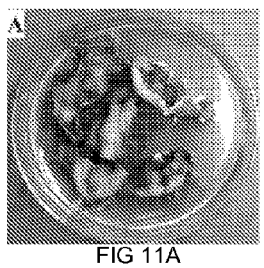
FIG 11A
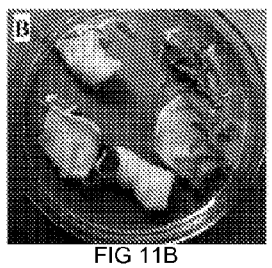
FIG 11B
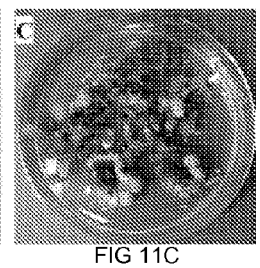
FIG 11C
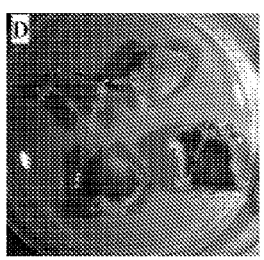
FIG 11D
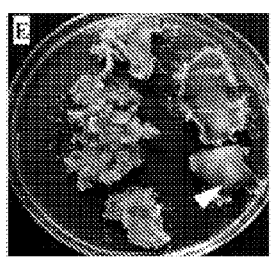
FIG 11E
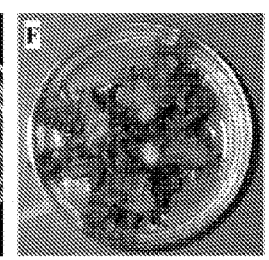
FIG 11F
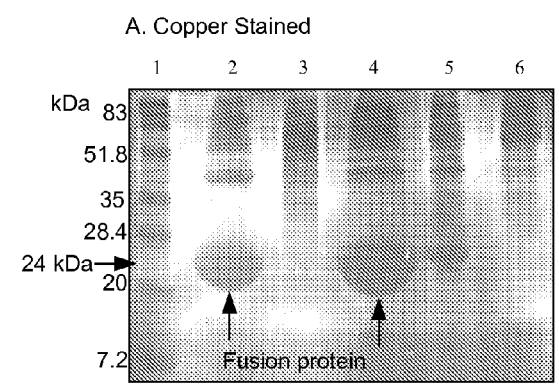
FIG. 12A — A. Copper Stained
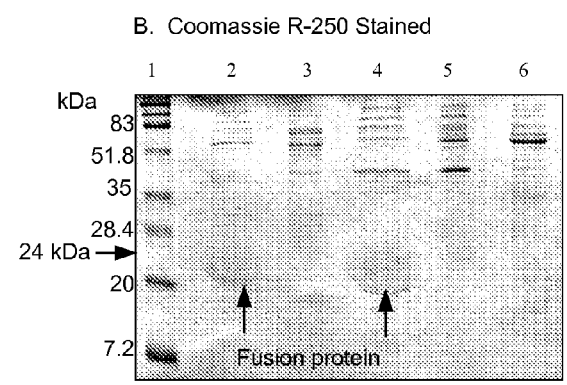
FIG. 12B — B. Coomassie R-250 Stained
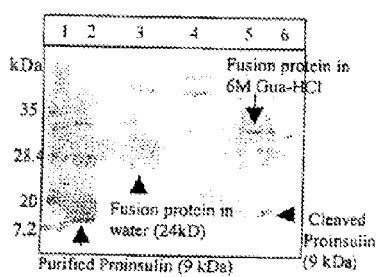
FIG. 13A
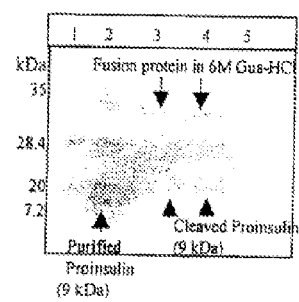
FIG. 13B
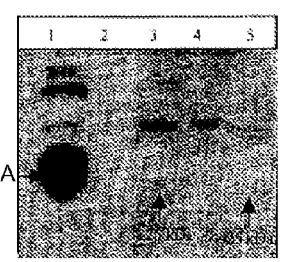
FIG. 13C A
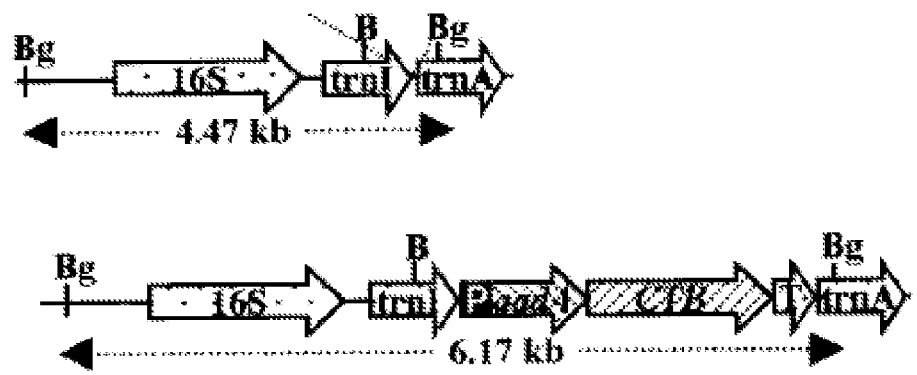
B
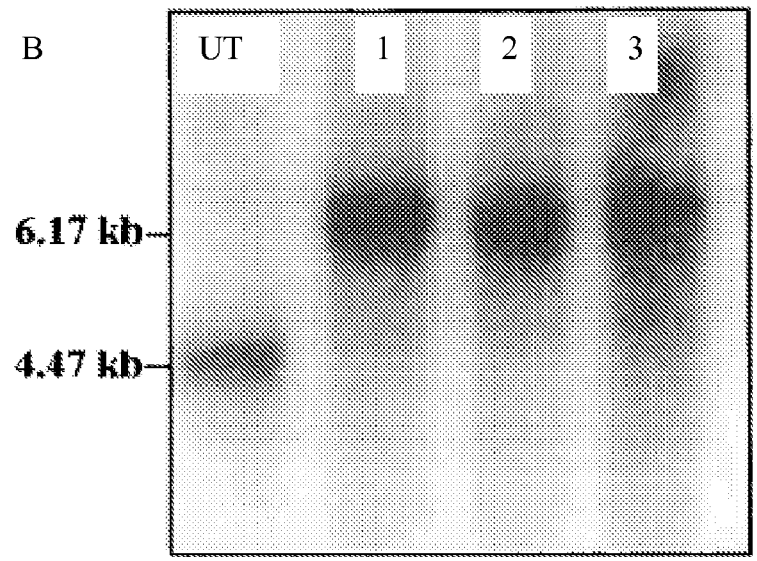
FIG. 23
C
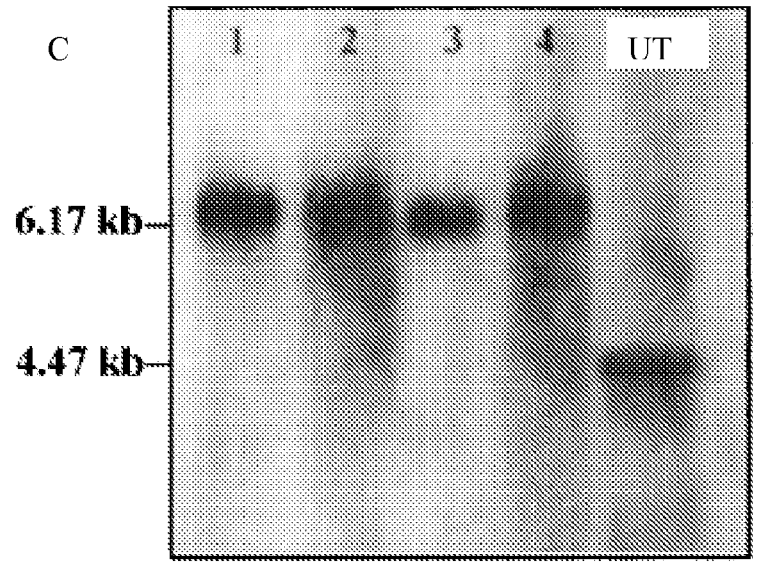

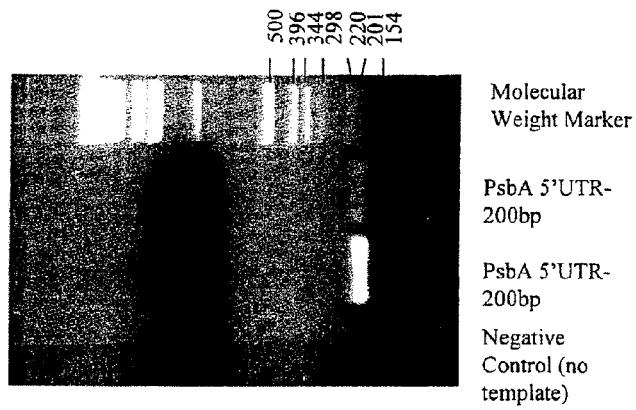

FIG 25

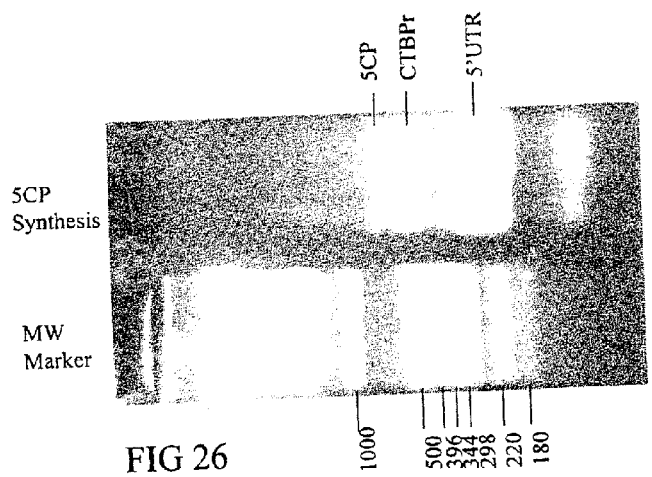

```
      ttgtgaaccaacacctgtgcggctcacacctggtggaagctctctacctagtgtgcggg
      | || ||||||||| | || || || ||||| || |||||| | ||| |||| || ||
      tcgtaaaccaacacttatgtggttctcacctagtagaagctttatacttagtatgtggt aacgaggcttcttctacacacccaagacccgccgggaggcagaggacctgcaggtgggg
      |||| || ||||||||||| || || || || || || || || || || | || || ||
      aacgtggtttcttctacactcctaaaactcgtcgtgaagctgaagatttacaagtaggt aggtggagctgggcggggggcctggtgcaggcagcctgcagcccttggccctggagggg
      | || || | || || || |||||||| ||        | || || || || | || ||
      aagtagaattaggtggtggtcctggtgctggttctttacaacctttagctttagaaggt ccctgcagaagcgtggcattgtggaacaatgctgtaccagcatctgctccctctaccag
      |  | || || ||||| ||||| |||||||||| ||||  ||| || || | |||||
      ctttacaaaaacgtggtattgtagaacaatgttgtacttctatttgttctttataccaa tggagaactactgcaacta     Native Human Proinsulin    SEQ ID NO. 16
      | || ||||||||| |||||
      tagaaaactactgtaacta     Chloroplast Modified Proinsulin  SEQ ID NO. 17
```

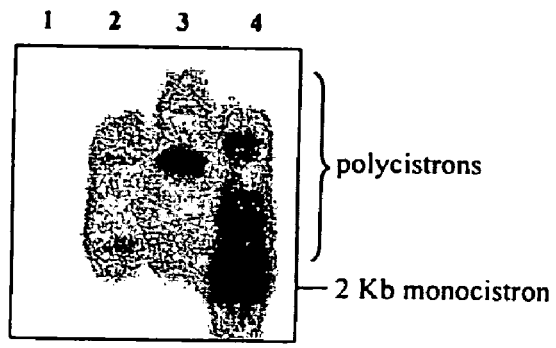

FIG 32

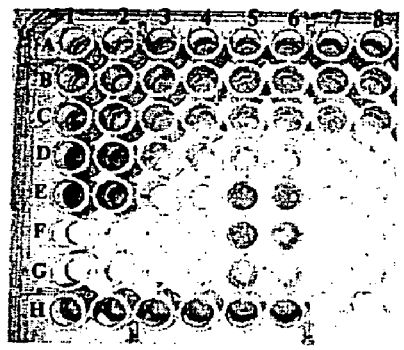

FIG 33

FIG 34A
```
ggaccggagacgctctgcggggctgagctggtggatgctcttcagttcgtg
tgtggagacaggggcttttatttcaacaagcccacagggtatggctccagc
agtcggagggcgcctcagacaggcatcgtggatgagtgctgcttccggagc
tgtgatctaaggaggctggagatgtattgcgcacccctcaagcctgccaag
tcagct
```

FIG 34B
```
ggtcctgaaactttatgtggtgctgaattagtagatgctttacaattcgta
tgtggtgatcgtggtttctatttcaacaaacctactggttacggttcttct
tctcgtcgtgctcctcaaactggtattgtagatgaatgttgtttccgttct
tgtgatttacgtcgtttagaaatgtactgtgctcctttaaaacctgctaaa
tctgct
```

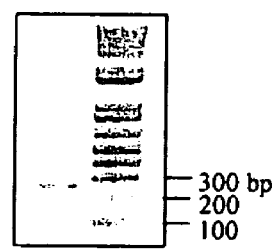

FIG 34C

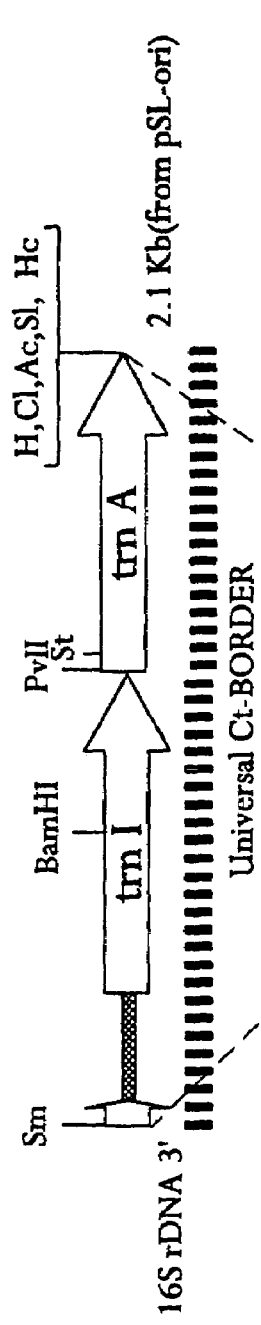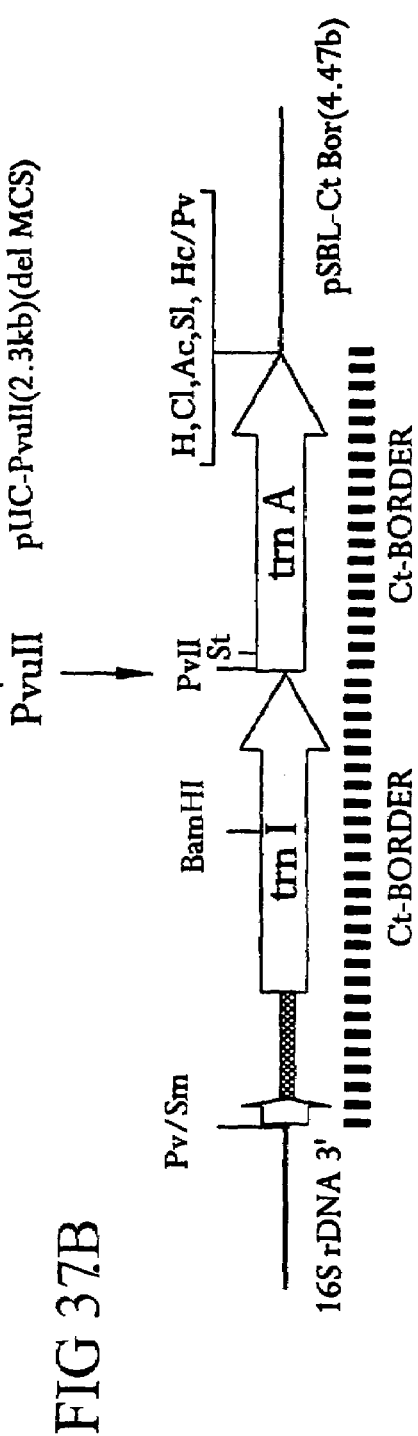
FIG 37A
FIG 37B
FIG 37C

SEQUENCE LISTING

```
<160> NUMBER OF SEQ ID NOS: 26

<210> SEQ ID NO 1
<211> LENGTH: 1250
<212> TYPE: PRT
<213> ORGANISM: Artificial sequence
<220> FEATURE:
<223> OTHER INFORMATION: Protein-based polymer (PBP) made from synthetic
      genes.

<400> SEQUENCE: 1

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
```

-continued

```
                85                  90                  95
Val Gly Val Pro Gly Val Gly Val Pro Gly Val Gly Val Pro Gly Val
            100                 105                 110
Gly Val Pro Gly Val Gly Val Pro Gly Val Gly Val Pro Gly Val Gly
            115                 120                 125
Val Pro Gly Val Gly Val Pro Gly Val Gly Val Pro Gly Val Gly Val
            130                 135                 140
Pro Gly Val Gly Val Pro Gly Val Gly Val Pro Gly Val Gly Val Pro
145                 150                 155                 160
Gly Val Gly Val Pro Gly Val Gly Val Pro Gly Val Gly Val Pro Gly
            165                 170                 175
Val Gly Val Pro Gly Val Gly Val Pro Gly Val Gly Val Pro Gly Val
            180                 185                 190
Gly Val Pro Gly Val Gly Val Pro Gly Val Gly Val Pro Gly Val Gly
            195                 200                 205
Val Pro Gly Val Gly Val Pro Gly Val Gly Val Pro Gly Val Gly Val
            210                 215                 220
Pro Gly Val Gly Val Pro Gly Val Gly Val Pro Gly Val Gly Val Pro
225                 230                 235                 240
Gly Val Gly Val Pro Gly Val Gly Val Pro Gly Val Gly Val Pro Gly
            245                 250                 255
Val Gly Val Pro Gly Val Gly Val Pro Gly Val Gly Val Pro Gly Val
            260                 265                 270
Gly Val Pro Gly Val Gly Val Pro Gly Val Gly Val Pro Gly Val Gly
            275                 280                 285
Val Pro Gly Val Gly Val Pro Gly Val Gly Val Pro Gly Val Gly Val
            290                 295                 300
Pro Gly Val Gly Val Pro Gly Val Gly Val Pro Gly Val Gly Val Pro
305                 310                 315                 320
Gly Val Gly Val Pro Gly Val Gly Val Pro Gly Val Gly Val Pro Gly
            325                 330                 335
Val Gly Val Pro Gly Val Gly Val Pro Gly Val Gly Val Pro Gly Val
            340                 345                 350
Gly Val Pro Gly Val Gly Val Pro Gly Val Gly Val Pro Gly Val Gly
            355                 360                 365
Val Pro Gly Val Gly Val Pro Gly Val Gly Val Pro Gly Val Gly Val
            370                 375                 380
Pro Gly Val Gly Val Pro Gly Val Gly Val Pro Gly Val Gly Val Pro
385                 390                 395                 400
Gly Val Gly Val Pro Gly Val Gly Val Pro Gly Val Gly Val Pro Gly
            405                 410                 415
Val Gly Val Pro Gly Val Gly Val Pro Gly Val Gly Val Pro Gly Val
            420                 425                 430
Gly Val Pro Gly Val Gly Val Pro Gly Val Gly Val Pro Gly Val Gly
            435                 440                 445
Val Pro Gly Val Gly Val Pro Gly Val Gly Val Pro Gly Val Gly Val
            450                 455                 460
Pro Gly Val Gly Val Pro Gly Val Gly Val Pro Gly Val Gly Val Pro
465                 470                 475                 480
Gly Val Gly Val Pro Gly Val Gly Val Pro Gly Val Gly Val Pro Gly
            485                 490                 495
Val Gly Val Pro Gly Val Gly Val Pro Gly Val Gly Val Pro Gly Val
            500                 505                 510
```

-continued

Gly Val Pro Gly Val Gly Val Pro Gly Val Gly Val Pro Gly Val Gly
            515                 520                 525

Val Pro Gly Val Gly Val Pro Gly Val Gly Val Pro Gly Val Gly Val
            530                 535                 540

Pro Gly Val Gly Val Pro Gly Val Gly Val Pro Gly Val Gly Val Pro
545                 550                 555                 560

Gly Val Gly Val Pro Gly Val Gly Val Pro Gly Val Gly Val Pro Gly
            565                 570                 575

Val Gly Val Pro Gly Val Gly Val Pro Gly Val Gly Val Pro Gly Val
            580                 585                 590

Gly Val Pro Gly Val Gly Val Pro Gly Val Gly Val Pro Gly Val Gly
            595                 600                 605

Val Pro Gly Val Gly Val Pro Gly Val Gly Val Pro Gly Val Gly Val
            610                 615                 620

Pro Gly Val Gly Val Pro Gly Val Gly Val Pro Gly Val Gly Val Pro
625                 630                 635                 640

Gly Val Gly Val Pro Gly Val Gly Val Pro Gly Val Gly Val Pro Gly
            645                 650                 655

Val Gly Val Pro Gly Val Gly Val Pro Gly Val Gly Val Pro Gly Val
            660                 665                 670

Gly Val Pro Gly Val Gly Val Pro Gly Val Gly Val Pro Gly Val Gly
            675                 680                 685

Val Pro Gly Val Gly Val Pro Gly Val Gly Val Pro Gly Val Gly Val
            690                 695                 700

Pro Gly Val Gly Val Pro Gly Val Gly Val Pro Gly Val Gly Val Pro
705                 710                 715                 720

Gly Val Gly Val Pro Gly Val Gly Val Pro Gly Val Gly Val Pro Gly
            725                 730                 735

Val Gly Val Pro Gly Val Gly Val Pro Gly Val Gly Val Pro Gly Val
            740                 745                 750

Gly Val Pro Gly Val Gly Val Pro Gly Val Gly Val Pro Gly Val Gly
            755                 760                 765

Val Pro Gly Val Gly Val Pro Gly Val Gly Val Pro Gly Val Gly Val
            770                 775                 780

Pro Gly Val Gly Val Pro Gly Val Gly Val Pro Gly Val Gly Val Pro
785                 790                 795                 800

Gly Val Gly Val Pro Gly Val Gly Val Pro Gly Val Gly Val Pro Gly
            805                 810                 815

Val Gly Val Pro Gly Val Gly Val Pro Gly Val Gly Val Pro Gly Val
            820                 825                 830

Gly Val Pro Gly Val Gly Val Pro Gly Val Gly Val Pro Gly Val Gly
            835                 840                 845

Val Pro Gly Val Gly Val Pro Gly Val Gly Val Pro Gly Val Gly Val
            850                 855                 860

Pro Gly Val Gly Val Pro Gly Val Gly Val Pro Gly Val Gly Val Pro
865                 870                 875                 880

Gly Val Gly Val Pro Gly Val Gly Val Pro Gly Val Gly Val Pro Gly
            885                 890                 895

Val Gly Val Pro Gly Val Gly Val Pro Gly Val Gly Val Pro Gly Val
            900                 905                 910

Gly Val Pro Gly Val Gly Val Pro Gly Val Gly Val Pro Gly Val Gly
            915                 920                 925

```
Val Pro Gly Val Gly Val Pro Gly Val Gly Val Pro Gly Val Gly Val
    930                 935                 940
Pro Gly Val Gly Val Pro Gly Val Gly Val Pro Gly Val Gly Val Pro
945                 950                 955                 960
Gly Val Gly Val Pro Gly Val Gly Val Pro Gly Val Gly Val Pro Gly
                965                 970                 975
Val Gly Val Pro Gly Val Gly Val Pro Gly Val Gly Val Pro Gly Val
            980                 985                 990
Gly Val Pro Gly Val Gly Val Pro  Gly Val Gly Val Pro  Gly Val Gly
        995                 1000                1005
Val Pro  Gly Val Gly Val Pro  Gly Val Gly Val Pro  Gly Val Gly
    1010                1015                1020
Val Pro  Gly Val Gly Val Pro  Gly Val Gly Val Pro  Gly Val Gly
    1025                1030                1035
Val Pro  Gly Val Gly Val Pro  Gly Val Gly Val Pro  Gly Val Gly
    1040                1045                1050
Val Pro  Gly Val Gly Val Pro  Gly Val Gly Val Pro  Gly Val Gly
    1055                1060                1065
Val Pro  Gly Val Gly Val Pro  Gly Val Gly Val Pro  Gly Val Gly
    1070                1075                1080
Val Pro  Gly Val Gly Val Pro  Gly Val Gly Val Pro  Gly Val Gly
    1085                1090                1095
Val Pro  Gly Val Gly Val Pro  Gly Val Gly Val Pro  Gly Val Gly
    1100                1105                1110
Val Pro  Gly Val Gly Val Pro  Gly Val Gly Val Pro  Gly Val Gly
    1115                1120                1125
Val Pro  Gly Val Gly Val Pro  Gly Val Gly Val Pro  Gly Val Gly
    1130                1135                1140
Val Pro  Gly Val Gly Val Pro  Gly Val Gly Val Pro  Gly Val Gly
    1145                1150                1155
Val Pro  Gly Val Gly Val Pro  Gly Val Gly Val Pro  Gly Val Gly
    1160                1165                1170
Val Pro  Gly Val Gly Val Pro  Gly Val Gly Val Pro  Gly Val Gly
    1175                1180                1185
Val Pro  Gly Val Gly Val Pro  Gly Val Gly Val Pro  Gly Val Gly
    1190                1195                1200
Val Pro  Gly Val Gly Val Pro  Gly Val Gly Val Pro  Gly Val Gly
    1205                1210                1215
Val Pro  Gly Val Gly Val Pro  Gly Val Gly Val Pro  Gly Val Gly
    1220                1225                1230
Val Pro  Gly Val Gly Val Pro  Gly Val Gly Val Pro  Gly Val Gly
    1235                1240                1245
Val Pro
    1250

<210> SEQ ID NO 2
<211> LENGTH: 6
<212> TYPE: PRT
<213> ORGANISM: Artificial Sequence
<220> FEATURE:
<223> OTHER INFORMATION: Illustrative endoplasmic reticulum retention
      signal

<400> SEQUENCE: 2

Ser Glu Lys Asp Glu Leu
1               5
```

```
<210> SEQ ID NO 3
<211> LENGTH: 4
<212> TYPE: PRT
<213> ORGANISM: Artificial sequence
<220> FEATURE:
<223> OTHER INFORMATION: Illustrative peptide

<400> SEQUENCE: 3

Gly Pro Gly Pro
1

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
ccgtcgacgt agagaagtcc gtatt                                           25

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
gcccatggta aaatcttggt ttattta                                         27

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
cctttaaaaa gccttccatt ttctatttt                                       28

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
gccatggtaa aatcttggtt tatta                                           25

<210> SEQ ID NO 8

<400> SEQUENCE: 8

000

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9
```

```
Ala Val Gly Val Pro
1               5

<210> SEQ ID NO 10
<211> LENGTH: 7
<212> TYPE: PRT
<213> ORGANISM: Artificial Sequence
<220> FEATURE:
<223> OTHER INFORMATION: Illustrative peptide (cleavage site recognized
      for TEV protease)

<400> SEQUENCE: 10

Glu Asn Leu Tyr Phe Gln Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Cleavage site recognized by Thrombin

<400> SEQUENCE: 11

Leu Val Pro Arg Gly Ser
1               5

<210> SEQ ID NO 12
<211> LENGTH: 6
<212> TYPE: PRT
<213> ORGANISM: Artificial Sequence
<220> FEATURE:
<223> OTHER INFORMATION: 6-His tag

<400> SEQUENCE: 12

His His His His His His
1               5

<210> SEQ ID NO 13
<211> LENGTH: 25
<212> TYPE: DNA
<213> ORGANISM: Artificial Sequence
<220> FEATURE:
<223> OTHER INFORMATION: PCR primer 3P

<400> SEQUENCE: 13
aaaacccgtc ctcagttcgg attgc                                            25

<210> SEQ ID NO 14
<211> LENGTH: 25
<212> TYPE: DNA
<213> ORGANISM: Artificial Sequence
<220> FEATURE:
<223> OTHER INFORMATION: PCR primer 3M

<400> SEQUENCE: 14
ccgcgttgtt tcatcaagcc ttacg                                            25

<210> SEQ ID NO 15
<211> LENGTH: 119
<212> TYPE: PRT
<213> ORGANISM: Escherichia coli

<400> SEQUENCE: 15

Gly Ile Val Pro Gly Val Gly Ile Val Pro Gly Val Gly Ile Val Pro
1               5                   10                  15

Gly Val Gly Ile Val Pro Gly Val Gly Ile Val Pro Gly Val Gly Ile
```

```
                20              25              30
Val Pro Gly Val Gly Ile Val Pro Gly Val Gly Ile Val Pro Gly Val
         35                  40                  45

Gly Ile Val Pro Gly Val Gly Ile Val Pro Gly Val Gly Ile Val Pro
     50                  55                  60

Gly Val Gly Ile Val Pro Gly Val Gly Ile Val Pro Gly Val Gly Ile
 65                  70                  75                  80

Val Pro Gly Val Gly Ile Val Pro Gly Val Gly Ile Val Pro Gly Val
                 85                  90                  95

Gly Ile Val Pro Gly Val Gly Ile Val Pro Gly Val Gly Ile Val Pro
             100                 105                 110

Gly Val Gly Ile Pro Gly Val
         115

<210> SEQ ID NO 16
<211> LENGTH: 260
<212> TYPE: DNA
<213> ORGANISM: Homo sapiens

<400> SEQUENCE: 16
tttgtgaacc aacacctgtg cggctcacac ctggtggaag ctctctacct agtgtgcggg      60
gaacgaggct tcttctacac acccaagacc cgccggagg cagaggacct gcaggtgggg      120
caggtggagc tgggcggggg ccctggtgca ggcagcctgc agcccttggc cctggagggg      180
tccctgcaga agcgtggcat tgtggaacaa tgctgtacca gcatctgctc cctctaccag      240
ctggagaact actgcaacta                                                   260

<210> SEQ ID NO 17
<211> LENGTH: 260
<212> TYPE: DNA
<213> ORGANISM: Artificial sequence
<220> FEATURE:
<223> OTHER INFORMATION: Chloroplast modified proinsulin sequence

<400> SEQUENCE: 17
ttcgtaaacc aacacttatg tggttctcac ctagtagaag ctttatactt agtatgtggt      60
gaacgtggtt tcttctacac tcctaaaact cgtcgtgaag ctgaagattt acaagtaggt      120
caagtagaat taggtggtgg tcctggtgct ggttctttac aacctttagc tttagaaggt      180
tctttacaaa aacgtggtat tgtagaacaa tgttgtactt ctatttgttc tttataccaa      240
ttagaaaact actgtaacta                                                   260

<210> SEQ ID NO 18
<211> LENGTH: 210
<212> TYPE: DNA
<213> ORGANISM: Homo sapiens

<400> SEQUENCE: 18
ggaccggaga cgctctgcgg ggctgagctg gtggatgctc ttcagttcgt gtgtggagac      60
aggggctttt atttcaacaa gcccacaggg tatggctcca gcagtcggag ggcgcctcag      120
acaggcatcg tggatgagtg ctgcttccgg agctgtgatc taaggaggct ggagatgtat      180
tgcgcacccc tcaagcctgc caagtcagct                                        210

<210> SEQ ID NO 19
<211> LENGTH: 210
<212> TYPE: DNA
<213> ORGANISM: Homo sapiens
```

-continued

<400> SEQUENCE: 19
ggtcctgaaa ctttatgtgg tgctgaatta gtagatgctt tacaattcgt atgtggtgat      60
cgtggtttct atttcaacaa acctactggt tacggttctt cttctcgtcg tgctcctcaa     120
actggtattg tagatgaatg ttgtttccgt tcttgtgatt tacgtcgttt agaaatgtac     180
tgtgctcctt taaaacctgc taaatctgct                                      210

<210> SEQ ID NO 20
<211> LENGTH: 5
<212> TYPE: PRT
<213> ORGANISM: Artificial Sequence
<220> FEATURE:
<223> OTHER INFORMATION: Protein-based polymer (PBP) made from synthetic
      genes

<400> SEQUENCE: 20

Gly Val Gly Val Pro
1               5

<210> SEQ ID NO 21
<211> LENGTH: 605
<212> TYPE: PRT
<213> ORGANISM: Artificial Sequence
<220> FEATURE:
<223> OTHER INFORMATION: Protein-based polymer (PBP) made from synthetic
      genes.

<400> SEQUENCE: 21

Gly Val Gly Val Pro Gly Val Gly Val Pro Gly Val Gly Val Pro Gly
1               5                  10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro

-continued

```
            225                 230                 235                 240
Gly Val Gly Val Pro Gly Val Gly Val Pro Gly Val Gly Val Pro Gly
                245                 250                 255
Val Gly Val Pro Gly Val Gly Val Pro Gly Val Gly Val Pro Gly Val
            260                 265                 270
Gly Val Pro Gly Val Gly Val Pro Gly Val Gly Val Pro Gly Val Gly
        275                 280                 285
Val Pro Gly Val Gly Val Pro Gly Val Gly Val Pro Gly Val Gly Val
    290                 295                 300
Pro Gly Val Gly Val Pro Gly Val Gly Val Pro Gly Val Gly Val Pro
305                 310                 315                 320
Gly Val Gly Val Pro Gly Val Gly Val Pro Gly Val Gly Val Pro Gly
                325                 330                 335
Val Gly Val Pro Gly Val Gly Val Pro Gly Val Gly Val Pro Gly Val
            340                 345                 350
Gly Val Pro Gly Val Gly Val Pro Gly Val Gly Val Pro Gly Val Gly
        355                 360                 365
Val Pro Gly Val Gly Val Pro Gly Val Gly Val Pro Gly Val Gly Val
    370                 375                 380
Pro Gly Val Gly Val Pro Gly Val Gly Val Pro Gly Val Gly Val Pro
385                 390                 395                 400
Gly Val Gly Val Pro Gly Val Gly Val Pro Gly Val Gly Val Pro Gly
                405                 410                 415
Val Gly Val Pro Gly Val Gly Val Pro Gly Val Gly Val Pro Gly Val
            420                 425                 430
Gly Val Pro Gly Val Gly Val Pro Gly Val Gly Val Pro Gly Val Gly
        435                 440                 445
Val Pro Gly Val Gly Val Pro Gly Val Gly Val Pro Gly Val Gly Val
    450                 455                 460
Pro Gly Val Gly Val Pro Gly Val Gly Val Pro Gly Val Gly Val Pro
465                 470                 475                 480
Gly Val Gly Val Pro Gly Val Gly Val Pro Gly Val Gly Val Pro Gly
                485                 490                 495
Val Gly Val Pro Gly Val Gly Val Pro Gly Val Gly Val Pro Gly Val
            500                 505                 510
Gly Val Pro Gly Val Gly Val Pro Gly Val Gly Val Pro Gly Val Gly
        515                 520                 525
Val Pro Gly Val Gly Val Pro Gly Val Gly Val Pro Gly Val Gly Val
    530                 535                 540
Pro Gly Val Gly Val Pro Gly Val Gly Val Pro Gly Val Gly Val Pro
545                 550                 555                 560
Gly Val Gly Val Pro Gly Val Gly Val Pro Gly Val Gly Val Pro Gly
                565                 570                 575
Val Gly Val Pro Gly Val Gly Val Pro Gly Val Gly Val Pro Gly Val
            580                 585                 590
Gly Val Pro Gly Val Gly Val Pro Gly Val Gly Val Pro
        595                 600                 605
```

<210> SEQ ID NO 22
<211> LENGTH: 250
<212> TYPE: PRT
<213> ORGANISM: Artificial Sequence
<220> FEATURE:
<223> OTHER INFORMATION: Protein-based polymer (PBP) made from synthetic
    genes.

```
<400> SEQUENCE: 22

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro
225                 230                 235                 240

Gly Val Gly Val Pro Gly Val Gly Val Pro
                245                 250

<210> SEQ ID NO 23
<211> LENGTH: 7
<212> TYPE: PRT
<213> ORGANISM: Artificial Sequence
<220> FEATURE:
<223> OTHER INFORMATION: RBS sequence

<400> SEQUENCE: 23

Gly Ala Ala Gly Gly Ala Gly
1               5

<210> SEQ ID NO 24
<211> LENGTH: 200
<212> TYPE: PRT
<213> ORGANISM: Artificial Sequence
<220> FEATURE:
<223> OTHER INFORMATION: Protein-based polymer (PBP) made from synthetic
      genes.

<400> SEQUENCE: 24

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
```

```
                20                  25                  30
Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
            50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
            115                 120                 125

Val Pro Gly Val Gly Val Pro Gly Val Gly Val Pro Gly Val Gly Val
            130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro
        195                 200

<210> SEQ ID NO 25
<211> LENGTH: 100
<212> TYPE: PRT
<213> ORGANISM: Artificial Sequence
<220> FEATURE:
<223> OTHER INFORMATION: Protein-based polymer (PBP) made from synthetic
      genes.

<400> SEQUENCE: 25

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
            50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro
            100

<210> SEQ ID NO 26
<211> LENGTH: 5
<212> TYPE: PRT
```

```
-continued

<213> ORGANISM: Artificial Sequence
<220> FEATURE:
<223> OTHER INFORMATION: Chloroplast preferred Ribosome Binding Site
      (RBS) Shine-Dalgarno sequence

<400> SEQUENCE: 26

Gly Gly Ala Gly Gly
1               5
```

EXPRESSION OF HUMAN SERUM ALBUMIN IN PLASTIDS

CROSS-REFERENCE TO RELATED APPLICATIONS

This application is a continuation-in-part U.S. Ser. No. 11/230,299 filed Sep. 19, 2005 now abandoned; which is a continuation of U.S. Ser. No. 09/807,742, filed Apr. 18, 2001 now abandoned, which claims priority to U.S. Ser. No. 60/185,987, filed Mar. 1, 2000, U.S. Ser. No. 60/263,473, filed Jan. 23, 2001 and U.S. Ser. No. 60/263,668, filed Jan. 23, 2001. This application is also a continuation-in-part U.S. Ser. No. 09/079,610 filed May 15, 1998 now U.S. Pat. No. 7,129,391; which claims priority to U.S. Ser. No. 60/055,314, filed Aug. 7, 1997 and U.S. Ser. No. 60/079,042, filed Mar. 23, 1998. All of those applications are incorporated herein by reference in their entirety including any figures, tables, or drawings.

BACKGROUND

Research efforts have been made to synthesize high value pharmacologically active recombinant proteins in plants. Recombinant proteins such as vaccines, monoclonal antibodies, hormones, growth factors, neuropeptides, cytotoxins, serum proteins an enzymes have been expressed in nuclear transgenic plants (May et al., 1996). It has been estimated that one tobacco plant should be able to produce more recombinant protein than a 300-liter fermenter of $E.$ $coli$. In addition, a tobacco plant produces a million seeds, thereby facilitating large-scale production. Tobacco is also an ideal choice because of its relative ease of genetic manipulation and an impending need to explore alternate uses for this hazardous crop.

A primary reason for the high cost of production via fermentation is the cost of carbon source co-substances as well as maintenance of a large fermentation facility. In contrast, most estimates of plant production are a thousand-fold less expensive than fermentation. Tissue specific expression of high value proteins in leaves can enable the use of crop plants as renewable resources. Harvesting the cobs, tubers, seeds or fruits for food and feed and leaves for value added products should results in further economy with no additional investment.

However, one of the major limitations in producing pharmaceutical proteins in plants is their low level of foreign protein expression, despite reports of higher levee expression of enzymes and certain proteins. May et al. (1998) discuss this problem using the following examples. Although plant derived recombinant hepatitis B surface antigen was as effective as a commercial recombinant vaccine, the levels of expression in transgenic tobacco were low (0.01% of total soluble protein). Even though Norwalk virus capsid protein expressed in potatoes caused oral immunization when consumed as food (edible vaccine), expression levels were low (0.3% of total soluble protein). A synthetic gene coding for the human epidermal growth factor was expressed only up to 0.001% of total soluble protein in transgenic tobacco. Human serum albumin has been expressed only up to 0.02% of the total soluble protein in transgenic plants.

Therefore, it is important to increase levels of expression of recombinant proteins in plants to exploit plant production of pharmacologically important proteins. An alternate approach is to express foreign proteins in chloroplasts of higher plant. Foreign genes (up to 10,000 copies per cell) have been incorporated into the tobacco chloroplast genome resulting in accumulation of recombinant proteins up to 30% of the total cellular protein (McBride et al., 1994).

The aforementioned approaches (except chloroplast transformation) are limited to eukaryotic gene expression because prokaryotic genes are expressed poorly in nuclear compartment. However, several pharmacologically important proteins (such as insulin, human serum albumin, antibodies, enzymes etc.) are currently produced in prokaryotic systems (such as $E.$ $coli.$) via fermentation.

Chloroplasts are prokaryotic compartments inside eukaryotic cells. Since the transcriptional and translational machinery of the chloroplast is similar to $E.$ $coli.$ (Brixey et al., 1997), it is possible to express prokaryotic genes at very high levels in plant chloroplasts than in the nucleus. In addition, plant cell contain up to 50,000 compies of the circular plastid genome (Bendich 1987) which may amplify the foreign gene like a "plasmid in the plant cell," thereby enabling higher levels of expression. Therefore, chloroplasts are an ideal choice for expression of recombinant proteins that are currently expressed in $E.$ $Coli$ (such as insulin, human serum albumin, vaccines, antibodies, etc.). We exploited the chloroplast transformation approach to express a pharmacological protein that is of no value to the plant to demonstrate this concept, GVGVP (SEQ ID NO 20) gene has been synthesized with a codon preferred for prokaryotic (EG121) or eukaryotic (TG131) expression. Based on transcript levels, chloroplast expression of this polymer was a hundred-fold higher than nuclear expression in transgenic plants (Guda et al., 1999) Recently, we observed 16.966-fold more tps 1 transcripts in chloroplast transfomants than the highly expressing nuclear transgenic plants (Lee et al. 200, in review).

Research on human proteins in the past years has revolutionized the use of these therapeutically valuable proteins in a variety of clinical situations. Since the demand for these proteins is expected to increase considerably in the coming years, it would be wise to ensure that in the future they will be available in significantly larger amounts, preferably on a cost-effective basis. Because most genes can be expressed in many different systems, it is essential to determine which system offers the most advantages for the manufacture of the recombinant protein. An ideal expression system would be one that produces a maximum amount of safe, biologically active material at a minimum cost. The use of modified mammalian cells with recombinant DNA techniques has the advantage of resulting in products, which are closely related to those of natural origin. However, culturing these cells is intricate and can only be carried out on limited scale.

The use of microorganisms such as bacteria permits manufacture on a larger scale, but introduces the disadvantage of producing products, which differ appreciably from the products of natural origin. for example, proteins that are usually glycosylated in humans are not glycosylated by bacteria. Furthermore, human proteins that are expressed at high levels in $E.$ $coli$ frequently acquire an unnatural conformation, accompanied by intracellular precipitation due to lack of proper folding and disulfide bridges. Production of recombinant proteins in plants has many potential advantages for generating biopharmaceuticals relevant to clinical medicine. These include the following: (i) plant systems are more economical than industrial facilities using fermentation systems; (ii) technology is available for harvesting and processing plant/plant products on a large scale; (iii) elimination of the purification requirement when the plant tissue containing the recombinant protein is used as a food (edible vaccines); (iv) plants can be directed to target proteins into stable, intracellular compartments as chloroplasts, or expressed directly in chloroplasts; (v) the amount of recombinant product that can be produced approaches industrial-scale levels; and (vi) health risks due to contamination with potential human pathogens/toxins are minimized.

It has been estimated that one tobacco plant should be able to produce more recombinant protein than a 300-liter fermenter of *E. coli* (Crop Tech, VA). In addition, a tobacco plant can produce a million seeds, facilitating large-scale production. Tobacco is also an ideal choice because of its relative ease of genetic manipulation and an impending need to explore alternate uses for this hazardous crop. However, with the exception of enzymes (e.g. phytase), levels of foreign proteins produced in nuclear transgenic plants are generally low, mostly less than 1% of the total soluble protein (Kusnadi et al. 1997). (Cholera Toxin Subunit B filing) Protein accumulation levels of recombinant enzymes, like phytase and xylase were high in nuclear transgenic plants (14% and 4.1% of total soluble tobacco leaf protein respectively). This may be because their enzymatic nature made them more resistant to proteolytic degradation. May et al. (1996) discuss this problem using the following examples. Although plant derived recombinant hepatitis B surface antigen was as effective as a commercial recombinant vaccine, the levels of expression in transgenic tobacco were low (0.0066% of total soluble protein). Even though Norwald virus capsid protein expressed in potatoes caused oral immunization when consumed as food (edible vaccine), expression levels were low (0.3% of total soluble protein).

In particular, expression of human proteins in nuclear transgenic plants has been disappointingly low: e.g. human Interferon-β0.000017% of fresh weight, human serum albumin 0.02% and erythropoietin 0.0026% of total soluble protein (see table 1 in Kusnadi et al. 1997). A synthetic gene coding for the human epidermal growth factor as expressed only up to 0.001% of total soluble protein in transgenic tobacco (May et al. 1996). The cost of producing recombinant proteins in alfalfa leaves was estimated to be 12-fold lower than in potato tubers and comparable with seeds (Kusnadi et al 1997). However, tobacco leaves are much larger and have much higher biomass than alfalfa. Planet Biotechnology has recently estimated that at 50 mg/liter of mammalian cell culture or transgenic goat's milk or 50 mg/kg of tobacco leaf expression, the cost of purified IgA will be $10,000, 1000 and 50/g, respectively (Daniell et al. 2000). the cost of production of recombinant proteins will be 50-fold lower than that of *E. coli* fermentation (with 20% of 5% of biomass doubled the cost of production of *E. coli* (Petridis et al. 1995). Expression level less than 1% of total soluble protein in plants has been found to be not commercially feasible (Kusnadi et al. 1997). Therefore, it is important to increase levels of expression of recombinant proteins in plants to exploit plant production of pharmacologically important proteins.

An alternate approach is to express foreign proteins in chloroplasts of higher plants. We have recently integrated foreign genes (up to 10,000 copies per cell) into the tobacco chloroplast genome resulting in accumulation of recombinant proteins up to 46% of the total soluble protein (De Cosa et al, 2001). Chloroplast transformation utilizes two flanking sequences that, through homologous recombinant, insert foreign DNA into the spacer region between the functional genes of the chloroplast genome, thereby targeting the foreign genes to a precise location. This eliminates the position effect and gene silencing frequently observed in nuclear transgenic plants. Chloroplast genetic engineering is an environmentally friendly approach, minimizing concerns of out-cross of introduced traits via pollen to weeds or other crops (Bock and Hagemann 200, Heifetz 2000). Also, the concerns of insects developing resistance to biopesticides are minimized by hyper-expression of single insecticidal proteins (high dosage) or expression of different types of insecticides in a single transformation event (gene pyramiding). Concerns of insecticidal proteins on non-target insects are minimized by lack of expression in transgenic pollen (De Cosa et al. 2001).

Importantly, a significant advantage in the production of pharmaceutical proteins in chloroplasts is their ability to process eukaryotic proteins, including folding and formation of disulfide bridges (Drescher et al. 1998). Chaperonin proteins are present in chloroplasts (Roy, 1989; Veirling, 1991) that function in folding and assembly of prokaryotic/eukaryotic proteins. Also, proteins are activated by disulfide bond oxido/reduction cycles using the chloroplast thioredoxin system (Reulland and Miginiac-Maslow, 1999) or chloroplast protein disulfide isomersase (Kim and Mayfield, 1997). Accumulation of fully assembled, disulfide bonded form of human somatotropin via chloroplast transformation (Staub et al. 2000), oligomeric form of CTB (Henriques and Daneill, 2000) and the assembly of heavy/light chains of humanized Guy's 13 antibody in transgenic chloroplasts (Panchal et al. 2000) provide strong evidence for successful processing of pharmaceutical proteins inside chloroplasts. Such folding and assembly should eliminate the need for highly expensive in vitro processing of pharmaceutical proteins. For example, 60% of the total operating cost in the production of human insulin is associated with in vitro processing (formation of disulfide bridges and cleavage of methionine, Petridis et al. 1995).

Another major cost of insulin production is purification. Chromatography accounts for 30% of operating expenses and 70% of equipment in production of insulin (Petridis et al. 1995). Therefore, new approaches are needed to minimize or eliminate chromatography in insulin production. One such approach is the use of GVGVP (SEQ ID NO. 20) as a fusion protein to facilitate single step purification without the use of chromatography. GVGVP (SEQ ID NO. 20) is a Protein Based Polymer (PBP) made form synthetic genes. At lower temperatures this polymer exists as more extended folds into dynamic structures called .beta.-spirals that further aggregate by hydrophobic association to form twisted filaments Urry, 1991; Urry et al., 1994). Inverse temperature transition offers several advantages. It facilitates scale up of purification from grams to kilograms. Milder purification condition requires only a modest change in temperature and ionic strength. This should also facilitate higher recovery, faster purification and high volume processing. Protein purification is generally the slow step (bottleneck) in pharmaceutical product development. Though exploitation of this reversible inverse temperature transition properly, simple and inexpensive extraction and purification may be performed. The temperature at which the aggregation takes place can be manipulated by engineering biopolymers containing varying numbers of repeats and changing salt concentration in solution (McPherson et al., 1996). Chloroplast mediated expression of insulin-polymer fusion protein should eliminate the need for the expensive fermentation process as well as reagents needed for recombinant protein purification and downstream processing.

Oral delivery of insulin is yet another powerful approach that can eliminate up to 97% of the production cost of insulin (Petridis et al., 1995). For example, Sun et al. (1994) have shown that feeding a small dose of antigens conjugated to the receptor binding non-toxic B subunit moiety of the cholera toxin (CTB) suppressed systemic T cell-mediated inflammatory reactions in animals. Oral administration of a myelin antigen conjugated to CTB has been shown to protect animals against encephalomyelitis, even when given after disease induction (Sun et al., 1996). Bergerot et al. (1997) reported that feeding small amounts of human insulin conjugated to CTB suppressed beta cell destruction and clinical diabetes in adult non-obese diabetic (NOD) mice. The protective effect could be transferred by T cells from CTB-insulin treated animals and was associated with reduced insulitis. These results demonstrate that protection against autoimmune diabetes can indeed be achieved by feeding small amounts of a pancreas islet cell auto antigen linked to CTB (Bergerot et al. 1997). Conjugation with CTB facilitates antigen delivery and presentation to the Gut Associated Lymphoid Tissues (GALT) due to its affinity for the cell surface receptor $GM_1$-ganglioside located on GALT cells, for increased uptake and immunologic recognition (Arakawa et al. 1998). Transgenic potato tubers expressed up to 0.1% CTB-insulin fusion protein of total soluble protein, which retained $GM_1$-ganglioside binding affinity and native autogenicity for both CTB and insulin. NOD mice fed with transgenic potato tubers containing micro gram quantities of CTB-insulin fusion protein showed a substantial reduction in insulitis and a delay in the progression of diabetes (Arkawa et al., 1998). However, for commercial exploitation, the levels of expression should be increased in transgenic plants. Therefore, we propose here expression of CTB-insulin fusion in transgenic chloroplasts of nicotine free edible tobacco to increase levels of expression adequate for animal testing.

Taken together, low levels of expression of human proteins in *E. coli* should make chloroplasts an alternate compartment for expression of these proteins. Production of human proteins in transgenic chloroplasts should also dramatically lower the production cost. Large-scale production of insulin in tobacco in conjunction with an oral delivery system can be a powerful approach to provide treatment to diabetes patients at an affordable cost and provide tobacco farmers alternate uses for this hazardous crop. Therefore, it is first advantageous to use poly(GVGVP) (SEQ ID NO. 20) as a fusion protein to enable hyper-expression of insulin and accomplish rapid one step purification of the fusion peptide utilizing the inverse temperature transition properties of this polymer. It is further advantageous to develop insulin-CTB fusion protein for oral delivery in nicotine free edible tobacco (LAMD 605).

SUMMARY OF THE INVENTION

This invention synthesizes high value pharmaceutical proteins in transgenic plants by chloroplast expression for pharmaceutical protein production. Chloroplasts are suitable for this purpose because of their ability to process eukaryotic proteins, including folding and formation of disulfide bridges, thereby eliminating the need of expensive post-purification processing. Tobacco is an ideal choice for this purpose because of its large biomass, ease of scale-up (million seeds per plant) and genetic manipulation. We use poly (GVGVP) (SEQ ID No. 20) as a fusion protein to enable hyper-expression of insulin and accomplish rapid one step purification of fusion peptides utilizing the inverse temperature transition properties of this polymer. We also use insulin-CTB fusion protein in chloroplasts of nicotine free edible tobacco (LAMD 605) for oral delivery to NOD mice.

(Cholera Toxin Subunit B filing) This invention includes expression of native cholera toxin B subunit gene as oligomers in transgenic tobacco chloroplasts which may be utilized in connection with large-scale production of purified CTB, as well as an edible vaccine if expressed in an edible plant or as a transmucosal carrier of peptides to which it is fused to either enhanced mucosal immunity or to induce oral tolerance of the products of these peptides.

BRIEF DESCRIPTION OF DRAWINGS

FIG. 1 shows analysis of Biopolymer-Proinsulin Fusion Protein Expression.

FIG. 2 shows confirmation of chloroplast integration by PCR of polymer-proinsulin fusion gene.

FIG. 3 shows CTB gene expression in *E. Coli* and chloroplast integration.

FIG. 4 shows graphs of Cry2A protein concentration determined by ELISA in transgenic leaves.

FIG. 5 is an inmunogold labeled electron microscopy of a mature transgenic tobacco leaf.

FIG. 6 contains photographs of leaves infected with 10 μl of $8\times10^5$, $8\times10^4$, $8\times10^3$, and $8\times10^2$ cells of *P. syringae* five days after inoculation.

FIG. 7 is a graph of total plant protein mixed with 5 μl of mid-log phase bacteria from overnight culture, incubated for two hours at 25° C. at 125 rpm and grown in LB broth overnight.

FIG. 8A CTB ELISA quantification: Absorbance of CTB-antibody complex in known concentrations of total soluble plant protein was compared to absorbance of known concentration of bacterial CTB-antibody complex and the amount of CTB was expressed as percentage of the total soluble plant protein. Total soluble plant protein from young, mature and old leaves of transgenic lines 3 and 7 was quantified.

FIG. 8B $CTBGM_1$Ganglioside binding ELISA assays: Plates coated first with $GM_1$ gangliosides and BSA respectively, were plated with total soluble plant protein from lines 3 and 7, untransformed plant total soluble protein and purified bacterial CTB and the absorbance of the $GM_1$ganglioside-CTB-antibody complex in each case was measured is a graph of CTB ELISA quantification shown as a percentage of total soluble plant protein is a graph of CTB-GM1 Ganglioside binding ELISA assays.

FIG. 9 is a 12% reducing PAGE using Chemiluminescent detection of CTB oligomer with rabbit anti-cholera serum ($1^0$) and AP labeled mouse anti-rabbit IgG ($2^0$) antibodies.

FIGS. 10 A and B show reducing gels of expression and assembly of disulfide bonded Guy's 13 monoclonal antibody.

FIG. 10 C shows a non-reducing gel of expression and assembly of disulfide bonded Guy's 13 monoclonal antibody.

FIGS. 11 A-F show photographs comparing betaine aldehyde and spectinomycin selection.

FIGS. 12 A and B show biopolymer-proinsulin fusion protein expression in *E. Coli.*

FIG. 13 A shows western blots of biopolymer-proinsulin fusion protein after single step purification in *E. Coli.*

FIG. 13 B shows western blots of another biopolymer-proinsulin fusion protein after single step purification in *E. Coli.*

FIG. 13 C shows western blots of yet another biopolymer-proinsulin fusion protein after single step purification in transgenic chloroplasts.

FIG. 14 shows biopolymer-proinsulin fusion gene integration into the chloroplast genome confirmed by Southern blot analysis.

FIG. 15 A-C are a Western Blot Analysis of heavy and light chains of Guy's 13 monoclonal antibody from plant chloroplasts.

FIG. 16 is a Western Blot of transgenic potato tubers, cv Desiree expressing HSA.

Figure 1A:
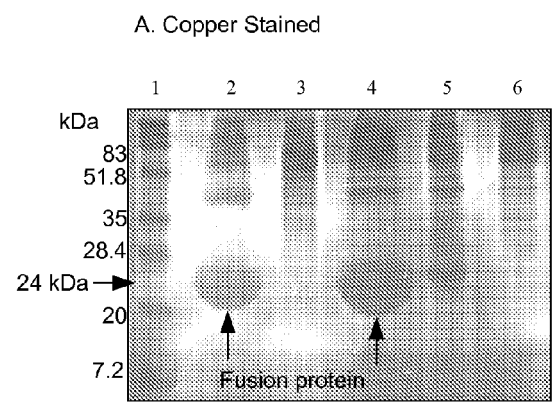
Figure 1B:
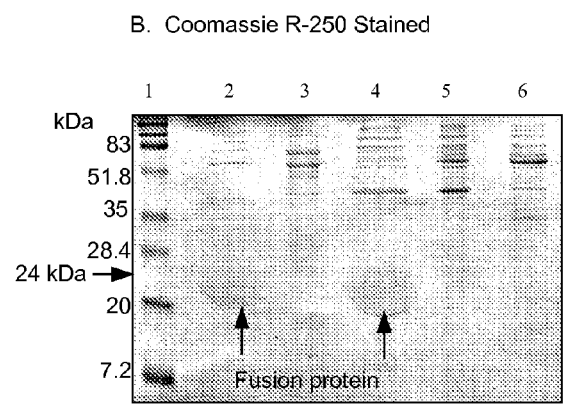

FIG. 21 pLD-LH-CTB vector and PCR analysis of control and chloroplast transformants. A. The perpendicular dotted line shows the vector sequences that are homologous to native chloroplast DNA, resulting in homologous recombination and site specific integration of the gene cassette into the chloroplast genome. Primer landing sites are also shown. B. PCR analysis: 0.8% agarose gel of PCR products using total plant DNA as template. 1 kb ladder (lane 1); Untransformed plant (lane 2); PCR products with DNA template from transgenic lines 1-10 (lanes 3-12).

FIG. 22 Southern blot analysis of $T_0$ and $T_1$ plants. A. Untransformed and transformed chloroplast genome: Transformed and untransformed plant DNA was digested with BglII and hybridized with 0.81 kb probe that contained the chloroplast flanking sequences used for homologous recombination. Southern Blot results of To lines (B) Untransformed plant DNA (lane 1); Transformed lines DNA (lanes 2-4) and $T_1$ lines (C) Transformed plant DNA (lanes 1-4) and Untransformed plant DNA (lane 5).

FIG. 23 Western blot analysis of CTB expression in E. coli and chloroplasts. Blots were detected using rabbit anti-cholera serum as primary antibody and alkaline phosphates labeled mouse anti-rabbit IgG as secondary antibody. A. E. coli protein analysis: Purified bacterial CTB, boiled (lane 1); Unboiled 24 h and 48 h transformed (lanes 2 &4) and untransformed (lanes 3 &5) E. coli ell extracts. Plant protein analysis: B. Color Development detection: Boiled, untransformed protein (lane 1); Boiled, purified CTB antigen (lane 2): Boiled, protein from 4 different transgenic lines (lanes 3-6). C. Chemiluminescent detection: Plant protein-Untransformed, unboiled (lane 1); Untransformed, boiled (lane 2); Transgenic lines 3 & 7, boiled (lanes 3 & 5), Transgenic line 3, unboiled (lane 4); Purified CTB antigen boiled (lane 6), unboiled (lane 7); Marker (lane 8).

Figure 24:
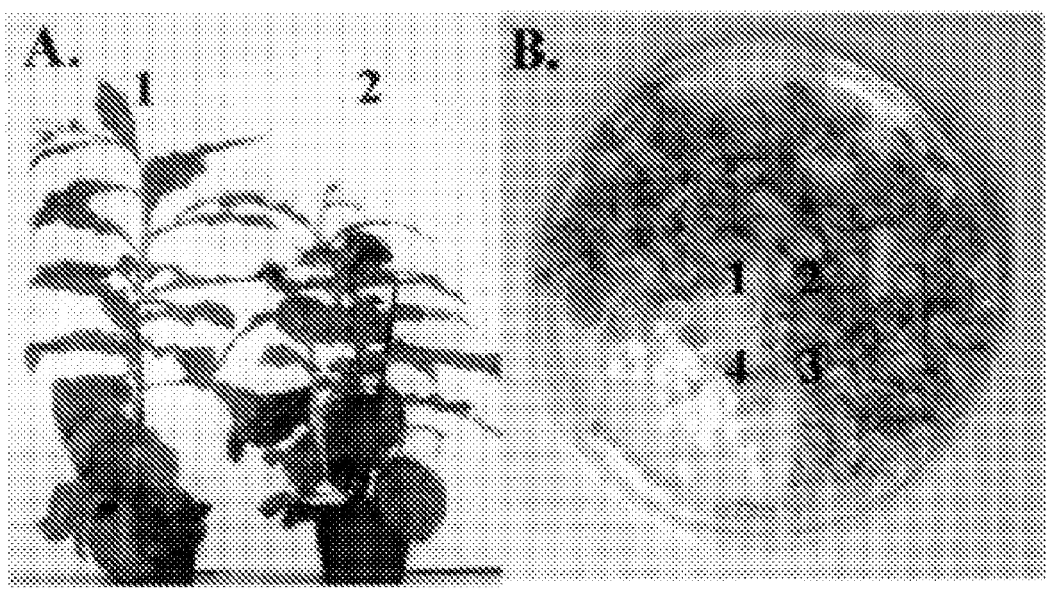

FIG. 24 Plant phenotypes; 1: Confirmed transgenic line 7; 2: Untransformed plant B. 10-day-old seedlings of $T_1$ transformed (1, 2 & 3) and untransformed plant (4) plated on 500 mg/L spectinomycin selection medium.

FIG. 25 shows the cloning of the psbA 5' untranslated region (5'UTR) from the chloroplast genome.

FIG. 26 shows the SOEing of the 5'UTR to the CTB-human proinsulin sequence.

FIG. 27 shows a comparison of the DNA sequences of native human proinsulin and plastid modified proinsulin.

Figure 28:
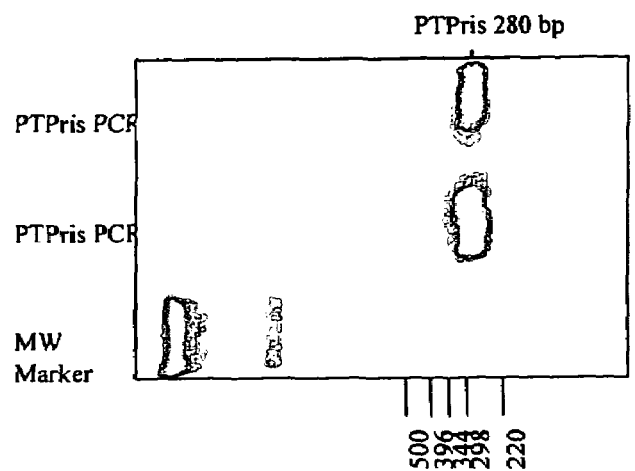

FIG. 28 shows recursive PCR to synthesize the chloroplast modified proinsulin (Ptpris).

Figure 29:
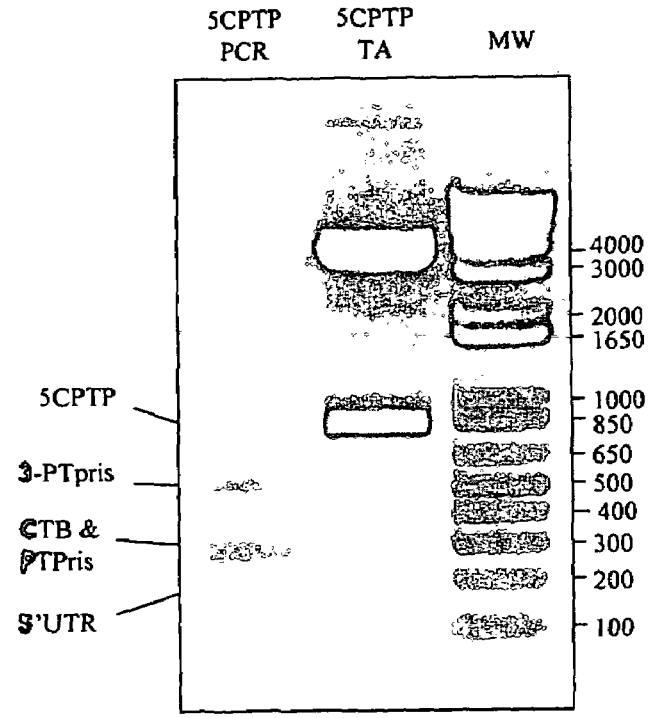

FIG. 29 shows SOEing of the 5'UTR, CTB and plastid modified proinsulin, which results in the fusion of all three sequences denoted as 5CPTP.

Figure 30:
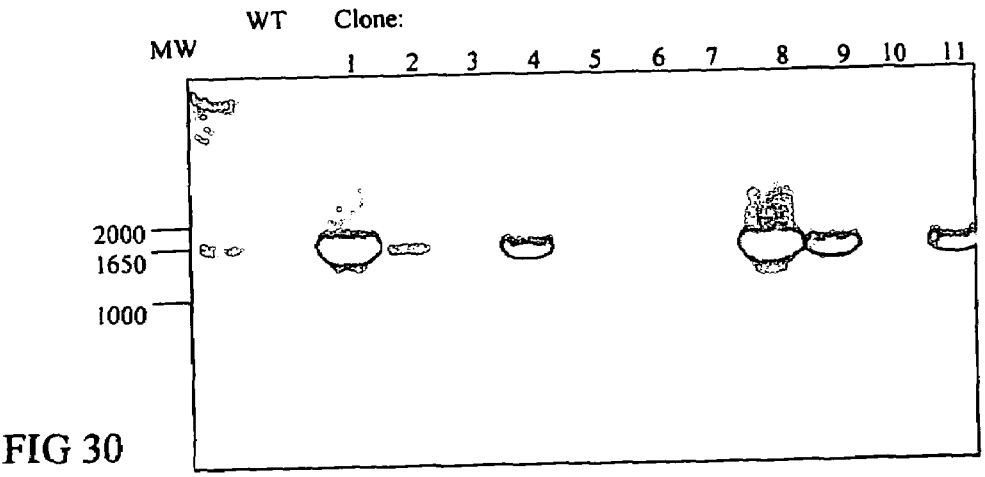

FIG. 30 shows the PCR products to confirm construct integration into the chloroplast genome using two primers, 3P and 3M.

Figure 31A:
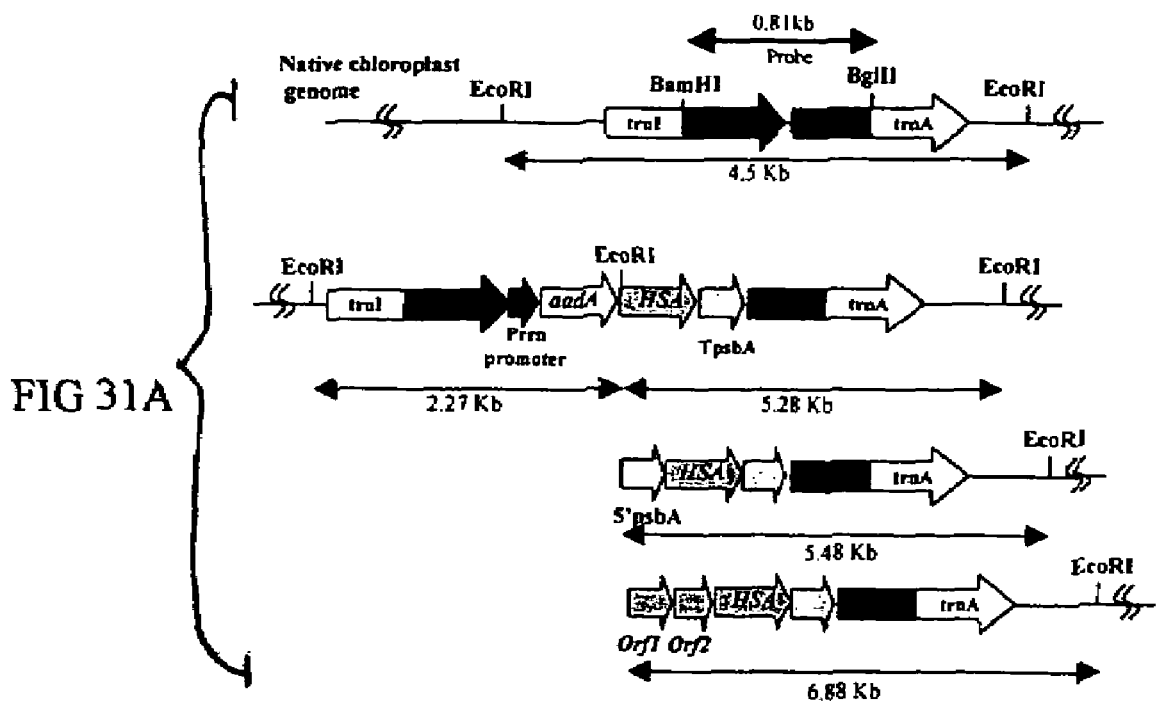
Figure 31B:
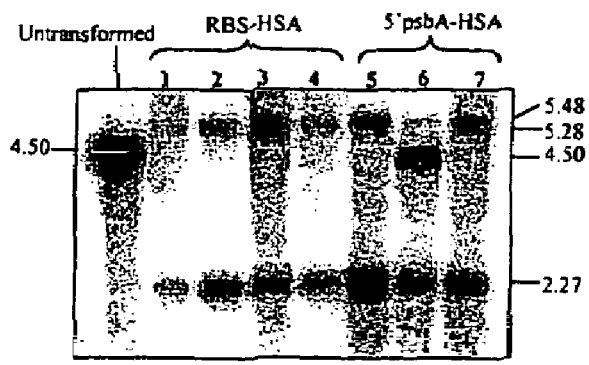
Figure 31C:
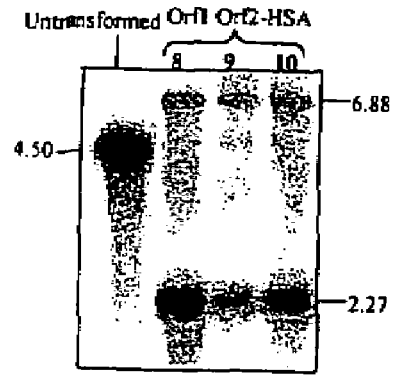

FIG. 31 shows Southern Blot of HSA chloroplast transgenic plants. Untransformed tobacco DNA vs. transgenic tobacco DNA digested with EcoRI.

FIG. 32 shows Northern Blot of HSA chloroplast transgenic plants using HSA probe (1.8 kb).

FIG. 33 shows ELISA of HSA transgenic plants.

FIG. 34A shows IGF-I native sequence coding for the mature protein

FIG. 34B shows IGF-I optimized sequence according to chloroplast preferred codon usage.

FIG. 34C shows IGF-I synthetic gene after recursive PCR

Figure 35:
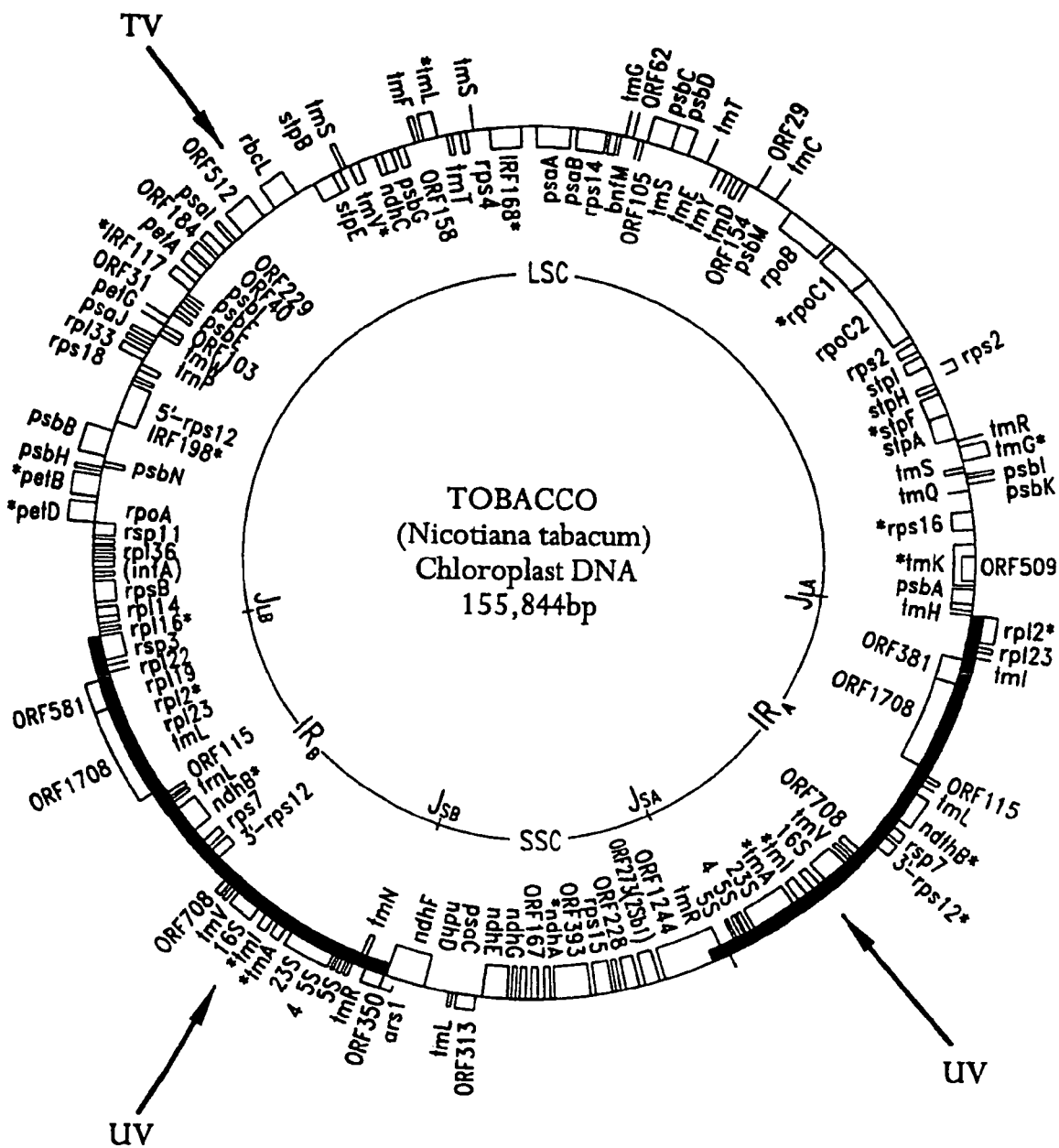

FIG. 35 shows a map of the tobacco chloroplast genome. The thick lines in the genome map represent the inverted repeat regions of the chloroplast genome. The arrows labeled "W" represent the insertion sequences for the preferred embodiment of the universal integration and expression vector (UV); the arrow labelled "TV" represents the insertion sequence for the tobacco vector (TV).

Figure 36:
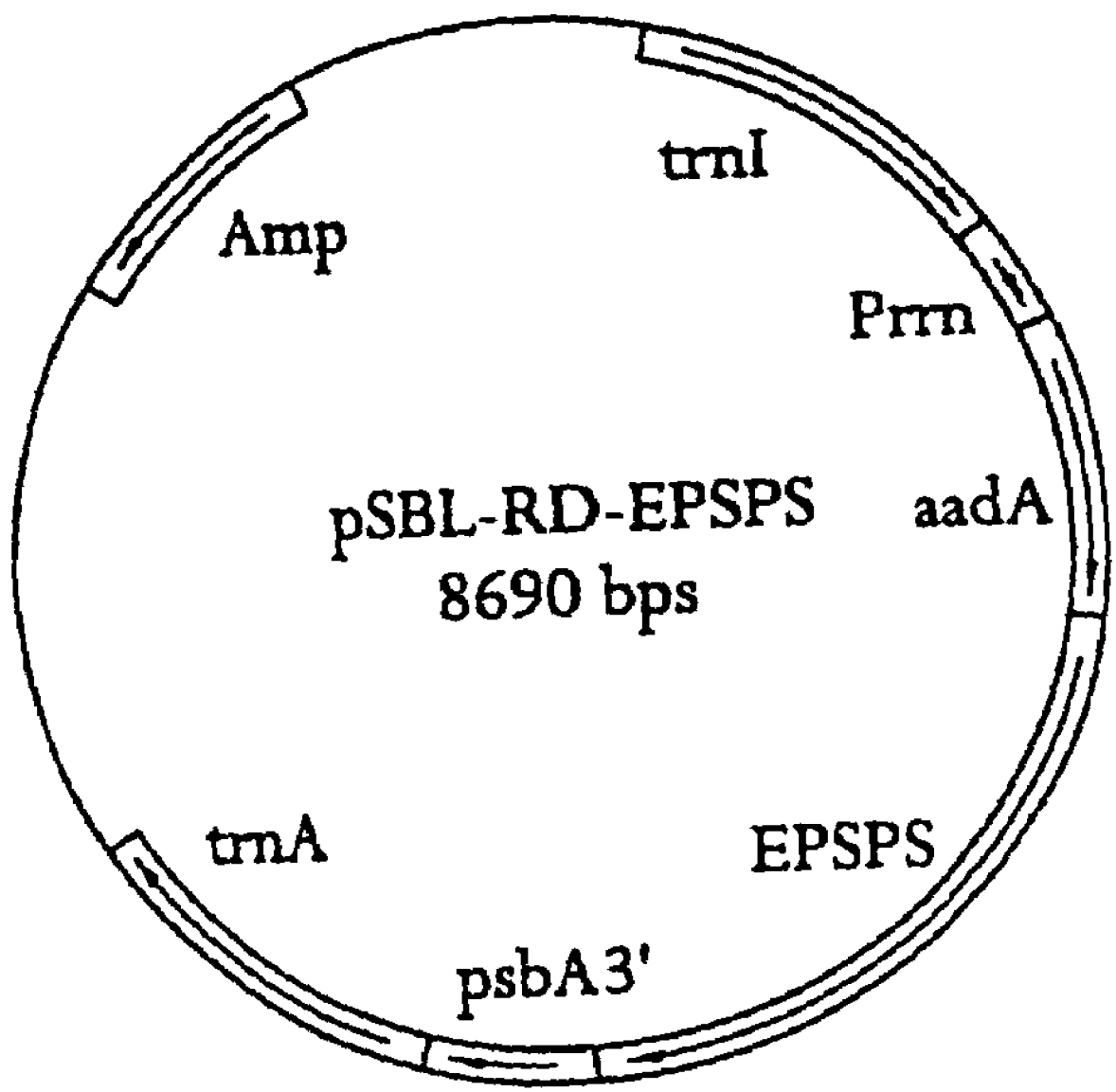

FIG. 36 shows the universal chloroplast expression and integration vector (UV), pSBL-RD-EPSPS for expression of herbicide resistance.

FIGS. 37A-C show construction of the vector pSBL-Ct border.

Figure 38:
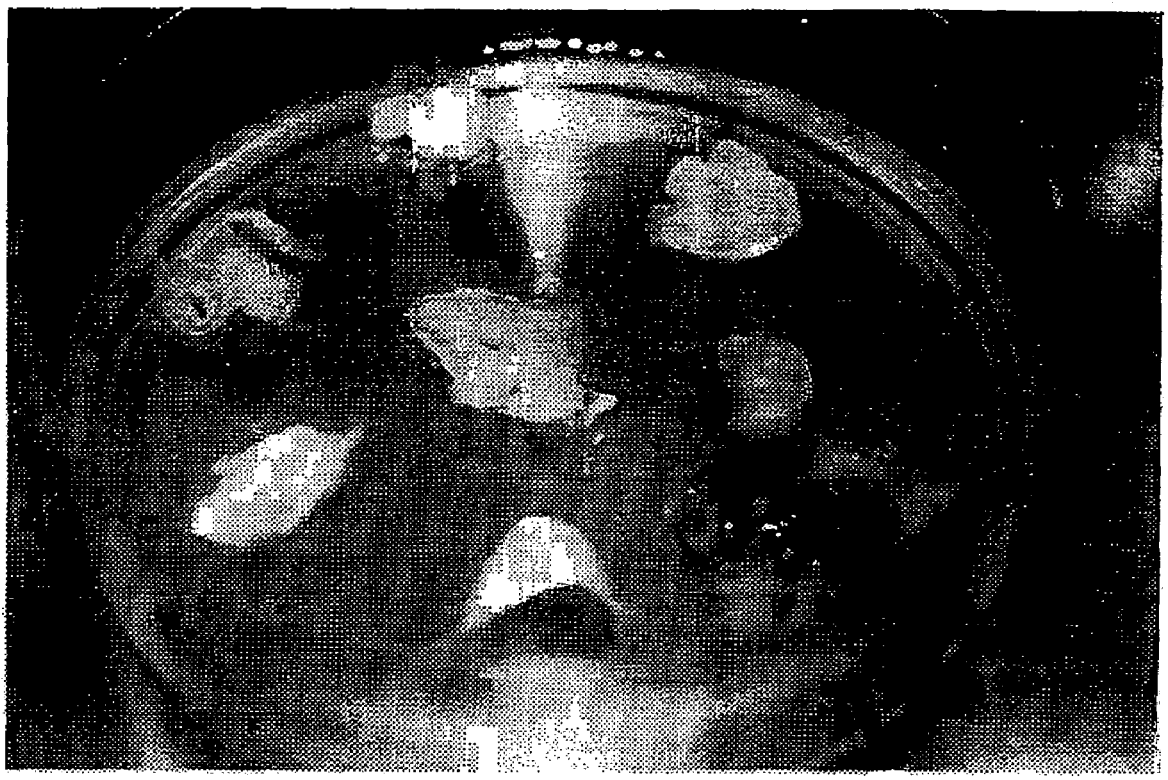

FIG. 38 shows transformed and untransformed tobacco plants growing in the presence of spectinomycin indicating non-lethal selection on the medium (500 yg/ml). Note growth of transformed (bleached) and untransformed leaves (green).

DETAILED DESCRIPTION

A remarkable feature of chloroplast genetic engineering is the observation of exceptionally large accumulation of foreign proteins in transgenic plants. This can be as much as 46% of CRY protein in total soluble protein, even in bleached old leaves (DeCosa et al. 2001). Stable expression of a pharmaceutical protein in chloroplasts was first reported for GVGVP (SEQ ID NO. 20), a protein based polymer with varied medical applications (such as the prevention of post-surgical adhesions and scars, wound coverings, artificial pericardia, tissue reconstruction and programmed drug delivery) (Guda et al. 2000). Subsequently, expression of the human somatotropin via the tobacco chloroplast genome (Staub et al. 2000) to high levels (7% of total soluble protein) was observed. The following investigations that are in progress illustrate the power of this technology to express small peptides, entire operons, vaccines that require oligomeric proteins with stable disulfide bridges and monoclonals that require assembly of heavy/light chains via chaperoning. It is essential to develop a selection system free of antibiotic resistant genes for the edible insulin approach to be successful. One such marker free chloroplast transformation system has been accomplished (Daniell et al. 2000). Experiments are in progress to develop chloroplast transformation of edible leaves (alfalfa and lettuce) for the practical applications of this approach.

In our research, we use insulin as a model protein to demonstrate its production as a value added trait in transgenic tobacco. Most importantly, a significant advantage in the production of pharmaceutical proteins in chloroplasts is their ability to process eukaryotic protein, including folding and formation of disulfide bridges (Dreshcher et al., 1998). Chaperonin proteins are present in chloroplasts (Verling 1991; Roy 1989) that function in folding and assembly of prokaryotic/eukaryotic proteins. Also, proteins are activated by disulfide bond oxido/reduction cycles using the chloroplast inicredoxin system (Reulland and Mirginiac-Maslow, 1999) or chloroplast protein disulfide isomerase (Kim and Mayfield, 1997). Accumulation of fully assembled, disulfide bonded form of antibody inside chloroplasts, even though plastics were not transformed (During et al. 1990), provides strong evidence for (Panchal et al. 2000, in review). Such folding and assembly eliminates the need for post-purification processing of pharmaceutical proteins. Chloroplasts may also be isolated from crude homogenates by centrifugation (1500×g). This fraction is free of other cellular proteins. Isolated chloroplasts are burst open by osmotic shock to release foreign proteins that are compartmentalized in this organelle along with few other native soluble proteins (Daniel and McFadden, 1987).

GVGVP (SEQ ID NO. 20) is a PBP made from synthetic genes. At lower temperatures the polymers exist as more extended molecules which, on raising the temperature above the transition range, hydrophobically fold into dynamic structures called .beta.-spirals that further aggregate by hydrophobic association to form twisted filaments (Urry, 1991; Urry, et al., 1994). Inverse temperature transition offers several advantages. Expense associated with chromatographic resins and equipment are eliminated. It also facilitates scale up of purification from grams to kilograms. Milder purification conditions use only a modest change in temperature and ionic strength. This also facilitates higher recovery, faster purification and high volume processing. Protein purification is generally the slow step (bottleneck) in pharmaceutical product development. Though exploitation of this reversible inverse temperature transition property, simple and inexpensive extraction and purification is performed. The temperature at which the aggregation takes place can be manipulated by engineering biopolymers containing varying numbers of repeats and changing salt concentration in solution (McPherson et al., 1996). Chloroplast mediated expression of insulin-polymer fusion protein eliminates the need for the expensive fermentation process as well as reagents needed for recombinant protein purification and downstream processing.

Large-scale production of insulin in plants in conjunction with an oral delivery system is a powerful approach to provide insulin to diabetes patients at an affordable cost and provide tobacco farmers alternate uses for this hazardous crop. For example, Sun et al. (1994) showed that feeding a small dose of antigens conjugated to the receptor binding non-toxic B subunit moiety of the cholera toxin (CTB) suppressed systemic T cell-mediated inflammatory reactions in animals. Oral administration of a myelin antigen conjugated to CTB has been shown to protect animals against encephalomyelitis, even when given after disease induction (Sun et al. 1996). Bergerot et al. (1997) reported that feeding small amounts of human insulin conjugated to CTB suppressed beta cell destruction and clinical diabetes in adult non-obese diabetic (NOD) mice. The protective effect could be transferred by T cells from CTB-insulin treated animals and was associated with reduced insulitis. These results demonstrate that protection against autoimmune diabetes can indeed be achieved by feeding small amounts of pancreas islet cell auto antigen linked to CTB (Bergerot, et al. 1997). Conjugation with CTB facilitates antigen delivery and presentation to the Gut Associated Lymphoid Tissues (GALT) due to its affinity for the cell surface receptor GM-ganglioside located on GALT cells, for increased uptake and immunologic recognition (Arakawa et al. 1998). Transgenic potato tubers expressed up to 0.1% CTB-insulin fusion protein of total soluble protein, which retained GM-ganglioside binding affinity and native autogenicty for both CTB and insulin. NOD mice fed with transgenic potato tubers containing microgram quantities of CTB-insulin fusion protein showed a substantial reduction in insulitis and a delay in the progression of diabetes (Arkawa et al., 1998). However, for commercial exploitation, the levels of expression need to be increased in transgenic plants. Therefore, we undertook the expression of CTB-insulin fusion in transgenic chloroplasts of nicotine free edible tobacco to increase levels of expression adequate for animal testing.

In accordance with one advantageous feature of this invention, we use poly(GVGVP) (SEQ ID NO. 20) as a fusion protein to enable hyper-expression of insulin and accomplish rapid one step purification of fusion peptides utilizing the inverse temperature transition properties of this polymer. In another advantageous feature of this invention, we develop insulin-CTB fusion protein for oral delivery in nicotine free edible tobacco (LAMD 605). Both features are accomplished as follows: a) Develop recombinant DNA vectors for enhanced expression of Proinsulin as fusion proteins with GVGVP (SEQ ID NO. 20 or CTB via chloroplast genomes of tobacco, b) Obtain transgenic tobacco (Petit Havana & LAMD 605) plants, c) Characterize transgenic expression of proinsulin polymer or CTB fusion proteins using molecular and biochemical methods in chloroplasts, d) Employ existing or modified methods of polymer purification from transgenic leaves, e) Analyze Mendelian or maternal inheritance of transgenic plants, f) Larch scale purification of insulin and comparison of current insulin purification methods with polymer-based purification method in $E.\ coli$ and tobacco, g) Compare natural refolding chloroplasts with in vitro processing, h) Characterization (yield and purity) of proinsulin produced in $E.\ coli$ and transgenic tobacco, and i) Assessment of diabetic symptoms in mice fed with edible tobacco expressing CTB-insulin fusion protein.

Diabetes and Insulin: Insulin lowers blood glucose (Oakly et al. 1973). This is a result of its immediate effect in increasing glucose uptake in tissues. In muscle, under the action of insulin, glucose is more readily taken up and either converted to glycogen and lactic acid or oxidized to carbon dioxide. Insulin also affects a number of important enzymes concerned with cellular metabolism. It increases the activity of glucokinase, which phosphoryiates glucose, thereby increasing the rate of glucose metabolism in the liver. Insulin also suppresses gluconeogenesis by depressing the function of liver enzymes, which operate the reverse pathway from proteins to glucose. Lack of insulin can restrict the transport of glucose into muscle and adipose tissue. This results in increases in blood glucose levels (hyperglycemia). In addition, the breakdown of natural fat to free fatty acids and glycerol is increased and there is a rise in the fatty acid content in the blood. Increased catabolism of fatty acids by the liver results in greater production of ketone bodies. They diffuse from the liver and pass to the muscles for further oxidation. Soon, ketone body production rate exceeds oxidation rate and ketosis results. Fewer amino acids are taken up by the tissues and protein degradation results. At the same time, gluconeogenesis is stimulated and protein is used to produce glucose. Obviously, lack of insulin has serious consequences.

Diabetes is classified into types I and II. Type I is also known as insulin dependent diabetes mellitus (IDDM). Usually this is caused by a cell-mediated autoimmune destruction of the pancreatic β-cells (Davidson, 1998). Those suffering from this type are dependent on external sources of insulin. Type II is known as noninsulin-dependent diabetes mellitus (NIDDM). This usually involved resistance to insulin in combination with its underproduction. These prominent diseases have led to extensive research into microbial production of recombinant human insulin (rHI).

Expression of Recombinant Human Insulin in $E.\ coli$: In 1978, two thousand kilograms of insulin were used in the world each year; half of this was used in the United States (Steiner et al., 1978). At that time, the number of diabetics in the US were increasing 6% every year (Gunby, 1978). In 1997-98, 10% increase in sales of diabetes care products and 19% increase in insulin products have been reported by Novo Nordisk (world's leading supplier of insulin), making it a 7.8 billion dollar industry. Annually, 160,000 Americans are killed by diabetes, making it the fourth leading cause of death. Many methods of production of rHI have been developed.

Insulin genes were first chemically synthesized for expression in *Escherichia coli* (Crea et al., 1978). These genes encoded separate insulin A and B chains. The genes were each expressed in *E. coli* as fusion proteins with the β-galactosidase (Goeddel et al., 1979). The first documented production of rHI using this system was reported by David Goeddel from Genentech (Hall, 1988). For reasons explained later, the genes were fused to the Trp synthase gene. This fusion protein was approved for commercial production by Eli Lilly in 1982 (Chance and Frank, 1993) with a product name of Humulin. As of 1986, Humulin was produced from proinsulin genes. Proinsulin contains both insulin chains and the C-peptide that connects them. Data concerning commercial production of Humulin and other insulin products is now considered proprietary information and is not available to the public.

Delivery of Human Insulin: Insulin has been delivered intravenously in the past several years. However, more recently, alternate methods such as nasal spray are also available. Oral delivery of insulin is yet another new approach (Mathiowitz et al., 1997). Engineered polymer microspheres made of biologically erodable polymers, which display strong interactions with gastrointestinal mucus and cellular linings, can traverse both mucosal absorptive epithelium and the follicle-associated epithelium, covering the lymphoid tissue of Peyer's patches. Polymers maintain contact with intestinal epithelium for extended periods of time and actually penetrate through and between cells. Animals fed with the poly(FA:PLGA)-encapsulated insulin preparation were able to regulate the glucose load better than controls, confirming that insulin crossed the intestinal barrier and was released from the microspheres in a biologically active form (Mathiowitz et al, 1997).

Protein Based Polymers (PBP): The synthetic gene that codes for a bioelastic PBP was designed after repeated amino acid sequences GVGVP, observed in all sequenced mammalian elastin proteins (Yeh et al. 1987). Elastin is one of the strongest known natural fibers and is present in skin, ligaments, and arterial walls. Bioelastic PBPs containing multiple repeats of this pentamer have remarkable elastic properties, enabling several medical and non-medical applications (Urry et al. 1993, Urry 1995, Daniell 1995). GVGVP (SEQ ID NO. 20) polymers prevent adhesions following surgery, aid in reconstructing tissues and delivering drugs to the body over an extended period of time. North American Science Associates, Inc. reported that GVGVP (SEQ ID NO. 20) polymer is non-toxic in mice, non-sensitizing and non-antigenic in guinea pigs, and non-pyrogenic in rabbits (Urry et al. 1993). Researchers have also observed that inserting sheets of GVGVP (SEQ ID NO. 20) at the sites of contaminated wounds in rats reduces the number of adhesions that form as the wounds heal (Urry et al. 1993). In a similar manner, using the GVGVP (SEQ ID NO. 20) to encase muscles that are cut during eye surgery in rabbits prevents scarring following the operation (Urry et al. 1993, Urry 1995). Other medical applications of bioelastic PBPs include tissue reconstruction (synthetic ligaments and arteries, bones), wound coverings, artificial pericardia, catheters and programmed drug delivery (Urry, 1995; Urry et al., 1993, 1996).

We have expressed the elastic PBP (GVGVP)$_{121}$ (SEQ ID NO. 21) in *E. coli* (Guda et al. 1995, Brixey et al. 1997), in the fungus *Aspergillus nidulans* (Herzog et al. 1997), in cultured tobacco cells (Zhang et al. 1995), and in transgenic tobacco plants (Zhang et al. 1996). In particular, (GVGVP)$_{121}$ (SEQ ID NO. 21) has been expressed to such high levels in *E. coli* that polymer inclusion bodies occupied up to about 90% of the cell volume. Also, inclusion bodies have been observed in chloroplasts of transgenic tobacco plants (see attached article, Daniell and Guda, 1997). Recently, we reported stable transformation of the tobacco chloroplasts by integration and expression the biopolymer gene (EG121), into the Large Single Copy region (5,000 copies per cell) or the Inverted Repeat region (10,000 copies per cell) of the chloroplast genome (Guda et al., 1999).

PBP as Fusion Proteins: Several systems are now available to simplify protein purification including the maltose binding protein (Marina et al. 1988), glutethione S-transferase (Smith and Johnson 1988), biotinylated (Tsao et al. 1996), thioredoxin (Smith et al. 1998) and cellulose binding (Ong et al. 1989) proteins. Recombinant DNA vectors for fusion with short peptides are now available to effectively utilize aforementioned fusion proteins in the purification process (Smith et al. 1998; Kim and Raines, 1993; Su et al. 1992). Recombinant proteins are generally purified by affinity chromatography, using ligands specific to carrier proteins (Nilsson et al. 1997). While these are useful techniques for laboratory scale purification, affinity chromatography for large-scale purification is time consuming and cost prohibitive. Therefore, economical and non-chromatographic techniques are highly desirable. In addition, a common solution to N-terminal degradation of small peptides is to fuse foreign peptides to endogenous *E. coli* proteins. Early in the development of this technique, β-galactosidase (β-gal) was used as a fusion protein (Goldberg and Goff, 1986). A drawback of this method was that the β-gal protein is of relatively high molecular weight (MW 100,000). Therefore, the proportion of the peptide product in the total protein is low. Another problem associated with the large (β-gal fusion is early termination of translation (Burnett, 1983; Hall, 1988). This occurred when (β-gal was used to produce human insulin peptides because the fusion was detached from the ribosome during translation thus yielding incomplete peptides. Other proteins of lower molecular weight proteins have been used as fusion proteins to increase the peptide production. For example, better yields were obtained with the tryptophan synthase (190aa) fusion proteins (Hall, 1988; Burnett, 1983).

Accordingly, one achievement according to this invention is to use poly(GVGVP) (SEQ. ID NO. 20 as a fusion protein to enable hyper-expression of insulin and accomplish rapid one step purification of the fusion peptide. At lower temperature the polymers exist as more extended molecules which, on raising the temperature above the transition range, hydrophobically fold into dynamic structures called (β-spirals that further aggregate by hydrophobic association to form twisted filaments (Urry, 1991). Through exploitation of this reversible property, simple and inexpensive extraction and purification is performed. The temperature at which aggregation takes place ($T_1$) is manipulated by engineering biopolymers containing varying numbers of repeats or changing salt concentration (McPherson et al., 1996). Another group has recently demonstrated purification of recombinant proteins by fusion with thermally responsive polypeptides (Meyer and Chilkoti, 1999). Polymers of different sizes have been synthesized and expressed in *E. coli*. This approach also eliminates the need for expensive reagents, equipment and time required for purification.

Cholera Toxin β subunit as a fusion protein: *Vibrio cholerae* causes diarrhea by colonizing the small intestine and producing enterotoxins, of which the cholera toxin (CT) is considered the main cause of toxicity. CT is a hexameric AB$_5$ protein having one 27 Kda A subunit which has toxic ADP-ribosyl transferase activity and a non-toxic pentamer of 11.6 kDa B subunits that are non-covalently linked into a very stable doughnut like structure into which the toxic active (A) subunit is inserted. The A subunit of CT consists of two fragments -A1 and A2 which are linked by a disulfide bond. The enzymatic activity of CT is located solely on the A1 fragment (Gill, 1976). The A2 fragment of the A subunit links A1 fragment and the B pentamer. CT binds via specific interactions of the B subunit pentamer with GM1 ganglioside, the membrane receptor, present on the intestinal epithelial cell surface of the host. The A subunit is then translocated into the cell where it ADP-ribosylates the Gs subunit of adenylate cyclase bringing about the increased levels of cyclic AMP in affected cells that is associated with the electrolyte and fluid loss of clinical cholera (Lebens et al. 1994). For optimal enzymatic activity, the A1 fragment needs to be separated from the A2 fragment by proteolytic cleavage of the main chain and by reduction of the disulfide bond linking them (Mekalanos et al., 1979).

The Expression and assembly of CTB in transgenic potato tubers has been reported (Arakawa et al. 1997). The CTB gene including the leader peptide was fused to an endoplasmic reticulum retention signal (SEKDEL) (SEQ ID NO. 2) at the 3' end to sequester the CTB protein within the lumen of the ER. The DNA fragment encoding the 21-amino acid leader peptide of the CTB protein was retained to direct the newly synthesized CTB protein into the lumen of the ER. Immunoblot analysis indicated that the plant derived CTB protein was antigenically indistinguishable from the bacterial CTB protein and that oligomeric CTB molecules (Mr~50 kDa) were the dominant molecular species isolated from transgenic potato leaf and tuber tissues. Similar to bacterial CTB, plant derived CTB dissociated into monomers (Mr~45 kDa) during heat acid treatment.

Enzyme linked immunosorbent assay methods indicated that plant synthesized CTB protein bound specifically to GM1 gangliosides, the natural membrane receptors of Cholera Toxin. The maximum amount of CTB protein detected in auxin induced transgenic potato leaf and tuber issues was approximately 0.3% of the total soluble protein. The oral immunization of CD-1 mice with transgenic potato tissues transformed with the CTB gene (administered at weekly intervals for a month with a final booster feeding on day 65) has also been reported. The levels of serum and mucosal anti-cholera toxin antibodies in mice were found to generate protective immunity against the cytopathic effects of CT holotoxin.

Following intraileal injection with CT, the plant immunized mice showed up to a 60% reduction in diarrheal fluid accumulation in the small intestine. Systemic and mucosal CTB-specific antibody titers were determined in both serum and feces collected from immunized mice by the class-specific chemiluminescent ELISA method and the endpoint titers for the three antibody isotypes (IgM, IgG and IgA) were determined.

The extent of CT neutralization in both Vero cell and ileal loop experiments suggested that anti-CTB antibodies prevent CT binding to cellular GM1-gangliosides. Also, mice fed with 3 g of transgenic potato exhibited similar intestinal protection as mice gavaged with 30 g of bacterial CTB. Recombinant LTB [rLTB] (the heat labile enterotoxin produced by Enterotoxigenic *E. coli*) which is structurally, functionally and immunologically similar to CTB was expressed in transgenic tobacco (Arntzen et al. 1998; Haq et al., 1995). They have reported that the rLTB retained its antigenicity as shown by immunoprecipitation of rLTB with antibodies raised to rLTB from *E. coli*. The rLTB protein was of the right molecular weight and aggregated to form the pentamer as confirmed by gel permeation chromatography.

CTB has also been demonstrated to be an effective carrier molecule for induction of mucosal immunity to polypeptides to which it is chemically or genetically conjugated (McKenzie et al, 1984; Dertzbaugh et al, 1993). The production of immunomodulatory transmucosal carrier molecules, such as CTB, in plants may greatly improve the efficacy of edible plant vaccines (Haq et al, 1995; Thanavala et al, 1995; Mason et al, 1996) and may also provide novel oral tolerance agents for prevention of such autoimmune diseases as Type 1 diabetes (Zhang et al, 1991), Rheumatoid arthritis (Trentham et al, 1993), multiple sclerosis (Khoury et al, 1990; Miller et al, 1992; Weiner et al, 1993) as well as the prevention of allergic and allograft rejection reactions (Savegh et al, 1992; Hancock et al, 1993).

CTB, when administered orally (Lebens and Holmgren, 1994), is a potent mucosal immunogen, which can neutralize the toxicity of the CT holotoxin by preventing it from binding to the intestinal cells (Mor et al. 1998). This is believed to be a result of binding to eukaryotic cell surfaces via the $G_{M1}$ gangliosides, receptors present on the intestinal epithelial surface, thus eliciting a mucosal immune response to pathogens (Lipscombe et al. 1991) and enhancing the immune response when chemically coupled to other antigens (Dertzbaugh and Elson, 1993; Holmgren et al. 1993; Nashar et al. 1993; Sun et al. 1994).

Therefore, expressing a CTB-proinsulin fusion is an ideal approach for oral delivery of insulin.

Chloroplast Genetic Engineering: Several environmental problems related to plant genetic engineering now prohibit advancement of this technology and prevent realization of its full potential. One such common concern is the demonstrated escape of foreign genes through pollen dispersal from transgenic crop plants to their weedy relatives creating super weeds or causing gene pollution among other crops or toxicity of transgenic pollen to non-target insects such as butterflies. The high rates of gene flow from crops to wild relatives (as high as 38% in sunflower and 50% in strawberries) are certainly a serious concern. Clearly, maternal inheritance (lack of chloroplast DNA in pollen) of the herbicide resistance gene via chloroplast genetic engineering has been shown to be a practical solution to these problems (Daniell et al, 1998). Another common concern is the sub-optimal production of *Bacillus thuringiensis* (B.t.) insecticidal protein or reliance on a single (or similar) B.t. protein in commercial transgenic crops resulting in B.t. resistance among target pests. Clearly, different insecticidal proteins should be produced in lethal quantities to decrease the development of resistance. Such hyper-expression of a novel B.t. protein in chloroplasts has resulted in 100% mortality of insects that are up to 40,000-fold resistant to other B.t. proteins (Kota et al. 1999). Therefore, chloroplast genome is an attractive target for expression of foreign genes due to its ability to express extraordinarily high levels of foreign proteins and efficient containment of foreign genes through maternal inheritance.

When we developed the concept of chloroplast genetic engineering (Daniell and McFadden, 1988 U.S. Patents; Daniell, World Patent, 1999). It was possible to introduce isolated intact chloroplasts into protoplasts and regenerate transgenic plants (Carlson, 1973). Therefore, early investigations on chloroplast transformation focused on the development of in organelle systems using intact chloroplasts capable of efficient and prolonged transcription and translation (Daniell and Rebeiz, 1982; Daniell et al., 1983, 1986) and expression of foreign genes in isolated chloroplasts (Daniell and McFadden, 1987). However, after the discovery of the gene gun as a transformation device (Daniell, 1993), it was possible to transform plant chloroplasts without the use of isolated plastids and protoplasts. Chloroplast genetic engineering was accomplished in several phases. Transient expression of foreign genes in plastids of dicots (Daniell et al., 1990; Ye et al., 1990) was followed by such studies in monocots (Daniell et al., 1991). Unique to the chloroplast genetic engineering is the development of a foreign gene expression system using autonomously replicating chloroplast expression vectors (Daniell et al., 1990). Stable integration of a selectable marker gene into the tobacco chloroplast genome (Svab and Maliga, 1993) was also accomplished using the gene gun. However, useful genes conferring valuable traits via chloroplast genetic engineering have been demonstrated only recently. For example, plants resistant to B.t. sensitive insects were obtained by integrating the crylAc gene into the tobacco chloroplast genome (McBride et al., 1995). Plants resistant to B.t. resistant insects (up to 40,000 fold) were obtained by hyper-expression of the cryilA gene within the tobacco chloroplast genome (Kota et al., 1999). Plants have also been genetically engineered via the chloroplast genome to confer herbicide resistance and the introduced foreign genes were maternally inherited, overcoming the problem of cut-cross with weeds (Daniell et al., 1998). Chloroplast genetic engineering has also been used to produce pharmaceutical products that are not used by plants (Guda et al., 2000). Chloroplast genetic engineering technology is currently being applied to other useful crops (Sidorov et al. 1999; Daniell. 1999).

Most transformation techniques co-introduce a gene that confers antibiotic resistance, along with the gene of interest to impart a desired trait. Regenerating transformed cells in antibiotic containing growth media permits selection of only those cells that have incorporated the foreign genes. Once transgenic plants are regenerated, antibiotic resistance genes serve no useful purpose but they continue to produce their gene products. One among the primary concerns of genetically modified (GM) crops is the presence of clinically important antibiotic resistance gene products in transgenic plants that could inactivate oral doses of the antibiotic (reviewed by Puchta 2000; Daniell 1999A). Alternatively, the antibiotic resistant genes could be transferred to pathogenic microbes in the gastrointestinal tract or soil rendering them resistant to treatment with such antibiotics. Antibiotic resistant bacteria are one of the major challenges of modern medicine. In Germany, GM crops containing antibiotic resistant genes have been banned from release (Peerenboom 2000).

Chloroplast genetic engineering offers several advantages over nuclear transformation including high levels of gene expression and gene containment but utilizes thousands of copies of the most commonly used antibiotic resistance genes. Engineering genetically modified (GM) crops without the use of antibiotic resistance genes should eliminate potential risk of their transfer to the environment or gut microbes. Therefore, betaine aldehyde dehydrogenase (BADH) gene from spinach is used herein as a selectable marker (Daniell et al. 2000). The selection process involves conversion of toxic betaine aldehyde (BA) by the chloroplast BADH enzyme to nontoxic glycine betaine, which also serves as an osmoprotectant. Chloroplast transformation efficiency was 25 fold higher in BA selection than spectinomycin, in addition to rapid regeneration (Table 1). Transgenic shoots appeared within 12 days in 80% of leaf discs (up to 23 shoots per disc) in BA selection compared to 45 days in 15% of discs (1 or 2 shoots per disc) on spectinomycin selection as show in FIG. 11. Southern blots confirm stable integration of foreign genes into all of the chloroplast genomes (~10,000 copies per cell) resulting in homoplasmy. Transgenic tobacco plants showed 1527-1816% higher BADH activity at different developmental stages than untransformed controls. Transgenic plants were morpho-logically indistinguishable from untransformed plants and the introduced trait was stably inherited in the subsequent generation. This is the first report of genetic engineering of the chloroplast genome without the use of antibiotic selection. Use of genes that are naturally present in spinach for selection, in addition to gene containment, should ease public concerns or perception of GM crops. Also, this should be very helpful in the development of edible insulin.

Polymer-proinsulin Recombinant DNA Vectors: First we developed independent chloroplast vectors for expression of insulin chains A and B as polymer fusion peptides, as it has been produced in $E.\ coli$ for commercial purposes in the past. The disadvantage of this method is that $E.\ coli$ does not form disulfide bridges in the cell unless the protein is targeted to the periplasm. Expensive in vitro assembly after purification is necessary for this approach. Therefore, a better approach is to express the human proinsulin as a polymer fusion protein. This method is better because chloroplasts are capable of forming disulfide bridges. Using a single gene, as opposed to the individual chains, eliminates the necessity of conducting two parallel vector construction processes, as is needed for individual chains. In addition, the need for individual fermentations and purification procedures is eliminated by the single gene method. Further, proinsulin products require less processing following, extraction. Another benefit of using the proinsulin is that the C-peptide, which is an essential part the proinsulin protein, has recently been show to play a positive role in diabetic patients (Ido et al, 1997).

Recently, the human pre-proinsulin gene was obtained from Genentech, Inc. First, the pre-proinsulin was sub-cloned into pUC19 to facilitate further manipulations. The next step was to design primers to make chloroplast expression vectors. Since we are interested in proinsulin expression, the 5' primer was designed to land on the proinsulin sequence. This FW primer eluded the 69 bases or 23 coded amino acids of the leader or pre-sequence of preproinsulin. Also, the forward primer included the enzymatic cleavage site for the protease factor Xa to avoid the use of cyanogen bromide. Besides the Xa-factor, a Smal site was introduced to facilitate subsequent subcloning. The order of the FW primer sequence is Smal-Xa-factor-Proinsulin gene. The reverse primer includes BamHl and Xbal sites, plus a short sequence with homology with the pUC19 sequence following the proinsulin gene. The 297 bp PCR product (Xa Pris) includes three restriction sites, which are the Smal site at the 5'-end and Xbal/BamHl sites at the 3' end of the proinsulin gene. The Xa-Pris was cloned into pCR2.1 resulting in pCR2.1-Xa-Pris (4.2 kb). Insertion of Xa-Pris into the multiple cloning site of pCR2.1, resulted in additional flanking restriction enzyme sites that will be used in subsequent sub-cloning steps. A GVGVP (SEQ ID NO. 20) 50-mer was generated as described previously (Daniell et al. 1997). The ribo some binding sequence was introduced by digesting pUCs-10, which contains the RBS sequence GAAGGAG (SEQ ID NO. 23), with Nool and Hind III flanking sites. The plasmid pUC19-50 was also digested with the same enzymes. The 50 mer gene was eluted from the gel and ligated to pUCs-10 to produce pUCs-10-50 mer. The ligation step inserted into the 50 mer gene a RBS sequence and a Smal site outside the gene to facilitate subsequent fusion to proinsulin.

Figure 2A:
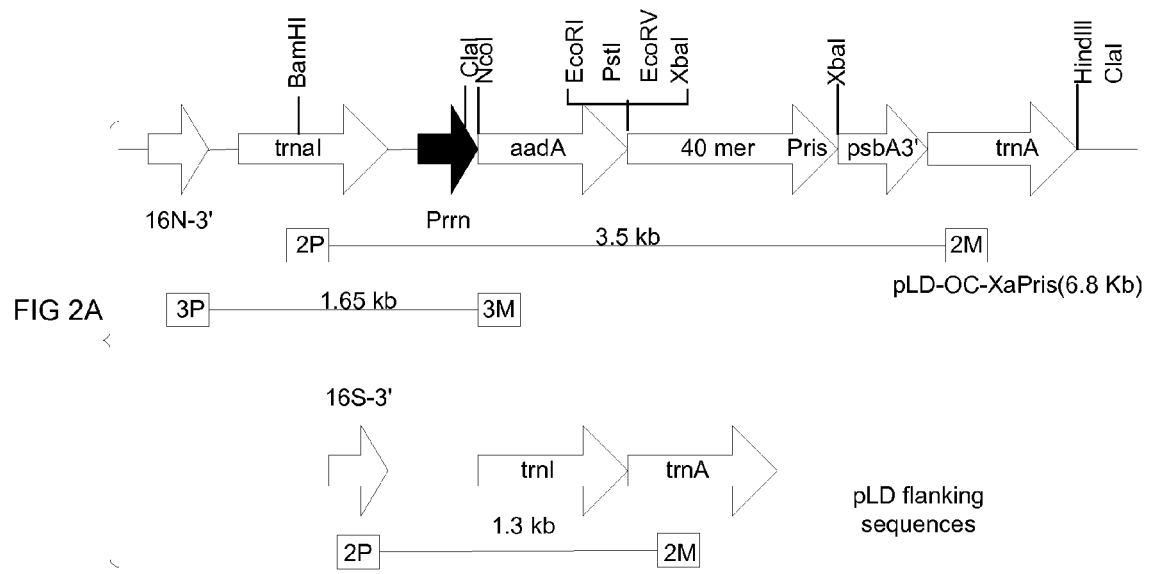

Another Smal partial digestion was performed to eliminate the stop codon of the biopolymer, transform the 50 mer to a 40 mer, and fuse the 40 mer to the Xa-proinsulin sequence. The conditions for this partial digestion needed a decrease in DNA concentration and the 1:15 dilution of Smal. Once the correct fragment was obtained by the partial digestion of Smal (eliminating the stop codon but include the RBS site), it was ligated to the Xa-proinsulin fusion gene resulting in the construct pCR2.1-40-XaPris. Finally, the biopolymer (40 mer)-proinsulin fusion gene was subcloned into pSBL-CtV2. and the final vector was called pSBL-OC-XaPris. The orientation of the insert was checked with NooI: one the five colonies chosen had the correct orientation of the gene. The fusion gene was also subcloned into pLD-CtV vector and the orientation was checked with EooRl and Pvuil. One of the four colonies had the correct orientation of the insert. This vector was called pLD-OC-XaPris (FIG. 2A).

Both chloroplast vectors contain the 16S rNA promoter (Prm) driving the selectable marker gene aadA (aminoglycoside adenyl transferase conferring resistance to spectinomycin) followed by the psbA 3' region (the terminator from a gene coding for photosystem II reaction center components) from the tobacco chloroplast genome. The only difference between these two chloroplast vectors (pSBL and pLD) is the origin of DNA fragments. Both pSBL and pLD are universal chloroplast expression/integration vectors and can be used to transform chloroplast genomes of several other plant species (Daniell et al. 1998) because these flanking sequences are highly conserved among higher plants. The universal vector uses trnA and trnl genes (chloroplast transfer RNAs coding for Alanine and Isoleucine) from the inverted repeat region of the tobacco chloroplast genome as flanking sequences for homologous recombination as shown in FIGS. 2A and 3B. Because the universal vector integrates foreign genes within the Inverted Repeat region of the chloroplast genome, it should double the copy number of insulin genes (from 5000 to 10,000 copies per cell in tobacco). Furthermore, it has been demonstrated that homoplasmy is achieved even in the first round of selection in tobacco probably because of the presence of a chloroplast origin of replication within the flanking sequence in the universal vector (thereby providing more templates for integration). Because of these and several other reasons, foreign gene expression was shown to be much higher when the universal vector was used instead of the tobacco specific vector (Guda et al., 2000).

DNA sequence of the polymer-proinsulin fusion was determined to confirm the correct orientation of genes, in frame fusion and lack of stop codons in the recombinant DNA constructs. DNA sequencing was performed using a Perkin Elmer ABI prism 373 DNA sequencing system using a ABI Prism Dye Termination Cycle Sequencing Kit. The kit uses AmpliTaq DNA polymerase. Insertion sites at both ends were sequenced using primers for each strand. Expression of all chloroplast vectors was first tested in $E.$ $coli$ before their use in tobacco transformation because of the similarity of protein synthetic machinery (Brisey et al. 1997). For $Escherichia$ $coli$ expression XL-1 Blue strain was used. $E.$ $coli$ was transformed by standard $CaCl_2$ transformation procedures.

Expression and Purification of the Biopolymer-proinsulin fusion protein: Terrific broth growth medium was inoculated with 40 µl of Ampicillin (100 mg/ml) and 40 µl of the XL-1 Blue MRF To strain of $E.$ $coli$ containing pSBL-OC-XaPris plasmid. Similar inoculations were made for pLD-OC-XaPris and the negative controls, which included both plasmids containing the gene in the reverse orientation and the $E.$ $coli$ strain without any plasmid. Then, 24 hr cultures were centrifuged at 13,000 rpm for 3 min. The pellets were resuspended in 500 µl of autoclaved $dH_2O$ and transferred to 6 ml Falcon tubes. The resuspended pellet was sonicated, using a High Intensity Ultrasonic processor, for 15 sec at an amplitude of 40 and then 15 sec on ice to extract the fusion protein from cells. This sonication cycle was repeated 15 times. The sonicated samples were transferred to microcentrifuge tubes and centrifuged at 4° C. at 10,000 g for 10 min to purify the fusion protein. After centrifugation, the supernatant were transferred to microcentrifudge tubes and an equal volume of 2×TN buffer (100 mM Tris HCI, pH 8, 100 mM NaCl) was added. Tubes were warmed at 42° C. for 25 min to induce biopolymer aggregation. Then the fusion protein was recovered by centrifuging at 2,500 rpm at 42° C. for 3 min. The recovered fusion protein was resuspended in 100 µl of cold water. The purification process was repeated twice. Also, the fusion protein was recovered by using 6M Guanidine hydrochloride phosphate buffer, pH 7.0 (instead of water), to facilitate stability of insulin. New cultures were incubated for this step following the same procedure as described above, except that the pSBL-OC-XaPris expressing cells were incubated for 24, 48, and 72 hrs. Cultures were centrifuged at 4,000 rpm for 12 min and the pellet was resuspended in 6M Guanidine hydrochloride phosphate buffer, pH 7.0, and then sonicated as described above. After sonication, samples were run in a 16.5% Tricine gel, transferred to the nitrocellulose membrane, and immunoblotting was performed the following day.

A 15% glycine gel was run for 6 h at recommended voltage as shown in FIG. 1. Two different methods of extraction were used. It was observed that when the sonic extract is in 6M Guanicine Hydrochloride Phosphate Buffer, pH 7.0, the molecular weight changes from its original and correct MW 24 kD to a higher MW of approximately 30 kDa (FIG. 1C. I). This is probably due to the conformation that the biopolymer takes under this kind of buffer, which is used to maximize the extraction of proinsulin.

Figure 1C:
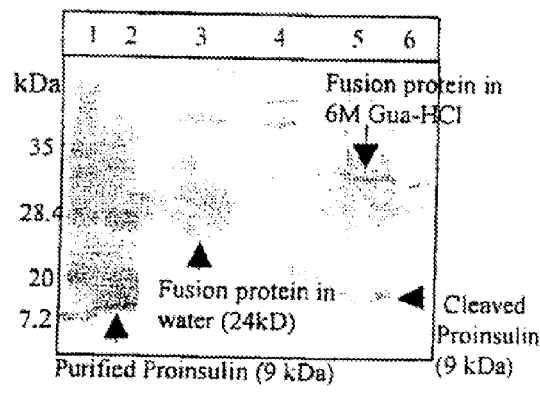
Figure 1D:
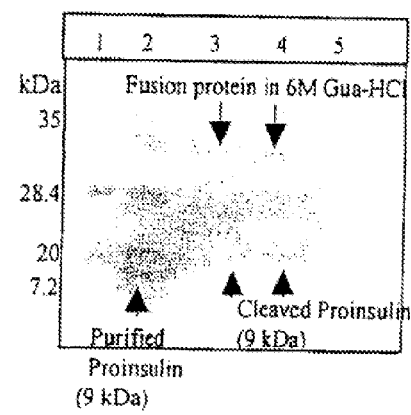

The gel was first stained with 0.3M $CuCl_2$ and then the same gel was stained with Commassie R-250 Staining Solution for an hour and then destained for 15 min first, and then overnight. $CuCl_2$ creates a negative stain (Lee et al. 1987). Polymer proteins (without fusion) appear as clear bands against a blue background in color or dark against a light semiopaque background (FIG. 1A). This stain was used because other protein stains such as Coomassie Blue R250 does not stain the polymer protein due to the lack of aromatic side chains (McPherson et al. 1992). Therefore, the observation of the 24 kDa protein in the R250 stained gel (FIG. 1B) is due to the insulin fusion with the polymer. This observation was further confirmed by probing these blots with the anti-human proinsulin antibody. As anticipated, the polymer insulin fusion protein was observed in western blots as shown in FIG. 1C, even though the binding of antibody was less efficient (probably due to concealment of insulin epitopes by the polymer). Larger proteins observed as shown in FIG. 1C II are tetramer and hexamer complexes of proinsulin.

It is evident that the insulin-polymer fusion proteins are stable in $E.$ $coli$. Confirming this observation, recently another lab has shown that the PBP polymer protein conjugates (with thioredoxin and tendamistat) undergo thermally reversible phase transition, retaining the transition behavior of the free polymer (Meyer and Chikoti, 1999). These results clearly demonstrate that insulin fusion has not affected the inverse temperature transition property of the polymer. One of the concerns is the stability of insulin at temperatures used for thermally reversible purification. Temperature induced production of human insulin has been in commercial use (Schmidt et al. 1999). Also, the temperature transition can be lowered by increasing the ionic strength of the solution during purification of this PSP (McPherson et al, 1996). Thus, GVGVP-fusion could be used to purify a multitude of economically important proteins in a simple inexpensive step.

XL-1 Blue strain of $E.$ $coli$ containing pLD-OC-XaPris and the negative controls, which included a plasmid containing the gene in the reverse orientation and the $E.$ $coli$ strain without any plasmid were grown in TB broth. Cell pellets were resuspended in 500 µl of aytoclaved $dH_2O$ or 6M Guanidine hydrochloride phosphate buffer, pH 7.0 were sonicated and centrifuged at 4° C. at 10,000 g for 10 min. After centrifugation, the supernatants were mixed with and equal volume of 2×TN buffer (100 mM Tris-HCl, pH 8, 100 mM NaCl). Tubes were warmed at 42° C. for 25 min to induce biopolymer aggregation. Then fusion protein was recovered by centrifuging at 2,500 rpm at 42° C. for 3 min. Samples were run in a 16.5% Tricine gel, transferred to the nitrocellulose membrane, and immunoblotting was performed. When the sonic extract is in 6M Guanidine Hydrochloride Phosphate Buffer, pH 7.0, the molecular weight changes from its original and correct MW to a higher MW of approximately 30 kDa as shown in FIGS. 12A and B. This probably due to the conformation of the biopolymer in this buffer.

The gel was first stained with 0.3M $CuCl_2$ and then the same gel was stained with Commassie R-250 Staining Solution for an hour and then destained for 15 min first, and then overnight. $CuCl_2$ creates a negative stain (Lee et al. 1987). Polymer proteins (without fusion) appear as clear banks against a blue background in color or dark against a light semiopaque background as shown in FIG. 12A. The stain was used because other protein stains such as Coomassie Blue R250 does not stain the polymer protein due to the lack of aromatic side chains (McPherson et al., 1992). Therefore, the observation of the 24 kDa protein in R250 stained gel as shown in FIG. 12B is due to the insulin fusion with the polymer. This observation was further confirmed by probing these blots with the anti-human proinsulin antibody. As anticipated, the polymer insulin fusion protein was observed in western blots as shown in FIGS. 13A and B. Larger proteins observed in FIGS. 13A-C are tetramer and hexamer complexes of proinsulin. It is evident that the insulin-polymer fusion proteins are stable in E. coli. Confirming this observation, recently others have shown that the PBP polymer protein conjugates (with thioredoxin and tendamistat) undergo thermally reversible phase transition, retaining the transition behavior of the free polymer (Meyer and Chilkoti, 1999). These results clearly demonstrate that insulin fusion has not affected the inverse temperature transition property of the polymer. One of the concerns is the stability of insulin at temperatures used for thermally reversible purification. Temperature induced production of human insulin has been in commercial use (Schmidt et al. 1999). Also, the temperature transition can be lowered by increasing the ionic strength of the solution during purification of this PBP (McPherson et al. 1996). Thus, GVGVP-fusion could be used to purify a multitude of economically important proteins in a simple inexpensive step.

Figure 2B:
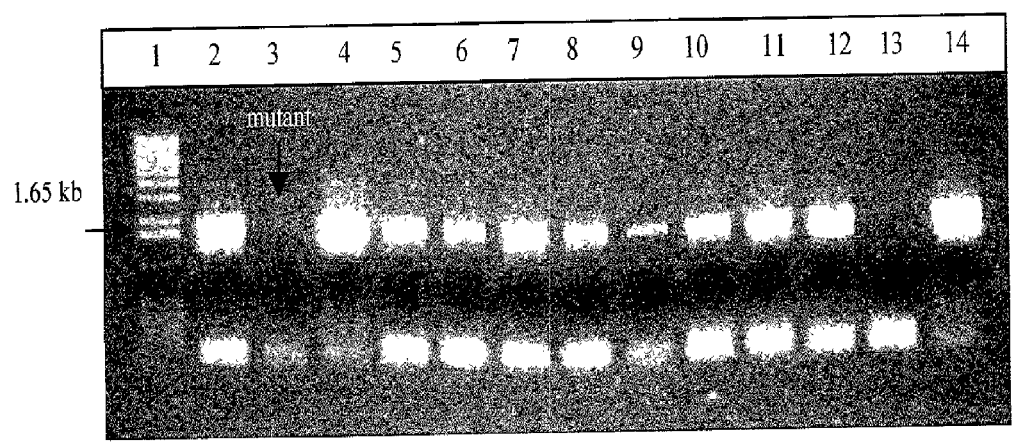
Figure 2C:
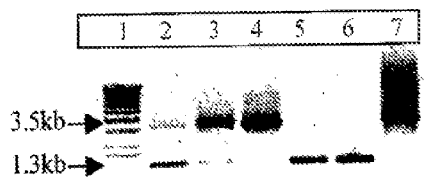
Figure 2D:
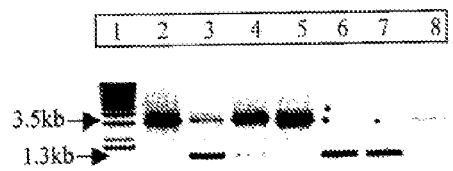

Biopolymer-proinsulin fusion gene expression in chloroplast: As described in section d, pSBL-OC-R40XaPris vector and pLD-OC-R40XaPris vectors were bombarded into the tobacco chloroplasts genome via particle bombardment (Daniell, 1997). PCR was performed to confirm biopolymer-proinsulin fusion gene integration into chloroplast genome. The PCR products were examined in 0.8% agarose gels. FIG. 2A shows primers landing sites and expected PCR products. FIG. 2B shows the 1.6 kbp PCR product, confirming integration of the aadA gene into the chloroplast genome. This 1.6 kb product is seen in all clones except L9, which is a mutant. We used primers 2P and 2M to confirm integration of both the aadA and biopolymer-proinsulin fusion gene. The 1.3 kbp product corresponds to the native chloroplast fragment and the 3.5 kbp product corresponds to the chloroplast genome that has integrated all three genes as shown in FIGS. 2C and D. All the clones examined at this time show heteroplasmy, exce[t c;pmes :8d om Fog/2C, and S41b in FIG. 2D, which show almost homoplasmy.

Figure 14:
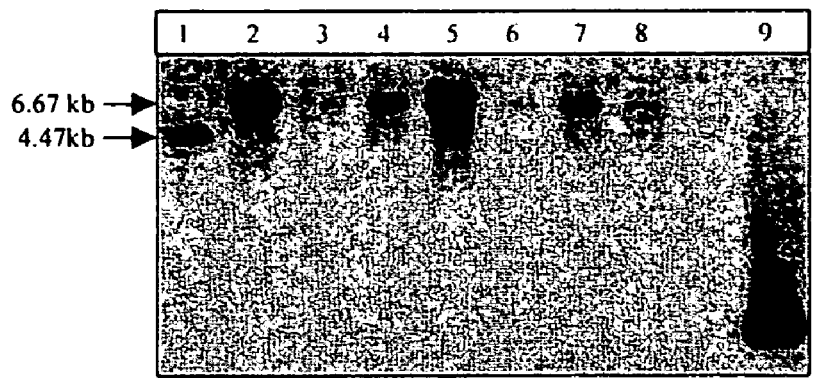
Figures 15A, 15B, 15C:
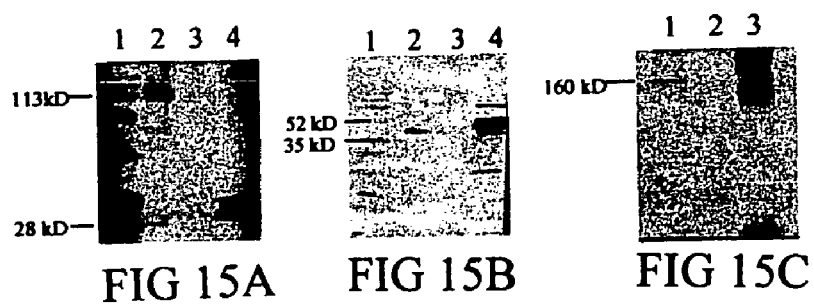

As described in section d, chloroplast-vector was bombarded into the tobacco chloroplast genome via particle bombardment (Daniell, 1997). PCR and Southern Blots were performed to confirm biopolymer-proinsulin fusion gene integration into chloroplast genome. Southern blots show homoplasmy in most $T_0$ lines but a few showed some heteroplasmy as shown in FIG. 14. Western blots show the expression of polymer proinsulin fusion protein in all transgenic lines in FIG. 13C. Quantification is by ELISA.

Protease Xa Digestion of the Biopolymer-proinsulin fusion protein and Purification of Proinsulin: Factor Xa was purchased from New England Biolabs at a concentration of 1.0 mg/ml. The Factor Xa is supplied in 20 mM HEPES, 500 mM, NaCl, 2 mM $CaCl_2$, 50% glycerol, (pH 8.0). The reaction was carried out in a 1:1 ratio of fusion protein to reaction buffer. The reaction buffer was made with 20 mM Tris-HCl, 100 mM NaCl, 2 mM $CaCl_2$, (pH 8.0). The enzymatic cleavage of the fusion protein to release the proinsulin protein from the $(GVGVP)_{40}$ (SEQ ID NO. 24) was initiated by adding the protease to the purified fusion protein at a ration (ww) of approximately 1,500. This digestion was continued for 5 days with mild stirring at 4.degree. C. Cleavage of the fusion protein was monitored by SDS-PAGE analysis. After the cleavage, the same conditions are used for purification of the proinsulin protein. The purification steps are the same as for the purification of the fusion protein, expect that instead of recovering the pellet, the supernatant is saved. We detected cleaved proinsulin in the extracts isolated in 6M guanidine hydrochloride buffer as shown in FIG. 1C 11. Conditions can be estimized for complete cleavage. The Xa protease has been successfully used to cleave $(GVGVP)_{20}$ (SEQ ID NO. 25)-GST fusion (McPherson et al. 1992). Therefore, cleavage of proinsulin from GVGVP using the Xa protease does not pose problems.

The enzymatic cleavage of the fusion protein to release the proinsulin protein from the $(GVGVP)_{40}$ (SEQ ID NO. 24) was initiated by adding the factor 10A protease to the purified fusion at a ratio (w/w) of approximately 1:500. Cleavage of the fusion protein was monitored by SDS-PAGE analysis. We detected cleaved proinsulin in the extracts isolated in 6M guanidine hydrochloride buffer as shown in FIGS. 13A and B. Conditions are noweing optimized for complete coverage. The Xa protease has been successfully used previously to cleave $(GVGVP)_{20}$ (SEQ ID NO. 25)-GST fusion (McPherson et al. 1992).

Evaluation of chloroplast gene expression: (1577-P-00) A systematic approach to identify and overcome potential limitations of foreign gene expression in chloroplasts of transgenic plants is essential. Information gained herein increases the utility of choloroplast transformation system by scientists interested in expressing other foreign proteins. Therefore, it is important to systematically analyze transcription, RNA abundance, RNA stability, rate of protein synthesis and degradation, proper folding and biological activity. For example, the rate of transcription of the introduced insulin gene may be compared with the highly expressing endogenous chloroplast genes (rbcL, psbA, 16S rRNA), using run on transcription assays to determine if the 16SrRNA promoter is operating as expected. Transgenic chloroplast containing each of the three constructs with different 5' regions is investigated to test their transcription efficiency. Similarly, trasgene RNA levels is monitored by northerns, dot blots and primer extension relative to endogenous rbcL, 16S rRNA, or psbA. These results along with run on transcription assays should provide valuable information of RNA stability, processing, etc. With out past experience in expression of several foreign genes, foreign transcripts appear to be extremely stable based on northern blot analysis. However, a systematic study is valuable to advance utility of his system by other scientists.

Importantly, the efficiency of translation may be tested in isolated chloroplasts and compared with the highly translated chloroplast protein (psbA). Pulse chase experiments help assess if translational pausing, premature termination occurs. Evaluation of percent RNA loaded on polysomes or in constructs with or without 5'UTRs helps determine the efficiency of the ribosome binding site and 5' stem-loop translational enhancers. Codon optimized genes are also compared with unmodified genes to investigate the rate of translation, pausing and termination. In our recent experience, we observed a 200-fold difference in accumulation of foreign proteins due to decreases in proteolysis conferred by a putative chaperonin (De Cosa et al. 2001). Therefore, proteins from constructs expressing or not expressing the putative chaperonin (with or without ORF1+2) provide valuable information on protein stability. Thus, all of this information may be used to improve the next generation of chloroplast vectors.

Vector for CTB expression in chloroplasts: The leaser sequence (63 bp) of the native CTB gene (372 bp) was deleted and a start codon (ATG) introduced at the 5' end of the remaining CTB gene (309 bp). Primers were designed to introduce a rbs site 5 bases upstream of the start codon. The 5' primer (38 mer) was designed to an on the start codon and the 5'-end of the CTB gene. This primer had an XbaI site at the 5'-end, the rbs site [GGAGG], a 5 bp breathing space followed by the first 20 bp of the CTB gene. The 3' primer (32 mer) was designed to land on the 3' end of the CTB gene and it introduced restriction sites at the 3' end to facilitate subcloning. The 347 bp rCTB PCT product was subcloned into pCR2.1 resulting in pcCR2.1-rCTB. The final step was insertion of rCTB into the XbaI site of the universal or tobacco vector (pLB-CtV2) that allows the expression of the construct in *E. coli* and chloroplasts. Restriction enzyme digestion of the pLD-LH-rCTB vector with BamHI was performed to confirm the correct orientation of the inserted fragment in the vector.

Because of similarity of protein synthetic machinery, expression of the chloroplast vector was test in *E. coli* before its use in tobacco transformation. For *Escherichia coli* expression the XL-1 Blue $MRF_{TO}$ strain was used. *E. coli* was transformed by standard $CaCl_2$ transformation procedures. Transformed *E. coli* (24 hrs culture and 48 hrs culture in 100 ml TB with 100 mg/ml ampicillin) and untransformed *E. coli* (24 hrs culture and 48 hrs culture in 100 ml TB with 12.5 mg/ml tetracycline) was then centrifuged at 10000×g in a Beckman G-15R centrifuge for 15 min. The pellet was washed with 200 mM Tris-Cl twice and resuspended in 500 µl extraction buffer 200 mM Tris-Cl, pH 8.0, 100 mM NaCal; 10 mM EDTA, 2 mM PMSF) and then sonicated using Autotune Series High Intensity Ultrasonic Processor. Then, 100 µl aliquots of the sonicated transformed and untransformed cells [containing 50-100 µg of crude protein extract as determined by Bradford protein assay (Bio-Rad Inc)] and purified CTB (Sigma C-9903) were boiled with 2×SDS sample buffer and separated on a 15% SDS-PAGE gel in Tris-glycine buffer (25 mM Tris, 250 mM glycine, pH 8.3, 0.1% SDS). The separated protein was then transferred to a nitrocellulose membrane by electro blotting using the Trans-Blot Electrophoretic Transfer Cell (Bio-Rad Inc.).

Imunoblot detection of CTB expression in *E. coli*: Non-specific antibody reactions were blocked by incubation of the membrane in 25 ml of 5% non-fat dry milk in TBS buffer for 1-3 hrs on a rotary shaker (40 rpm), followed by washing in TBS buffer for 5 min. The membrane was then incubated for an hour with gentle agitation in 30 ml of a 1:5000 dilution of rabbit anti-cholera antiserum (Sigma C-3062) in TBS with Tween-20 [TBST] (containing 1% non-fat dry milk) followed by washing 3 times in TBST buffer. The membrane was incubated for an hour at room temperature with gentle agitation in 30 ml of a 1:10000 dilution of mouse anti-rabbit 1 gG conjugated with alkaline phosphate in TBST. It was then washed thrice with TBST and once with TBS followed by incubation in the Alkaline Phosphate Color Development Reagents, BCIP/NBT in AP color development Buffer (Bio-Rad, Inc.) for an hour. Immunoblot analysis snows the presence of 11.5 kDa polypeptide for purified bacterial CTB and transformed 24 h/48 h cultures (FIG. 3A, lanes 2, 3 and 5). The $48^{th}$ culture appears to express more CTB than that of the 24 h culture indicating the accumulation of the CTB protein over time. The purified bacterial CTB (45 Kda) dissociated into monomers (11.5 KDa each) due to boiling prior to SDS PAGE. These results indicate that the pLD-LH-CTB vector is expressed in *E. coli*. Because of the similarity of the *E. coli* protein synthetic machinery to that of chloroplasts, chloroplast expression of the above vector should be possible.

CTB expression in chloroplasts: As described below, pLD-LH-CTB was integrated into the tobacco chloroplast genome via particle bombardment (Daniell, 1997). PCR analysis was performed to confirm chloroplast integration. FIG. 3B shows primer landing sites and size of expected products. PCR analysis of clones obtained after the first round of selection was carried out as described below. PCR products were examined on 0.8% agarose gels. The PCR results (FIG. 3C) show that clones 1 and 5 that do not show any product are mutants while clones 2, 3, 4, 6, 7, 8, 9, 10 and 11 that gave a 1.65 kbp product are transgenic. As expected lanes 13-15 did not give any PCR product, confirming that the PCR reaction was not contaminated. Because primers 3P & 3M land on the aadA gene and on the chloroplast genome, all clones that show PCR products have integrated the CTB gene and the selectable marker into the chloroplast genome. Clones that showed chloroplast integration of the CTB gene were moved to the second round of selection to increase copy number. PCR analysis of clones obtained after the second round of selection was also carried out. PCR results shown in FIG. 3D indicate that clone 5 does not give a 3 kbp product indicating that it is a mutant as observed earlier. Other clones give strong 3 kbp product and a faint 1.3 kbp (similar to the 1.3 kbp untransformed plant product), indicating that they are transgenic but not yet homoplasmic. Complete homoplasmy can be accomplished by several more rounds of selection or by germinating seeds from transgenic plants on 500 µg/ml of spectinomycin.

Vector constructions: pLD vector is used for all the constructs. This vector was developed for chloroplast transformation. It contains the 16S rRNA promoter (Prm) driving the selectable marker gene aadA (aminoglycoside adenyl transferase conferring resistance to spectinomycin) followed by multiple cloning site and then the psbA 3' region (the terminator from a gene coding for photosystem II reaction center components) from the tobacco chloroplast genome. The pLD vector is a universal chloroplast expression/integration vector and can be used to transform chloroplast genomes of several other plant species (Daniell et al. 1998, Daniell 1999) because these flanking sequences are highly conserved among higher plants. The universal vector uses trnA and trnI genes (chloroplast transfer RNAs coding for Alanine and Isoleucine) from the inverted repeat region of the tobacco chloroplast genome as flanking sequences for homologous recombination. Because the universal vector integrates foreign genes within the Inverted Repeat region of the chloroplast genome, it should double the copy number of the transgene (from 5000 to 10,000 copies per cell in tobacco). Furthermore, it has been demonstrated that homoplasmy is achieved even in the first round of selection in tobacco probably because of the presence of a chloroplast origin of replication within the flanking sequence in the universal vector (thereby providing more templates for integration). These, and several other reasons, foreign gene expression was shown to be much higher when the universal vector was used instead of the tobacco specific vector (Guda et al. 2000).

CTB-Proinsulin Vector Construction: The chloroplast expression vector pLD-CTB-Proins was constructed as follows. First, both proinsulin and cholera toxin B-subunit genes were amplified from suitable DNA using primer sequences. Primer 1 contains the GGAGG chloroplast preferred ribosome binding site five nucleotides upstream of the start codon (ATG) for the CTB gene and a suitable restriction enzyme site (Spel) for insertion into the chloroplast vector. Primer 2 eliminates the stop codon and adds the first two amino acids of a flexible hinge tetrapeptide GPGP as reported by Begerot et al. (1997), in order to facilitate folding of the CTB-proinsulin fusion protein. Primer 3 adds the remaining two amino acids for the hinge tetrapeptide and eliminates the presequence of the pre-proinsulin. Primer 4 adds a suitable restriction site (Spel) for subcloning into the chloroplast vector. Amplified PCR products were inserted into the TA cloning vector. Both the CTB and proinsulin PCR fragments were excised at the Smal and Xbal restriction sites. Eluted fragments were ligated into the TA cloning vector. Interestingly, all white colonies showed the wrong orientation for CTB insert while three of the five blue colonies examined showed the right orientation of the CTB insert. The CTB-proinsulin fragment was excised at the EcoRl sites and inserted into EcoRl digested dephosphorolated pLD vector. Resultant onicroplast integration expression vector, pLD-CTB-Prions will be tested for expression in *E. coli* by western blots. After confirmation of expression of CTB-proinsulin fusion in *E. coli*, pLD-CTB-Prions will be bombarded into tobacco cells as described below.

The following vectors may be designed to optimize protein expression, purification and production of proteins with the same amino acid composition as in human insulin.

a) Using tobacco plants, Eibl (1999) demonstrated, in vivo, the differences in translation efficiency and mRNA stability of a GUS reporter gene due to various 5' and 3' untranslated regions (UTR's). This already described systematic transcription and translation analysis can be used in a practical endeavor of insulin production. Consistent with Eibl's (1999) data for increased translation efficiency and mRNA stability, the psbA 5' UTR can be used in addition with the psbA 3' UTR already in use. The 200 bp tobacco chloroplast DNA fragment containing 5' psbA UTR may be amplified by PCR using tobacco chloroplast DNA as template. This fragment may be cloned directly in the pLD vector multiple cloning site downstream of the promoter and the aadA gene. The cloned sequence may be exactly the same as in the psbA gene. (Update "Human Insulin") We have cloned the 5' untranslated region of the tobacco psbA gene including the promoter (5'UTR), shown in FIG. 32. We performed PCR using the primers CCGTCGACGTAGAGAAGTCCGTATT (SEQ ID NO:4) and GCCCATGGTAAAATCTTGGTTTATTTA (SEQ ID NO:5), which resulted in a 200 base pair product, as expected. We inserted this PCR product into a TA cloning vector. Since restriction enzyme sites were not available to subclone the 5'UTR immediately upstream of the gene coding for the CTB-proinsulin fusion protein, we used the "SOEing" PCR technique to create the DNA sequence with the 5'UTR immediately upstream of the CTB-proinsulin gene (FIG. 25). The products of this PCR include both the 5'UTR (200bp) and the gene for CTB-proinsulin (5CP) at 800 bp. 5CP was eluted and then inserted into the TA cloning vector where DNA sequencing was performed to confirm accuracy of nucleotide sequence before it was subcloned into the pLD vector.

b) Another approach of protein production in chloroplasts involves potential insulin crystallization for facilitating purification. The cry2Aa2 *Bacillus thuringiensis* operon derived putative chaperonin may be used. Expression of the cry2Aa2 operon in chloroplasts provides a model system for hyper-expression of foreign proteins (46% of total soluble protein) in a folded configuration enhancing their stability and facilitating purification (De Cosa et al. 2001). This justifies inclusion of the putative chaperonin from the cry2Aa2 operon in one of the newly designed constructs. In this region there are two open reading frames (ORF 1 and ORF2) and a ribosomal binding site (rbs). This sequence contains elements necessary for Cry2Aa2 crystallization, which help to crystallize insulin and aid in subsequent purification. Successful crystallization of other proteins using this putative chaperonin has been demonstrated (Ge et al. 1998). The ORF 1 AND ORF2 of the Bt Cry2Aa2 operon may be amplified by PCR using the complete operon as a template. Subsequent cloning, using a novel PCR technique, allows for direct fusion of this sequence immediately upstream of the proinsulin fusion protein without altering the nucleotide sequence, which is normally necessary to provide a restriction enzyme site (Horton et al. 1988).

(Update "Human Insulin") Another parameter of foreign protein production to be investigated is post-translational. The DNA for the putative chaperonin in the *Bacillus thuringiensis* Cry 2A2 operon encodes a protein that could potentially fold and crystallize CTB-Proinsulin, which would allow it to accumulate in large quantities protected from chloroplast proteases and facilitate in subsequent purification. Standard molecular biology techniques were used to insert this DNA fragment immediately upstream of the 5'UTR of the construct containing the chloroplast optimized proinsulin. Additionally, another vector was constructed to contain only Shine-Dalgarno sequence (GGAGG) followed by the sequence encoding for the Cholera toxin B subunit and synthetic chloroplast optimized proinsulin fusion (CTB-PTpris). This construct will allow us to determine the value of the proinsulin sequence modification both with and without the 5'UTR.

c) To address codon optimization the proinsulin gene may be subjected to certain modifications in subsequent constructs. The plastid modified proinsulin (PtPris) can have its nucleotide sequence modified such that the codons are optimized for plastid expression, yet its amino acid sequence remains identical to human proinsulin. PtPris is an ideal substitute for human proinsulin in the CTB fusion peptide. The expression of the construct can be compared to the native human proinsulin to determine the affects to codon optimization, which serve to address one relevant mechanistic parameter of translation. Analysis of human proinsulin gene showed that 48 of its 87 codons were the lowest frequency codons in the chloroplast for the amino acid for which they encode. For example, there are six different codes for leucine, Their frequency within the chloroplast genome ranges from 7.3 to 30.8 thousand codons. There are 12 leucines in proinsulin, 8 have the lowest frequency codons (7.3), and none code for the highest frequency codons (30.8). In the plastid, optimized proinsulin gene all the codons code for the most frequent, whereas in human proinsulin over half of the codos are the least frequent. Human proinsulin nucleotide sequence contains 62% C+G, whereas plastid optimized proinsulin gene contain 24% C+G. Generally, lower C+G content of foreign genes correlates with higher levels of expression (Table 2).

(Update "Human Insulin") Chloroplast foreign gene expression correlates well with % AT of the gene coding sequence. The native human proinsulin sequence is 38% AT, while the newly synthesized chloroplast optimized proinsulin is 64% AT. We determined the optimal chloroplast coding sequence for the proinsulin (PTpris) gene by using a codon composition that is equivalent to the highest translated chloroplast gene, psbA. The preferred codon composition of the psbA in tobacco is conserved within 20 vascular plant species. We have compared it to the native human proinsulin DNA sequence (FIG. 27). Since there are too many changes for conventional mutagenesis, we employed the Recursive PCR method for total gene synthesis. FIG. 28 shows the product of this gene synthesis corresponding to the 280 bp expected size. This product, PTpris, was then used as a template with CTB and 5'UTR to create a fusion of these sequences using the SOEing PCR technique. The products of this reaction can be seen in FIG. 29. These include 5'UTR (200 bp), CTB (320 bp), Proinsulin (280 bp), and CTB-Proinsulin (600 bp) as side products, and also the desired 5'UTR CTB-PTpris (5CPTP) AT 800 BP. This was then inserted into the TA cloning vector where the sequence was verified before being subcloned into the pLD vector.

d) Another version of the proinsulin gene, mini-proinsulin (Mpris), may also have its codons optimized for plastid expression, and its amino aid sequence does not differ from human proinsulin (Pris). Pris' sequence is B Chain-RR-C Chain-KR-A Chain, whereas Mpris' sequence is B Chain-KR-A Chain. The MPris sequence excludes the RR-C Chain, which is normally excised in proinsulin maturation to insulin. The C chain of proinsulin is an unnecessary part of in vitro production of insulin. Proinsulin folds properly and forms of the appropriate disulfide bonds in the absence of the C chain. The remaining KR motif that exists between the B chain and the A chain in MPris allows for mature insulin production upon cleavage with trypsin and carboxypeptidase B. This construct may be used for out biopolymer fusion protein. It=s codon optimization and amino acid sequence is ideal for mature insulin production.

e) Our current human proinsulin-biopolymer fusion protein contains a facor Xa proteolytic cut site, which serves as a cleavage point between the biopolymer and the proinsulin. Currently, cleavage of the polymer-proinsulin fusion protein with the factor Xa has been inefficient in out hands. Therefore, we replace this cut site with a trypsin cut site. This eliminates the need for the expensive factor Xa in processing proinsulin. Since proinsulin is currently processed by trypsin in the formation of mature insulin, insulin maturation and fusion peptide cleavage can be achieved in a single step with trypsin and carboxypeptidase B.

f) We observed incomplete translation products in plastids when we expressed the 120 mer gene (Guda et al. 2000). Therefore, while expressing the polymer-proinsulin fusion protein, we decreased the length of the polymer protein to 40 mer, without losing the thermal responsive property. In addition, optimal codons for glycine (GGT) and valine (GTA), which constitute 80% of the total amino acids of the polymer, have been used. In all nuclear encoded genes, glycine makes up 147/1000 amino acids while in tobacco chloroplsts it is 129/1000. Highly expressing genes like psbA and rbcL of tobacco make up 192 and 190 gly/1000. Therefore, glycine may not be a limiting factor. Nuclear genes use 52/1000 proline as opposed to 42/1000 in chloroplasts. However, currently used codon for praline (CCG) can be modified to CCA or CCT to further enhance translation. It is known that pathways for proline and valine are compartmentalized in chloroplasts (Guda et al. 2000). Also, proline is known to accumulate in chloroplasts as an osmoprotectant (Daniell et al. 1994).

g) Codon comparison of the CTB gene with the psbA, showed 47% homology with the most frequent codons of the psbA gene. Codon analysis showed that 34% of the codons of CTB are complimentary to the tRNA population in the chloroplasts in comparison with 51% of psbA codons that are complimentary to the chloroplast tRNA population. Because of the high levels of CTB expression in transgenic chloroplasts (Henriques and Daniell, 2000), there will be no need to modify the CTB gene.

DNA sequence of all constructs may be determined to confirm the correct orientation of genes, in frame fusion, and accurate sequences in the recombinant DNA constructs. DNA sequencing may be performed using a Perkin Elmer ABI prism 373 DNA sequencing system using ABI Prism Dye Termination Cycle Sequencing kit. Insertion sites at both ends may be sequenced by using primers for each strand.

Expression of all chloroplast vectors are first tested in *E. coli* before their use in tobacco transformation because of the similarity of protein synthetic machinery (Brixley et al. 1997). For *Escherichia coli* expression XL-1 Blue strain was used. *E. coli* may be transformed by a standard CaCl$_2$ method.

(Update "Human Insulin") All of the resulting vectors, containing the desired constructs, were used to transform both the tobacco cultivars, Petit Havana and LAMD 605 (edible tobacco). Transformation was performed using the particle bombardment method, as described. Bombarded leaves are currently being regenerated into transgenic plants under spectinomycin selection. Several clones have begun to form shoots. The clones of Petit Havana bombarded with the initial CTB-human proinsulin construct have regenerated large enough for us to extract DNA. Extracted DNA was used as a template in PCT reaction to confirm integration of the cassette into the chloroplast genome by homologous recombination. We used two primers in this reaction, 3P and 3M. 3P anneals with the native chloroplast genome, while 3M anneals with the gene for spectinomycin resistance, aadA. The 1600 bp product of this reaction is indicative of integration of the construct into the genome (FIG. 30). This experiment demonstrated that 7 of the 11 analyzed clones were the desired chloroplast transgenic plants. Western blots are currently underway to confirm expression of various CTB-proinsulin fusion proteins in *E. coli*. Because of the similarity of chloroplast and *E. coli* protein synthetic machinery, chloroplast vectors are routinely tested in our lab before bombardment. Membranes have been immunoblotted with antibodies to both CTB and Proinsulin. Results demonstrate the presence of the desired fusion Optimization of fusion gene expression: It has been reported that foreign genes are expressed between 5% (crylAC, cryllA) and 30% (uldA) in transgenic chloroplasts (Daniell, 1999). If the expression levels if the CTB-Proinsulin or polymer-proinsulin fusion proteins are low, several approaches will be used to enhance translation of these proteins. In chloroplast, transcriptional regulation of gene expression is less important, although some modulations by light and developmental conditions are observed (Cohen and Mayfield, 1997). RNA and protein stability appear to be less important because of observation of large accumulation of foreign proteins (e.g. GUS up to 30% of total protein) and tps 1 transcripts 16,966-fold higher than the highly expressing nuclear transgenic plants. Chloroplast gene expression is regulated to a large extent at the post transcriptional level. For example, 5'UTRs are used for optional translation of chloroplast mRNAs. Shine-Delgarno (GGAGG) sequences as well as a stem-loop structure located 5' adjacent to the SD sequence are used for efficient translation. A recent study has shown that insertion of the psbA 5' UTR downstream of the 16S r RNA promoter enhanced translation of a foreign gene (GUS) hundred-fold (Eibl et al. 1999). Therefore, the 85-bp tobacco chloroplast DNA fragment (1595-1680) containing 5' psbA UTR will be amplified using the following primers (SEQ ID NOs: 6 and 7, respectively): cctttaaaaagccttccattttc-tattt, gccatggtaaaat cttggtttatta. This PCR product will be inserted downstream of the 16S rRNA promoter to enhance translation of the proinsulin fusion proteins.

Yet another approach for enhancement of translation is to optimize codon compositions of these fusion proteins. Since both fusion proteins are expressed well in *E. coli*, we expected efficient expression in chloroplasts. However, optimizing codon compositions of proinsulin and CTB genes to march the psbA gene could further enhance the level of translation. Although rbcL (RuBisCO) is the most abundant protein on earth, it is translated as frequently as the psbA gene due to the extremely high turnover rate of the psbA gene product. The psbA gene is under stronger selection for increased translation efficiency and is the most abundant thylakoid protein. In addition, codon usage in higher plant chloroplasts is biased towards the NNC codon of 2-fold degenerate groups (i.e. TTC over TTT, GAC over GAT, CAC over CAT, AAC over AAT, ATC over ATT, ATA etc.). This is in addition to a strong bias towards T at a third position of 4-fold groups. There is also a context effect that should be taken into consideration while modifying specific codons. The 2-fold degenerate sites immediately upstream from a GNN codon do not show this Bias towards NNC, (TTT GGA is preferred to TTC GGA while TTC CGT is preferred to TTT CGT TTC AGT to TTT AGT and TTC TCT to TTT TCT) (SEQ ID NO:8). In addition, highly expressed chloroplast genes use GNN more frequently than other genes. Codn preference tables known to one of ordinary skill in the art may be used optimize codon composition by comparing different species. Abundance of amino acids in chloroplasts can be taken into consideration (pathways compartmentalized in plastids as opposed to those that are imported into plastids).

As far as the biopolymer gene is concerned, we observed incomplete translation products in plastids when we expressed the 120 mer gene (Guda et al. 2000). Therefore, while expressing the polymer-proinsulin fusion protein, we decreased the length of the polymer protein to 40 mer, without losing the thermal responsive property. In addition, optimal codons for glycine (GGT) and valine (GTA), which constitute 80% of the total amino acids of the polymer, have been used. In all nuclear encoded genes glycine make up 147/1000 amino acids while in tobacco chloroplasts it is 129/1000. Highly expressing genes like psbA and rbcL of tobacco make up 192 and 190 gly/1000. Therefore, glycine may not be a limiting factor. Nuclear genes use 52/1000 proline as opposed to 42/1000 in chloroplasts. However, currently used codon for praline (CCG) can be modified to CCA or CCT to further enhance translation. It is known that pathways for praline and valine are compartmentalized in chloroplasts (Guda et al. 2000). Also praline is known to accumulate in chloroplasts as an osmoprotectant (Daniell et al 1994).

We have reported that foreign genes are expressed between 3% (cry2Aa2) and 46% (cry2Aa2 operon) in transgenic chloroplasts (Kota et al. 1999; De Cosa et al. 2001). Several approaches may be used to enhance translation of the recombinant proteins. In chloroplasts, transcriptional regulation as a bottle-neck in gene expression has been overcome by utilizing the strong constituitive promoter of the 16s rRNA (Prrn). One advantage of Prrn is that it is recognized by both the chloroplast encoded RNA polymerase and the nuclear encoded chloroplast RNA polymerase in tobacco (Allison et al. 1996). Several investigators have utilized Prrn in their studies to overcome the initial hurdle of gene expression, transcription (DeCosa et al. 2001, Eibl et al. 1999, Staub et al. 2000). RNA stability appears to be one among the least problems because of observation of excessive accumulation of foreign transcripts, at times 16,966-fold higher than the highly expressing nuclear transgenic plants (Lee et al. 2000). Also, other investigations regarding RNA stability in chloroplasts suggest that efforts for optimizing gene expression need to be addressed at the post-transcriptional level (Higgs et al. 1999, Eibl et al. 1999). Our work focuses o addressing protein expression post-transcriptionally. For example, 5' and 3' UTRs are needed for optimal translation and mRNA stability of chloroplast mRNAs (Zerges 2000). Optimal ribosomal binding sites (RBS's) as well as a stem-loop structure located 5=adjacent to the RBS are needed for efficient translation. A recent study has shown that replacement of the Shine-Delgarno (GGAGG) with the psbA 5' UTR downstream of the 16S rRNA promoter enhanced translation of a foreign gene (GUS) hundred-fold (Eibl et al. 1999). Therefore, the 200-bp tobacco chloroplast DNA fragment (1680-1480) containing 5' psbA UTR may be used. This PCR product is inserted downstream of the 16S rRNA promoter to enhance translation of the recombinant proteins.

(60/263,668) Yet another approach for enhancement of translation is to optimize codon compositions. We have compared A+T % content of all foreign genes that had been expressed in transgenic chloroplasts with the percentage of chloroplast expression. We found that higher levels of A+T always correlated with high expression levels (see Table 2). It is also potentially possible to modify chloroplast protease recognition sites while modifying codons, without affecting their biological functions. Therefore, optimizing codon compositions of insulin and polymer genes to match the psbA gene should enhance the level of translation. Although rbcL (RuBisCO) is the most abundant protein on earth, it is not translated as highly as the psbA gene due to the extremely high turnover of the psbA gene product. The psbA gene is under stronger selection for increased translation efficiency and is the most abundant thylakoid protein. In addition, the codon usage in higher plant chloroplasts is biased towards the NNC codon of 2-fold degenerate groups (i.e. TTC over TTT, GAC over GAT, CAC over CAT, AAC over AAT, ATC over ATT, ATA etc.). This is in addition to a strong bias towards T at the third position of the 4-fold degenerate groups. There is also a context effect that should be taken into consideration while modifying specific codons. The 2-fold degerate sites immediately upstream from a GNN codon do not show this bias towards NNC. (TTT GGA is preferred to TTC GGA while TTC CGT is preferred to TTT CGT, TTC AGT to TTT AGT and TTC TCT to TTT TCT, Morton, 1993; Morton and Bernadette, 2000). In addition, highly expressed chloroplast genes use GNN more frequently that other genes. The disclosure of web site http://www.kazusa.or.jp/codon and http://www.ncbi.nlm.nih.gov may be used to optimize codon composition by comparing codon usage of different plant species' genomes and PsbA=s genes. Abundance of amino acids in chloroplasts and tRNA anticodons present in chloroplast may be taken into consideration. Optimization of polymer and proinsulin may be performed using a novel PCR approach (Prodromou and Pearl, 1992; Casimiro et al. 1997), which has been successfully used in our laboratory to optimize codon composition of other human proteins.

Bombardment and Regeneration of Chloroplast Transgenic Plants: Tobacco (*Nicotiana tabacum* var. Petit Havana) and nicotine free edible tobacco (LAMD 665, gift from Dr. Keith Wycoff. Planet Biotechnology) plants are grown aseptically by germination of seeds on MSO medium. This medium contains MS salts (4.3 g/liter), B5 vitamin mixture (myoinositol, 100 mg/liter; thiamine-HCl. 10 mg/liter nicotinic acid. 1 mg/liter/pyridoxine-HCl. 1 mg/liter, sucrose (30 g/liter) and phytagar (6 g/liter) at pH 5.8. Fully expanded, dark green leaves of about two month old plants are used for bombardment.

Leaves are placed abaxial side up on a Whatman No. 1 filter paper laying on the RMOP medium (Daniell, 1993) in standard petri plates (100×15 mm) for bombardment. Tungsten (1 µm) or Gold (0.6 µm) microprojectiles are coated with plasmid DNA (chloroplast vectors) and bombardments carried out with the biolistic device PDS1000/He (Bio-Rad) as described by Daniell (1997). Following bombardment, petri plates are sealed with parafilm and incubated at 24° C. under 12 h photoperiod. Two days after bombardment, leaves are chopped into small pieces of ~5 mm$^2$ in size and placed on the selection medium (RMOP containing 500 µg/ml of spectinomycin dihydrochloride) with abaxial side touching the medium in deep (100×25 mm) petri plates (~10 pieces per plate). The regenerated spectinomycin resistant shoots are chopped into small pieces (~2 mm$^2$) and subcloned into fresh deep petri plates (~5 pieces per plate) containing the same selection medium. Resistant shoots from the second culture cycle arbe transferred to the rooting medium (MSO medium supplemented with IBA. 1 mg/liter and spectinomycin dihydrochloride, 500 mg/liter). Rooted plants are transferred to soil and grown at 26° C. under continuous lighting conditions for further analysis.

Polymerase Chain Reaction: PCR is performed using DNA solated from control and transgenic plants to distinguish a) true chloroplast transformants from mutants and b) chloroplast transformants from nuclear transformants. Primers for testing the presence of the aadA gene (that confers spectinomycin resistance) in transgenic pants are landed on the aadA coding sequence and 16S rRNA gene (primers 1P&1M.). To test chloroplast integration of the insulin gene, one primer lands on the aadA gene, while another lands on the native chloroplast genome (primers 3P&3M) as shown in FIGS. 2A and 3B. No PCR product is obtained with nuclear transgenic plants using this set of primers. The primer set (2P & 2M, in FIGS. 2A and 3B) is used to test integration of the entire gene cassette without internal deletion or looping out during homologous recombination. A similar strategy has been used successfully to confirm chloroplast integration of foreign genes (Daniell et al., 1998; Kota et al, 1999; Guda et al., 1999). This screening is essential to eliminate mutants and nuclear transformants.

Total DNA from unbombarded and transgenic plants is isolated as described by Edwards et al., (1991) to conduct PCR analyses in transgenic plants. PCR reactions are performed in a total volume of 50 µl containing approximately 10 ng of template DNA and 1 ☐M of each primer in a mixture of 300 µM of each deoxynucleotide (dNTPs), 200 mM Tris (pH 8.8), 100 mM KCl, 100 mM (NH$_4$)$_2$SO$_4$, 20 mM Mg SO$_4$, 1% Triton X-100, 1 mg/ml nuclease-free BSA and 1 or 2 units of Taq Plus polymerase (Stratagene, La Jolla, Calif.). PCR is carried out in the Perkin Elmer's GeneAmp PCR system 2400, by subjecting the samples to 94° C. for 5 min and 30 cycles of 94° C. for 1 min, 55° C. for 1.5 min, 72° C. for 1.5 or 2 min followed by a 72° C. step for 7 min. PCR products are analyzed by electrophoresis on 0.8% agarose gels. Chloroplasat transgenic plants containing the proinsulin gene are then moved to second round of selection to achieve homoplasmy.

Southern Blot Analysis: Southern blots are performed to determine the copy number of the introduced foreign gene per cell as well as to test homoplasmy. There are several thousand copies of the chloroplast genome at present in each plant cell. Therefore, when foreign genes are inserted into the chloroplast genome, it is possible that some of the chloroplast genomes have foreign genes integrated while others remain as the wild type (heteroplasmy). Therefore, to ensure that only the transformed genome exists in cells of transgenic plants (homoplasmy), the selection process is continued. To confirm that the wild type genome does not exist at the end of the selection cycle, total DNA from transgenic plants should be probed with the chloroplast border (flanking) sequences (the trnI-trnA fragment FIGS. 2A and 3B). If wild type genomes are present (heteroplasmy), the native fragment size is observed along with transformed genomes. Presence of a large fragment (due to insertion of foreign genes within the flanking sequences) and the absence of the native small fragment confirms homoplasmy (Daniell et al., Kota et al., 1999; Guda et al., 1999).

The copy number of the integrated gene is determined by establishing homoplasmy form the transgenic chloroplast genome. Tobacco chloroplasts contain 500~10,000 copies of their genome per cell (Daniell et al, 1998). If only a fraction of the genomes are actually transformed, the copy number, by default, must be less than 10,000. By establishing that in the transgenics the insulin inserted transformed genome is the only one present, one can establish that the copy number is 5000~10,000 per cell. This is usually achieved by digesting the total DNA with a suitable restriction enzyme and probing with the flanking sequences that enable homologous recombination into the chloroplast genome. The native fragment present in the control should be absent in the transgenics. The absence of native fragment proves that only the transgenic chloroplast genome is present in the cell and there is no native, untransformed, chloroplast genome, without the insulin gene present. This established the homoplasmic nature of the transformants, simultaneously, thereby providing an estimate of 5000~10,000 copies of the foreign genes per cell.

Total DNA is extracted from leaves of transformed and wild type plants using the CTAB procedure outlined in Rogers and Bendich (1988). Total DNA is digested with suitable restriction enzymes, electrophoresed on 0.7% aragose gels and transferred to nylon membranes (Micron Separation Inc., Westboro, Mass.). Probes are labeled with $_{32}$P-dCTP using the random-pried procedure (Promega). Prehybridization and hybridization steps are carried out at 42° C. for 2 h and 16 h, respectively. Blots are soaked in a solution containing 2×SSC and 0.5% SDS for 5 min followed by transfer to 2×SSC and 0.1% SDS solution for 15 min at room temperature. Then, blots are incubated in hybridization bottles containing 0.1× SSC and 0.5% SDS solution for 30 min at 37° C. followed by another step at 68 C for 30 min, with gentle agitation. Finally blots are briefly rinsed in 0.1×SSC solutions, dried and exposed to X-ray film in the dark.

Northern Blot Analysis: Northern blots are performed to test the efficiency of transcription of the proinsulin gene fused with CTB or polymer genes. Total RNA is isolated from 150 mg of frozen leaves by using the "Rneasy Plant Total RNA Isolation Kit" (Qaigen Inc., Chatsworth, Calif.). RNA (10-40 mg) is denatured by formaldehyde treatment, separated on a 1.2% agarose gel in the presence of formaldehyde and transferred into a nitrocellulose membrane (MSI) as described in Sambrook et al. (1989). Probe DNA (proinsulin gene coding region) is labeled by the random-primed method (Promega) with $_{32}$P-dCT isotope. The blot is prehybridized, hybridized and washed as described above for southern blot analysis. Transcript levels are quantified by the Molecular Analyst Program using th GS-700 Imaging Densitometer (Bio-Rad, Hercules, Calif.).

Polymer-insulin fusion purification, quantitation and characterization:

Because polymer insulin fusion proteins exhibit inverse temperature transition properties as shown in FIGS. 1A and B, they are purified from transgenic plants essentially following the same method for polymer purification from transgenic tobacco plants (Zhang et al., 1996). However, an additional step is introduced to take advantage of the compartmentalization of insulin polymer fusion protein within chloroplasts. Chloroplasts are first isolated from crude homogenate of leaves by a simple centrifugation step at 1500×g. This eliminates most of the cellular organelles and proteins (Daniell et al., 1986). Then, chloroplasts are burst open by resuspending them in a hypotonic buffer (osmotic shock). This is a significant advantage because there are fewer soluble proteins inside chloroplasts when compared to hundreds of soluble proteins in the cytosol. Polymer extraction buffer contains 50 mM Tris-HCl, pH 7.5, 1% 2-mecaptoethanol, 5 mM EDTA and 2 mM PMSF and 0.8 M NaCl. The homogenate is then centrifuged at 10,000 g for 10 min (4° C.), and the pellet discarded. The supernatant is incubated at 42° C. for 30 minutes and then centrifuged immediately for 3 minutes at 5,000 g (room temperature). If insulin is found to be sensitive to this temperature, $T_1$ is lowered by increasing salt concentration (McPherson et al., 1996). The pellet containing the insulin-polymer fusion protein is resuspended in the extraction buffer and incubated on ice for 10 minutes. The mixture is centrifuged at 10,000 g for 10 minute (4° C.). The supernatant is then collected and stored at −20° C. The purified polymer insulin fusion-protein is electrophoresed in a SDS-PAGE gel according to Laemml (1970) and visualized by either staining with 0.3 M $CuCl_2$ (Lee et al., 1987) or transferred to nitrocellulose membrane and probed with antiserum raised against the polymer or insulin protein as described below. Quantification of purified polymer proteins may then be carried out by densitometry.

Because polymer insulin fusion proteins exhibit inverse temperature transition properties as shown in FIGS. 12 and 13, they may be purified from transgenic plants essentially following the same method described for polymer purification from transgenic tobacco plants (Zhang et al., 1996). Polymer extraction buffer contains 50 mM Tris-HCl, pH, 7.5, 1% 2 mecaptoethanol, 5 mM EDTA and 2 mM PMSF and 0.8 M NaCl. The homogenate is then centrifuged at 10,000 g for 10 minutes (4° C.), and the pellet is discarded. The supernatant is incubated at 42° C. for 30 minute and then centrifuged immediately for 3 minutes at 5,000 g (room temperature). If insulin is found to be sensitive to this temperature, $T_t$ is lowered by increasing salt concentration (McPherson et al., 1996). The pellet containing the insulin-polymer fusion protein is resuspended in the extraction buffer and incubated on ice for 10 minutes. The mixtures is centrifuged at 12,000 g for 10 minutes (4° C.). The supernatant is then collected and stored at −20° C. The purified polymer insulin-fusion protein is electrophoresed in a SDS-PAGE gel according to Leammli (1970) and visualized by either staining with 0.3 M $CuCl_2$ (Lee et al. 1987) or transferred to nitrocellulose membrane and probed with antiserum raised against the polymer or insulin protein as described below. Quantification of purified polymer proteins may be carried out by ELISA in addition to densitometry.

After electrophoresis, proteins are transferred to a nitrocellulose membrane electrophoretically in 25 mM Tris, 192 mM glycine, 5% methanol (pH 8.3). The filter is blocked with 2% dry milk in Tris-buffered saline for two hours at room temperature and stained with antiserum raised against the polymer AVGVP (SEQ ID NO:9) (kindly provided by the University of Alabama at Birmingham, monoclonal facility) overnight in 2% dry milk/Tris buffered saline. The protein bands reacting to the antibodies are visualized using alkaline phosphatase-linked secondary antibody and the substrates nitroblue tetrazolium and 5-bromo-4-chloro-3-indolyl-phosphate (Bio-Rad). Alternatively, for insulin-polymer fusion proteins, a Mouse anti-human proinsulin (IgGl) monoclonal antibody is used as a primary antibody. To detect the binding of the primary antibody to the recombinant proinsulin, a Goat anti-mouse IgG Horseradish Peroxidase Labeled monoclonal antibody (HPR) is used. The substrate used for conjugation with HPR is 3,3',5,5'-Tetramethylbenzidine. All products are available for American Qualex Antibodies, San Clement, Calif. As a positive control, human recombinant proinsulin from Sigma may be used. This human recombinant proinsulin was expressed in *E. coli* by a synthetic proinsulin gene. Quantification of purified polymer fusion proteins is carried out by densitometry using Scanning Analysis software (Biosoft, Ferguson, Mo.) installed on a Macintosh LC III computer (Apple Computer, Cupertino, USA) with a 160 Mb hard disk operating on a System 7.1, connected by SCSI interface to a Relisys RELI 2412 Scanner (Relisys, Milpitas, Calif.).total proein contents is then determined by the dye-binding assay using reagents supplied in kit for Bio-Rad, with bovine serum albumin as a standard.

Characterization of CTB expression: CTB protein levels in transgenic plants are determined using quantitative ELISA assays. A standard curve is generated using known concentrations of bacterial CTB/a 96-well microtiter plate padded with 100 ml/well of bacterial CTB (concentrations in the range of 10-1000 ng) is incubated over night at 4° C. The plate is washed thrice with PBST (phosphate buffered saline containing 0.05% Tween-20) the background is blocked b incubation in 1% bovine serum albumin (BSA) in PBS (300 l/well) at 37° C. for 2 h followed by washing 3 times with PBST. The plate is incubated in a 1:8,000 dilution of rabbit anti-cholera toxin antibody (Sigma C-3062) (100 ml/well) for 2 h at 37° C., followed by washing the wells three times with PBST. The plate is incubated with a 1:80,000 dilution of the anti-rabbit IgG conjugated with alkaline phosphatase (100 ml/well) for 2 h at 37° C. and washed thrice with PBST. Then, 100 ml alkaline phosphatase substrate (sigma Fast) pnitrophenyl phosphate tablet in 5 ml of water is added and the reaction stopped with 1M NaOH (50 ml/well) when absorbencies in the mid-range of the titration reach about 2.0, or after 1 hour, whichever comes first. The plate is then read at 405 nm. These results are used to generate a standard curve from which concentrations of plant protein can be extrapolated. Thus, total soluble plant protein (concentration previously determined using the Bradford assay) in bicarbonate buffer, pH 9.6 (15 nM NaC$_{O3}$, 35 nM NaHCO$_3$) is loaded at 100 plant n1/well and the same procedure as above can be repeated. The absorbance values are used to determine the ratio of CTB protein to total soluble pant protein, using the standard curve generated previously and the Bradford assay results.

Inheritance of Introduced Foreign Genes: In initial tobacco transformants, some are allowed to self-pollinate, whereas others are used in reciprocal crosses with control tobacco (transgenics as female acceptors and pollen donors: testing for maternal inheritance). Harvested seeds (T1) are germinated on media containing spectinomycin. Achievement of homoplasmy and mode of inheritance can be classified by looking at germination results. Homoplasmy is indicated by totally green seedlings (Daniell et al., 1998) while heteroplasmy is displayed by variegated leaves (lack of pigmentation, Svab & Maliga, 1993). Lack of variation in chlorophyll pigmentation among progeny also underscores the absence of position effect, an artifact of nuclear transformation. Maternal inheritance may be demonstrated by scie transmission of introduced genes via seed generated on transgenic plants, regardless of pollen source (green seedlings on selective media). When transgenic pollen is used for pollination of control plants, resultant progeny does not contain resistance to chemical in selective media (will appear bleached; Svab and Maliga, 1993). Molecular analyses confirms transmission and expression of introduced genes, and T2 seed is generated from those confirmed plants by the analyses described above.

Comparison of Current Purification with Polymer-based Purification Methods: It is important to compare purification methods to test yield and purity of insulin produced in *E. coli* and tobacco. (60/263,668) Three methods may be compared: a standard fusion protein in *E. coli*, polymer proinsulin fusion protein in *E. coli*, and polymer proinsulin fusion in tobacco. Polymer proinsulin fusion peptide from transgenic tobacco may be purified by methodology described in section c) and Daniell (1997). *E. coli* purification is performed as follows. One liter of each pLD containing bacteria is grown in LB/ampicillin (100 μg/ml) overnight and the fusion protein, either polymer-proinsulin or the control fusion protein (Cowley and Mackin 1997), expressed. (60/185,987) One liter of pSBL containing bacteria is grown in LB/ampicillin (100 μg/ml) overnight and the fusion protein expressed. Cells are harvested by centrifugation at 5000×g for 10 min at 4° C., and the bacterial pellets resuspended in 5 ml/g (wet wt. Bacteria) of 100 mM Tris-HCl, pH 7.3. Lysozyme is added at a concentration of 1 mg/ml and placed on a rotating shaker at room temperature for 15 min. The lysate is subjected to probe sonication for two cycles of 30 s on/30 s off at 4° C. Cellular debris is removed by centrifugation at 1000×g for 5 min at 4° C. Insulin polymer fusion protein is purified by inverse temperature transition properties (Daniell et al., 1997). The supernatant is retained and centrifuged again at 27000×g for 15 min at 4° C. to pellet the inclusion bodies. The supernatant is discarded and the pellet resuspended in 1 ml/g (original wt. Bacteria) of dH$_2$O, aliquoted into microcentrifuge tubes as 1 ml fractions, and then centrifuged at 16000×g for 5 min at 4° C. The pellets are individually washed with 1 ml of 100 mM Tris-HCl, pH 8.5, 1M urea, 1-1 Triton X-100 and again washed with 100 mM Tris HCl pH 8.5, 2 M urea, 2% Trinton X-100. The pellets are resuspended in 1 ml of dH$_2$O and transferred to a pre-weighted 30 ml Corex centrifuge tube. The sample is centrifuged at 15000×g for 5 min at 4° C., and the pellet resuspended in 10 ml/g (wet wt. pellet) of 70% formic acid. Cyanogen bromide is added to a final concentration of 400 mM and the sample incubated at room temperature in the dark for 16 h. The reaction is stopped by transferring the sample to a round bottom flask and removing the solvent by rotary evaporation at 50° C. The residue is resuspended in 20 ml/g (wet wt. pellet) of dH$_2$O, shell frozen in a dry ice ethanol bath, and then lyophilized. The lyophilized protein is dissolved in 20 ml/g (wet wt. pellet) of 500 mM Tris-HCl, pH 8.2, 7 M urea. Oixdative sulfitolysis is performed by adding sodium sulfite and sodium tetrahionate to final concentrations 100 and 10 mM, respectively, and incubating at room temperature for 3 h. This reaction is ten stopped by freezing on dry ice.

Purification and folding of Human Proinsulin: The S-sulfonated material is applied to a 2 ml bed of Sephadex G-25 equilibrated in 20 mM Tris-HCl, pH 8.2, 7 M urea, and then washed with 9 vols of 7 M urea. The collected fraction is then applied to a Pharmacia Mono Q HR 5/5 column equilibrated in 20 mM Tris-HCl, pH 8.2, 7 M urea at a flow rate of 1 ml/min. A linear gradient leading to a final concentration of 0.5 M NaCl is used to elute the bound material. 2 min (ml) factions are collected during the gradient, and protein concentration in each fraction determined. Purity and molecular mass of fractions are estimated by Tricine SDS-PAGE (as shown in FIG. 2), where Tricine is used as the trailing ion to allow better resolution of peptides in the range of 1-1000 kDa. Appropriate fractions are pooled and applied to a 1.6×20 cm column of Sephadex G-25 (superfine) equilibrated in 5 mM ammonium acetate pH 6.8. The sample is collected based on UV absorbance and freeze-dried. The partially purified S-sulfonated material is resuspended in 50 mM glycine/NaOH, pH 10.5 at a final concentration of 2 mg/ml. β-mer-captoethanol is added at a ratio of 1.5 mol per mol of cysteine of S-sulfonate and the sample stirred at 4° C. in an open container for 16 h. The sample is then analyzed by reversed-phase high-performance liquid chromatography (RP-HPLC) using a Vydac C$_4$ column (2.2×150 mm) equilibrated in 4% acetonirile and 0.1% TFA. Adsorbed peptides are eluted with a linear gradient of increasing acetonitrite concentration (0.88% per min up to a maximum of 48%). The remaining refolded proinsulin are centrifuged at 16000×g to remove insoluble material, and loaded onto a semi-preparative Vydad C$_4$ column (10×250 mm). The bound material is then eluted as described above, and the proinsulin collected and lyophilized.

Analysis and characterization of insulin expressed in *E. coli* and Tobacco: The purified expressed proinsulin is subjected to matrix-assisted laser desorption-ionization-time of flight (MALDI-TCF) analysis (as described by Cowley and Mackin, 1997), using proinsulin from Eli Lilly as both an internal and external standard. A proteolytic digestion is performed using *Staphylococcus aureus* protease V8 to determine if the disulfide bridges have formed naturally inside chloroplasts or by in vitro processing. Five μg of both the expressed proinsulin and Eli Lilly's proinsulin are lyophilized and resuspended in 50 μl of 250 mM NaPO$_4$ pH 7.8. Protease V8 is added at a ratio of 1:50 (w/w) in experimental samples and no enzyme added to the controls. All samples are then incubated overnight at 37° C., the reactions stopped by freezing on dry ice, and samples stored at −20° C. until analyzed. The samples are analyzed by RP-HPLC using Vydac C$_4$ column (2.2×150 mm) equilibrated in 4% acetonitrite and 0.1% TFA. Bound material is then eluted using a linear gradient of increasing acetonitrile concentration (0.88% per min up to a maximum of 48%).

CTB-GM1 ganglioside binding assay: A GM1-ELISA assay is performed as described by Arakawa et al. (1997) to determine if the affinity of plant-derived CTB for GM1-ganglioside. The microtiter plate is coated with monosialogangliosice-GM1 (Sigma G-7641) by incubating the plate with 100 µl/well of GM1 (3.0 µg/ml) in bicarbonate buffer, pH 9.6 at 4° C. overnight. Alternatively, the wells are coated with 100 µl/well of BSA (3.0 µg/ml) as control. The plates are incubated with transformed plant total soluble protein and bacterial CTB (Sigma C-9903) in PBS (100 µl/well) overnight at 4° C. The remainder of the procedure is then identical to the ELISA described above.

Mouse feeding assays for CTB: This is performed as described by Haq et al. (1995). BALB/c mice, divided into groups of five males each, are fasted overnight before feeding them transformed edible tobacco (that tastes like spinach) expressing CTB, untransformed edible tobacco and purified bacterial CTB. Feedings are performed at weekly intervals (0, 7, 14 days) for three weeks. Animals are observed to confirm complete consumption of material. On day 20, fecal and serum samples are collected from each animal for analysis of anti-CTB antibodies. Mice are bled retro-orbitally and the samples stored at −20° C. until assayed. Fecal samples are collected and frozen overnight at −70° C., lyophilized, resuspended in 0.8 ml PBS (pH 7.2) containing 0.05% sodium azide per 15 fecal pellets, centrifuged at 1400×g for 5 min and the supernatant stored at −20° C. until assayed. Samples are then serially diluted in PBS containing 0.05% Tween-20 (PBST) and assayed for anti-CTB IgG in serum and anti-CTB IgA in fecal pellets by the ELISA method, as described earlier.

Assessment of diabetic symptoms in NOD mice: The incidence of diabetic symptoms is compared among mice fed with control nicotine free edible tobacco and those that express the CTB-proinsulin fusion protein. Four week old female NOD mile are divided into two groups, each consisting of ten mice. Each group is fed with control or transgenic edible tobacco (nicotine free) expressing the CTB-proinsulin fusion gene. The feeding dosage is determined based on the level of expression. Starting at 10 weeks of age, the mice are monitored on a biweekly basis with urinary glucose test strips (Clinistix and Diastix, Bayer) for development of diabetes. Glycosuric mice are bled from the tail vein to check for glycemia using a glucose analyzer (Accu-Check, Boehringer Mannheim). Diabetes is confirmed by hyperglycemia (>250 mg/dl) for two consecutive weeks (Ma et al., 1997).

Induction of oral tolerance: (60/263,668) Four week old female NOD mice may, for example, be purchased from Jackson Laboratory (Bar Harbor, Me.) and housed at an animal care facility. The mice are divided into three groups, each group consisting of ten mice. Each group is fed one of the following nicotine free edible tobacco: untransformed, expressing CTB, or expressing CTB-proinsulin fursion protein. Beginning at 5 weeks of age, each mouse is fed 3 g of nicotine free edible tobacco once per week until reaching 9 weeks of age (a total of five feedings).

Antibody titer: (60/263,668) At ten weeks of age, the serum and fecal material are assayed for anti-CTB and anti-proinsulin antibody isotypes using the ELISA method described above.

Assessment of diabetic symptoms in NOD mice: (60/263,668) The incidence of diabetic symptoms can be compared among mice fed with control nicotine free edible tobacco that expresses CTB and those that express the CTB-proinsulin fusion protein. Starting at 10 weeks of age, the mice are monitored on a biweekly basis with uninary glucose test strips (Clinistix and Diastix, Bayer) for development of diabetes. Glycosuric mice are bled from the tail vein to check for glycemia using a glucose analyzer (ACCU-Check, Boehringer Mannheim). Diabetes is confirmed by hyper glycemia (>250 mg/dl) for two consecutive weeks (Ma et al., 1997)

Human Serum Albumin

HSA is a monomeric globular protein and consists of a single, generally nonglycosylated, polypeptide chain of 585 amino acids (66.5 KDa and 17 disulfid bonds) with no post-translational modifications. It is composed of three structurally similar globular domains and the disulfides are positioned in repeated searies of nine loop-link-loop structures centered around eight sequential Cys-Cys pairs. HSA is initially synthesized as pre-pro-albumin by the liver and released from endoplasmatic reticulum after removal of the aminoterminal prepeptide of 18 amino acids. The pro-albumin is further processed in the Golgi complex where the other 6 aminoterminal residues of the proeptide are cleaved by a serine proteinase (12). This results in the secretion of themature polypeptide of 585 amino acids. HAS is encoded by two codominant autosomic allelic genes. HSA belongs to the multigene family of proteinase (12). This results in the secretion of the mature polypeptide of 585 amino acids. HSA is encoded by two codominant autosomic allelic genes. HSA belongs to the multigene family of proteins that include alpha-fetoprotein and human group-specific component (Gc) or vitamin D-binding family. HSA facilitates transfer of many lgand across organ circulatory interfaces such as in the liver, intestine, kidney and brain. In addition to blood plasma, serum albumin is also found in tissues. HSA accounts for about 60% of the total protein in blood serum. In the serum of human adults, the concentration of labumin is 40 mg/ml.

Medical applications of HSA: The primary function of HSA is the maintenance of colloid osmotic pressue (COP) within the blood vessels. Its abundance makes it an important determinant of the pharmacokinetic behavior of many drugs. Reduced synthesis of HSA can be due to advanced liver disease, impaired intestinal absorption of nutrients or poor nutritional intake. Increased albumin losses can be due to kidney diseases (increased glomerular permeability to macromolecules in the nephritic syndrome), intestinal diseases (protein-losing enteropathies) or exudative skin disorders (burns). Catabolic states such as chronic infections, sepsis, surgery, intestinal resection, trauma or extensive burns can also cause hypoalbuminemia. HSA is used in therapy of blood volume disorders, for example posthaemorrhagic acute hypovolaemia or extensive burns, treatment of dhydration states, and also for cirrhotic and hepatic illnesses. It is also used as an additive in perfusion liquid for extracorporeal circulation. HSA is used clinically for replacing blood volume, but also has a variety of non-therapeutic uses, including its role as a stabilizer in formulations for other therapeutic proteins. HSA is a stabilizer ofr biological materials in nature and is used for preparing biological standards and referenced materials. Furthermore, HSA is frequently used as an experimental antigen, a cell-culture constituent and a standard in clinical-chemistry tests.

Expression systems for HSA: The expression and purification of recombinant HSA from various microorganisms has been reported previously (13-17). *Saccharomyces cerevisiae* has been used to produce HSA both intracellularly, requiring denaturation and refolding prior to analysis (18), and by secretion (19). Secreted HSA was equivalent structurally, but the recombinant product had lower levels of expression (recovery) and structural heterogeneity compared to the blood derived protein (20). HSA was also expressed in *Kluyveromyces lactis*, a yeast with good secretary properties achieving 1 g/liter in fed batch cultures (21). Ohtani et al. (22) developed a HSA expression system using *Pichia patoris* and established a purification method obtaining recombinant protein with similar levels of purity and properties as the human protein. In *Bacillus subtilis*, HSA could be secreted using baterial signal peptides (15). HSA production in *E. coli* was successful but required additional in vitro processing with trypsin to yield the mature protein (14). Sijmons et al. (23) expressed HSA in transgenic potato and tobacco plants. Fusion of HSA to the plant PR-S presequence resulted in cleavage of the presequence at its natural site and secretion of correctly processed HSA, that was indistinguishable form the authentic human protein. The expression was 0.014% of the total soluble protein. However, none of these methods have been exploited commercially.

Challenges in commercial production of HSA: Albumin is currently obtained by protein fractionation from plasma and is the world's most used intravenous protein, estimated at around 500 metric tons per year. Albumin is administered by intravenous injection of solutions containing 20% of albumin. The average dosage of albumin for each patient varies between 20-40 grams/day. The consumption of albumin is around 700 kilograms per million habitants per year. In addition to the high cost, HSA has the risk of transmitting disease as with other blood-deriviative products. The price of alumin is about $3.7/g. Thus, the market of this protein approximately amounts to $2,600,000 per million people per year (0.7 billion dollars per year in USA). Because of the high cost of albumin, synthetic macromolecules (like dextrans) are used to increase plasma colloidosmotic pressure.

Commercial HSA is mainly prepared from human plasma. This source, hardly meets the requirements of the world market. The availability of human plasma is limited and careful heat treatment of the product prepared must be performed to avoid potential contamination of the product hepatitis, HIV and other viruses. The costs of HSA extaction from blood are very high. In order to meet the demands of the large albumin market with a safe product at a low cost, innovative production systems are needed. Plant biotechnology offers promise of obtaining safe and cheap proteins to be used to treat human diseases.

Interferon Alpha

Interferons (IFNs) constitute a heterogeneous family of cytokines with antiviral, antigrowth, and immunomodulatory properties (24-26). Type I IFNs are acid-stable and constitute the first line of defense against viruses, both by displaying direct antiviral effects and by interacting with the cytokine cascade and the immune system. Their function is to induce regulation of growth and differentiation of T cells. The human IFN-α family consists of at least 22 intronless genes, 9 of which are pseudogenes and 13 expressed genes (subtypes) (27). Human IFN-α genes encode proteins of 188 or 189 amino acids. The first 23 amino acids constitute a signal peptide, and the other 165 or 166 amino acids form the mature protein. IFN-α subtypes show 78-94% homology at the nucleotide level. Presence of two disulfide bonds between Cys-1:Cys-99 and Cys-29:Cys139 is conserved among all IFN-α species (28). Human IFN-α genes are expressed constitutively in organs of normal individuals (29, 30). Individual IFN-α genes are differently expressed depending on the stimulus and they show restricted cell type expression (31). Although all IFN-α subtypes bind to a common receptor (32), several reports suggest that they show quantitatively distinct patterns of antiviral, growth inhibitory and immunomodulatory activities (33). IFN-α8 and IFN-α5 seem to have the greatest antiviral activity in liver tumour cells HuH7 (33). IFN-α5 has, at least, the same antiviral activity as IFN-α2 and in vitro experiments (unpublished data in Dr. Prieto's lab). It has been shown recently that IFN-α5 is the sole IFN-α subtype expressed in normal liver tissue (34). IFN-α expression in patients with chronic hepatitis C is reduced in the liver (34) and induced in mononuclear cells (35).

Interferons are mainly known for their antiviral activities against a wide spectrum of viruses but also for their protective role against some non-viral pathogens. They are potent imunomodulators, possess direct antiproliferative activities and are cytotoxic or cytostatic for a number of different tumour cell types. IFN-α is mainly employed as a standard therapy for hairy cell leukemia, metastasizing carcinoma and AIDS-associated angiogenic tumors of mixed cellularity known as Kaposi sarcomas. It is also active against a number of other tumours and viral infections. For example, it is the current approved therapy for chronic viral hepatitis B (CHB) and C (CHC). The IFN-α subtype used for chronic viral hepatitis is IFN-α2. About 40% of patients with CHB and about 25% of patients with CHC respond to this therapy with sustained viral clearance. The usual doses of IFN-α are 5-10 MU (subcutaneous injection) three days per week for CHB and 3 MU three days per week for 12 months of CHC. Three MU of IFN-α2 represent approximately 15 μg of recombinant protein. The response rate in patients with chronic hepatitis C can be increased by combining IFN-α2 and ribavirin. This combination therapy, which considerably increases the cost of the therapy and causes some additional side effects, results in sustained biochemical and virological remission in about 40-50% of cases. Recent data suggest that pegilated interferon in weekly doses of 180 .mu.g can also increase the sustained response rate to about 40%. IFN-α5 is the only IFN-α subtype expressed in liver; this expression is reduced in patients with CHC and IFN-α6 seems to have one of the highest antiviral activity in liver tumour cells (see above). An international patent to use IFN-α5 has been filed by Prieto's group to facilitate commercial development (36).

Human interferons are currently prepared in microbial systems via recombinant DNA technology in amounts which cannot be isolated from natural sources (leukocytes, fibroblasts, lymphocytes). Different recombinant interferon-a genes have been cloned and expressed in *E. coli* (37a, b) or yeast (38) by several groups. Generally, the synthesized protein is not correctly folded due to the lack of disulfide bridges and therefore, it remains insoluble in inclusion bodies that need to be solubilized and refolded to obtain the active interferon (39, 40). One of the most efficient methods of interferon-a expression has been published recently by Babu et al. (41). In this method, *E. coli* cells transformed with interferon vectors (regulated by temperature inducible promoters) were grown in high cell density cultures; this resulted in the production of 4 g interferon-α/liter of culture. Expression resulted exclusively in the form of insoluble inclusion bodies which were solubilized under denaturing conditions, refolded and purified to near homogeneity. The yield of purified interferon-a was approximately 300 mg/l of culture. Expression in plants via the nuclear genome has not been very successful. Smirnov et al. (42) obtained transformed tobacco plants with *Agrobacterium tumefaciens* using the interferon-.quadrature.gene under 35S CaMV promoter but the expression level was very low. Eldelbaum et al. (43) showed tobacco nuclear transformation with Interferon-.quadrature. and the expression level detected was 0.000017% of fresh weight.

The number of subjects infected with hepatitis C virus (HCV) is estimated to be 120 million (5 million in Europe and 4 million in USA). Seventy per cent of the infected people have abnormal liver function and about one third of these have severe viral hepatitis or cirrhosis. It might be estimated however that there are about 10,000-15,000 cases of chronic infection with hepatitis B virus (HBV) in Europe, a slightly lower number of cases in USA. In Asia the prevalence of chronic HCV and HBV infection is very high (about 110 million of people are infected by HCV and about 150 millions are infected by HBV). In Africa HCV infection is very prevalent. Since unremitting chronic viral hepatitis leads to liver cirrhosis and eventually to liver cancer, the high prevalence of HBV and HCV infection in Asia and Africa accounts for their very high incidence of hepatocellular carcinoma. Based on these data, the need for IFN-α is large. IFN-α2 is currently produced in microorganisms by a number of companies and the price of 3 MU (15 .mu.g) of recombinant protein in the western market is about $25. Thus, the cost of one year IFN-α2 therapy is about $ 4,000 per patient. This price makes this product unavailable for most of the patients in the world suffering from chronic viral hepatitis. Clearly methods to produce less expensive recombinant proteins via plant biotechnology innovations would be crucial to make antiviral therapy widely available. Besides, if IFN-α5 is more efficient than IFN-α2, lower doses may be required.

Insulin-Like Growth Factor-I (IGF-I)

The Insulin-like Growth Factor protein, IGF-I, is an anabolic hormone with a complex maturation process. A single IGF-I gene is transcribed into several mRNAs by alternative splicing and use of different transcription initiation sites (44-46). Depending on the choice of splicing, two immature proteins are produced: IGF-IA, expressed in several tissues and IGF-IB, mostly expressed in liver (45). Both pre-proteins produce the same mature protein. A and B immature forms have different lengths and composition, as their termini are modified post-translationally by glycosylation. However, these ends are processed in the last step of maturation. Mature IGF-I protein is secreted, not glycosylated and has three disulfide bonds, 70 amino acids and a molecular weight of 7.6 kD (47-49). Physiologically, IGF-I expression is induced by growth hormone (GH). Actually, the knock out of IGF-I in mice has shown that several functions attributed originally to GH are in fact mediated by IGF-I. GH production by adenohypofisis is repressed by feed-back inhibition of IGF-I. GH induces IGF-I synthesis in different tissues, but mostly in liver, where 90% of IGF-I is produced (48). The IGF-I receptor is expressed in different tissues. It is formed by two polypeptides: alpha that interacts with IGF-I and beta involved in signal transduction and also present in the insulin receptor (50, 51). Thus, IGF-I and insulin activation are similar.

IGF-I is a potent multifunctional anabolic hormone produced in the liver upon stimulation by growth hormone (GH). In liver cirrhosis the reduction of receptors for GH in hepatocytes and the diminished synthesis of the liver parenchyma cause a progressive fall of serum IGF-I levels. Patients with liver cirrhosis have a number of systemic derangements such as muscle atrophy, osteopenia, hypogonadism, protein-calorie malnutrition which could be related to reduced levels of circulating IGF-I. Recent studies from Prieto's laboratory have demonstrated that treatments with low doses of IGF-I induce significant improvements in nutritional status (52), intestinal absorption (53-55), osteopenia (56), hypogonadism (57) and liver function (58) in rats with experimental liver cirrhosis. These data support that IGF-I deficiency plays a pathogenic role in several systemic complications occurring in liver cirrhosis. The liver can be considered as an endocrine gland synthesising a hormone such as IGF-I with important physiological functions. Thus liver cirrhosis should be viewed as a disease accompanied by a hormone deficiency syndrome for which replacement therapy with IGF-I is warranted. Clinical studies are in progress to ascertain the role of IGF-I in the management of cirrhotic patients. IGF-I is also being currently used for Laron dwarfism treatment. These patients lack liver GH receptor so IGF-I is not expressed (59). Also IGF-I, acting as a hypoglycemiant, is given together with insulin in diabetes mellitus (60, 61). Anabolic effects of IGF-I are used in osteoporosis treatment (62, 63) hypercatabolism and starvation due to burning and HIV infection (64, 65). Unpublished studies indicate that IGF-I could also be used in patients with articular degenerative disease (osteoarthritis).

The potency of IGF-I has encouraged a great number of scientists to try IGF-I expression in various microorganisms due to the small amount present in human plasma. Production of IGF-I in yeast was shown to have several disadvantages like low fermentation yields and risks of obtaining undesirable glycosylation in these molecules (66). Expression in bacteria has been the most successful approach, either as a secreted form fused to protein leader sequences (67) or fused to a solubilized affinity fusion protein (68). In addition, IGF-I has been produced as insoluble inclusion bodies fused to protective polypeptides (69). Sun-Ok Kim and Young Lee (70a) expressed IGF-I as a truncated beta-galactosidase fusion protein. The final purification yielded approximately 5 mg of IGF-I having native conformation per liter of bacterial culture. IGF-I has also been expressed in animals. Zinovieva et al. (70b) reported an expression of 0.543 mg/ml in rabbit milk.

IGF-I circulates in plasma in a fairly high concentration varying between 120-400 ng/ml. In cirrhotic patients the values of IGF-I fall to 20 ng/ml and frequently to undetectable levels. Replacement therapy with IGF-I in liver cirrhosis requires administration of 1.5-2 mg per day for each patient. Thus, every cirrhotic patient will consume about 600 mg per year. IGF-I is currently produced in bacteria (71). The high amount of recombinant protein needed for IGF-I replacement therapy in patients with liver cirrhosis will make this treatment exceedingly expensive if new methods for cheap production of recombinant proteins are not developed. Besides, as described above, IGF-I is used in treatment of dwarfism, diabetes, osteoporosis, starvation and hypercatabolism. IGF-I use in osteoarthritis is currently being investigated. Again, plant biotechnology could provide a solution to make economically feasible the application of IGF-I therapy to all these patients.

SUMMARY OF THE INVENTION

The present invention develops recombinant DNA vectors for enhanced expression of human serum albumin, insulin-like growth factor I, and interferon-α2 and 5, via chloroplast genomes of tobacco, optimizes processing and purification of pharmaceutical proteins using chloroplast vectors in E. coli, and obtains transgenic tobacco plants.

The transgenic expression of proteins or fusion proteins is characterized using molecular and biochemical methods in chloroplasts.

Existing or modified methods of purification are employed on transgenic leaves.

Mendelian or maternal inheritance of transgenic plants is analyzed.

Large scale purification of therapeutic proteins from transgenic tobacco and comparison of current purification methods in *E. coli* or yeast is performed, and natural refolding in chloroplasts is compared with existing in vitro processing methods;

Comparison/characterization (yield and purity) of therapeutic proteins produced in yeast or *E. coli* with transgenic tobacco chloroplasts is performed, as are In vitro and in vivo (pre-clinical trials) studies of protein biofunctionality.

The invention further provides transformed plants comprising a gene provided by an expression cassette, preferably by a universal vector, which codes for a variety of desired products, especially biologically active molecules like peptides (polypeptides), proteins, insulin, human serum albumin (HSA) and other molecules further described hereinafter. The plants are allowed or caused to grow, and the desired products are isolated from the transformed crop, like tobacco, maize, etc., and if desirable, harvested first and if necessary, purified. Preferably, the expression cassette codes for Serum Human Albumin (HSA) or a Serum Human Albumin (HSA) fusion protein.

Typical pharmaceutical peptides or proteins produced in transgenic plants include hepatitis B surface antigen, norwalk virus capsid protein, foot-and-mouth disease virus, human rhinovirus 14, human immunodeficiency virus, *S. mutans* surface protein, *E. coli* enterotoxin, B subunit, malarial circumsporozoite epitopes, mouse ZP3 protein epitope (vaccine); mouse catalytic antibody 6D4, mouse mAB Guy's 13, mAB B1-8, anti-phytochrome Fv protein, anti-substance P (antibody); human serum albumin (HSA), human protein C (serum protein); a-trichosanthin, ricin (cytotoxin); human epidermal growth factor (growth factor); leu-enkephalin (neuropeptide) and human acid-glucosidase (hGC) (enzyme). Many of these molecules have been expressed in tobacco, potato tubers, etc.

Of particular interest, in accordance with the present invention, is the production of human serum albumin (HSA) with the universal integration and expression vector or with any plastid expression vector. The HSA has already been produced in transgenic (nuclear) potato and tobacco plants. Sijmons et al, 1990. The aforementioned products can be produced via chloroplast transformation in accordance with the present invention.

Recombinant Human Serum Albumin in Plants. In nuclear transgenic tobacco and potato plants, recombinant human serum albumin (rHSA) that is indistinguishable from the authentic human protein has been produced (Sijmons et al., 1990). This showed the expression of a valuable protein in transgenic plants, but also that it was possible to achieve proper processing by fusion of HSA to a plant pro-sequence that resulted in cleavage and secretion of the correct protein. The chloroplast genome of a selected plant like tobacco can be readily transformed with a universal vector as described-herein and made to express HSA.

DETAILED DESCRIPTION OF THE INVENTION

Chloroplast genetic engineering: When the concept of chloroplast genetic engineering was developed (72, 73), it was possible to introduce isolated intact chloroplasts into protoplasts and regenerate transgenic plants (74). Therefore, early investigations on chloroplast transformation focused on the development of in organelle systems using intact chloroplasts capable of efficient and prolonged transcription and translation (75-77) and expression of foreign genes in isolated chloroplasts (78). However, after the discovery of the gene gun as a transformation device (79), it was possible to transform plant chloroplasts without the use of isolated plastids and protoplasts. Chloroplast genetic engineering was accomplished in several phases. Transient expression of foreign genes in plastids of dicots (80, 81) was followed by such studies in monocots (82). Unique to the chloroplast genetic engineering is the development of a foreign gene expression system using autonomously replicating chloroplast expression vectors (80). Stable integration of a selectable marker gene into the tobacco chloroplast genome (83) was also accomplished using the gene gun. However, useful genes conferring valuable traits via chloroplast genetic engineering have been demonstrated only recently. For example, plants resistant to B.t. sensitive insects were obtained by integrating the cryIAc gene into the tobacco chloroplast genome (84). Plants resistant to B.t. resistant insects (up to 40,000 fold) were obtained by hyper-expression of the cry2A gene within the tobacco chloroplast genome (85). Plants have also been genetically engineered via the chloroplast genome to confer herbicide resistance and the introduced foreign genes were maternally inherited, overcoming the problem of out-cross with weeds (86). Chloroplast genetic engineering technology is currently being applied to other useful crops (73, 87).

A remarkable feature of chloroplast genetic engineering is the observation of exceptionally large accumulation of foreign proteins in transgenic plants, as much as 46% of CRY protein in total soluble protein, even in bleached old leaves (3). Stable expression of a pharmaceutical protein in chloroplasts was first reported for GVGVP (SEQ ID NO. 20), a protein based polymer with varied medical applications (such as the prevention of post-surgical adhesions and scars, wound coverings, artificial pericardia, tissue reconstruction and programmed drug delivery (88)).

Engineering novel pathways via the chloroplast: In plant and animal cells, nuclear mRNAs are translated monocistronically. This poses a serious problem when engineering multiple genes in plants (91). Therefore, in order to express the polyhydroxybutyrate polymer or Guy's 13 antibody, single genes were first introduced into individual transgenic plants, then these plants were back-crossed to reconstitute the entire pathway or the complete protein (92, 93). Similarly, in a seven year long effort, Ye et al. (81) recently introduced a set of three genes for a short biosynthetic pathway that resulted in .beta.carotene expression in rice. In contrast, most chloroplast genes of higher plants are cotranscribed (91). Expression of polycistrons via the chloroplast genome provides a unique opportunity to express entire pathways in a single transformation event. The *Bacillus thuringiensis* (Bt) cry2Aa2 operon has recently been used as a model system to demonstrate operon expression and crystal formation via the chloroplast genome (3). Cry2Aa2 is the distal gene of a three-gene operon. The orf immediately upstream of cry2Aa2 codes for a putative chaperonin that facilitates the folding of cry2Aa2 (and other proteins) to form proteolytically stable cuboidal crystals (94).

Therefore, the cry2Aa2 bacterial operon was expressed in tobacco chloroplasts to test the resultant transgenic plants for increased expression and improved persistence of the accumulated insecticidal protein(s). Stable foreign gene integration was confirmed by PCR and Southern blot analysis in T.sub.0 and T.sub.1 transgenic plants. Cry2Aa2 operon derived protein accumulated at 45.3% of the total soluble protein in mature leaves and remained stable even in old bleached leaves (46.1%) (FIG. 4). This is the highest level of foreign gene expression ever reported in transgenic plants. Exceedingly difficult to control insects (10-day old cotton bollworm, beetarmy worm) were killed 100% after consuming transgenic leaves. Electron micrographs showed the presence of the insecticidal protein folded into cuboidal crystals similar in shape to Cry2Aa2 crystals observed in *Bacillus*

*thuringiensis* (FIG. 5). In contrast to currently marketed transgenic plants with soluble CRY proteins, folded protoxin crystals will be processed only by target insects that have alkaline gut pH; this approach should improve safety of Bt transgenic plants. Absence of insecticidal proteins in transgenic pollen eliminates toxicity to non-target insects via pollen. In addition to these environmentally friendly approaches, this observation should serve as a model system for large-scale production of foreign proteins within chloroplasts in a folded configuration enhancing their stability and facilitating single step purification. This is the first demonstration of expression of a bacterial operon in transgenic plants and opens the door to engineer novel pathways in plants in a single transformation event.

Engineering small peptides via the chloroplast genome: It is common knowledge that the medical community has been fighting a vigorous battle against drug resistant pathogenic bacteria for years. Cationic antibacterial peptides from mammals, amphibians and insects have gained more attention over the last decade (95). Key features of these cationic peptides are a net positive charge, an affinity for negatively-charged prokaryotic membrane phospholipids over neutral-charged eukaryotic membranes and the ability to form aggregates that disrupt the bacterial membrane (96).

There are three major peptides with α-helical structures, cecropin from *Hyalophora cecropia* (giant silk moth), magainins from *Xenopus laevis* (African frog) and defensins from mammalian neutrophils. Magainin and its analogues have been studied as a broad-spectrum topical agent, a systemic antibiotic; a wound-healing stimulant; and an anticancer agent (97). We have recently observed that a synthetic lytic peptide (MSI-99, 22 amino acids) can be successfully expressed in tobacco chloroplast (98). The peptide retained its lytic activity against the phytopathogenic bacteria *Pseudomonas syringae* and multidrug resistant human pathogen, *Pseudomonas aeruginosa*. The anti-microbial peptide (AMP) used in this study was an amphipathic alpha-helix molecule that has an affinity for negatively charged phospholipids commonly found in the outer-membrane of bacteria. Upon contact with these membranes, individual peptides aggregate to form pores in the membrane, resulting in bacterial lysis. Because of the concentration dependent action of the AMP, it was expressed via the chloroplast genome to accomplish high dose delivery at the point of infection. PCR products and Southern blots confirmed chloroplast integration of the foreign genes and homoplasmy. Growth and development of the transgenic plants was unaffected by hyperexpression of the AMP within chloroplasts. In vitro assays with $T_0$ and $T_1$ plants confirmed that the AMP was expressed at high levels (21.5 to 43% of the total soluble protein) and retained biological activity against *Pseudomonas syringae*, a major plant pathogen. In situ assays resulted in intense areas of necrosis around the point of infection in control leaves, while transformed leaves showed no signs of necrosis (200-800 .mu.g of AMP at the site of infection) (FIG. 6). $T_1$ in vitro assays against *Pseudomonas aeruginosa* (a multi-drug resistant human pathogen) displayed a 96% inhibition of growth (FIG. 7). These results give a new option in the battle against phytopathogenic and drug-resistant human pathogenic bacteria. Small peptides (like insulin) are degraded in most organisms. However, stability of this AMP in chloroplasts opens up this compartment for expression of hormones and other small peptides.

Expression of cholera toxin .beta. subunit oligomers as a vaccine in chloroplasts: *Vibrio cholerae*, which causes acute watery diarrhea by colonizing the small intestine and producing the enterotoxin, cholera toxin (CT). Cholera toxin is a hexameric $AB_5$ protein consisting of one toxic 27 kDa A subunit having ADP ribosyl transferase activity and a non-toxic pentamer of 11.6 kDa B subunits (CTB) that binds to the A subunit and facilitates its entry into the intestinal epithelial cells. CTB when administered orally (99) is a potent mucosal immunogen which can neutralize the toxicity of the CT holotoxin by preventing it from binding to the intestinal cells (100). This is believed to be a result of it binding to eukaryotic cell surfaces via the $G_{M1}$ gangliosides, receptors present on the intestinal epithelial surface, thus eliciting a mucosal immune response to pathogens (101) and enhancing the immune response when chemically coupled to other antigens (102-105).

Figure 8A:
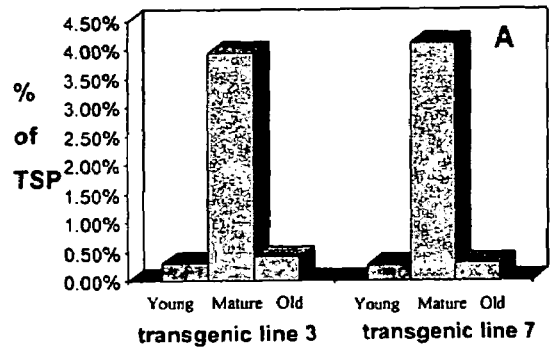
Figure 8B:
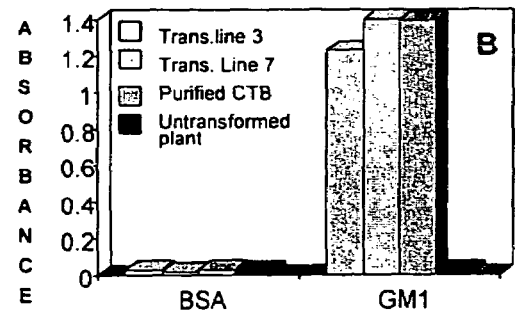
Figure 9:
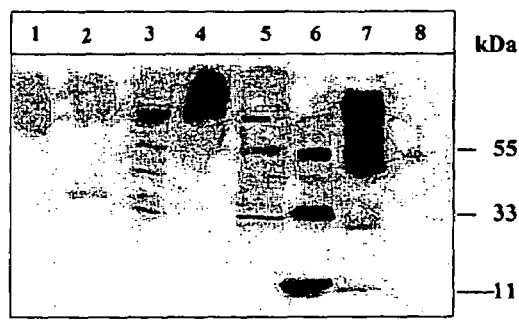

Cholera toxin (CTB) has previously been expressed in nuclear transgenic plants at levels of 0.01 (leaves) to 0.3% (tubers) of the total soluble protein. To increase expression levels, we engineered the chloroplast genome to express the CTB gene (10). We observed expression of oligomeric CTB at levels of 4-5% of total soluble plant protein (FIG. 8A). PCR and Southern Blot analyses confirmed stable integration of the CTB gene into the chloroplast genome. Western blot analysis showed that transgenic chloroplast expressed CTB was antigenically identical to commercially available purified CTB antigen (FIG. 9). Also, $G_{M1}$-ganglioside binding assays confirm that chloroplast synthesized CTB binds to the intestinal membrane receptor of cholera toxin (FIG. 8B). Transgenic tobacco plants were morphologically indistinguishable from untransformed plants and the introduced gene was found to be stably inherited in the subsequent generation as confirmed by PCR and Southern Blot analyses. The increased production of an efficient transmucosal carrier molecule and delivery system, like CTB, in chloroplasts of plants makes plant based oral vaccines and fusion proteins with CTB needing oral administration, a much more feasible approach. This also establishes unequivocally that chloroplasts are capable of forming disulfide bridges to assemble foreign proteins.

Expression and Assembly of Monoclonals in Transgenic Chloroplasts: Dental caries (cavities) is probably the most prevalent disease of humankind. Colonization of teeth by *S. mutants* is the single most important risk factor in the development of dental caries. *S. mutants* is a non-motile, gram positive coccus. It colonizes tooth surfaces and synthesizes glucans (insoluble polysaccharide) and fructans from sucrose using the enzymes glucosyltransferase and fructosyltransferase respectively (106a). The glucans play an important role by allowing the bacterium to adhere to the smooth tooth surfaces. After its adherence, the bacterium ferments sucrose and produces lactic acid. Lactic acid dissolves the minerals of the tooth, producing a cavity.

Figures 10A, 10B, 10C:
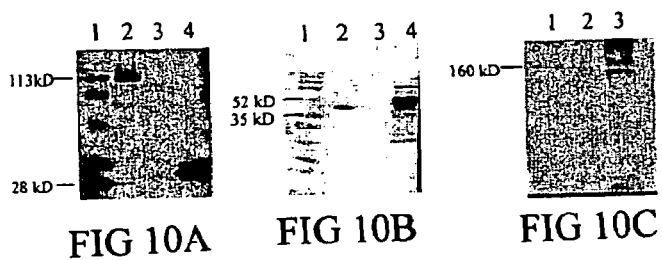

A topical monoclonal antibody therapy to prevent adherence of *S. mutants* to teeth has recently been developed. The incidence of cariogenic bacteria (in humans and animals) and dental caries (in animals) was dramatically reduced for periods of up to two years after the cessation of the antibody therapy. No adverse events were detected either in the exposed animals or in human volunteers (106b). The annual requirement for this antibody in the US alone may eventually exceed 1 metric ton. Therefore, this antibody was expressed via the chloroplast genome to achieve higher levels of expression and proper folding (11). The integration of antibody genes into the chloroplast genome was confirmed by PCR and Southern blot analysis. The expression of both heavy and light chains was confirmed by western blot analysis under reducing conditions (FIG. 10A,B). The expression of fully assembled antibody was confirmed by western blot analysis under non-reducing conditions (FIG. 10C). This is the first report of successful assembly of a multi-subunit human protein in transgenic chloroplasts. Production of monoclonal antibodies at agricultural level should reduce their cost and create new applications of monoclonal antibodies.

Human Serum Albumin

Figure 16:
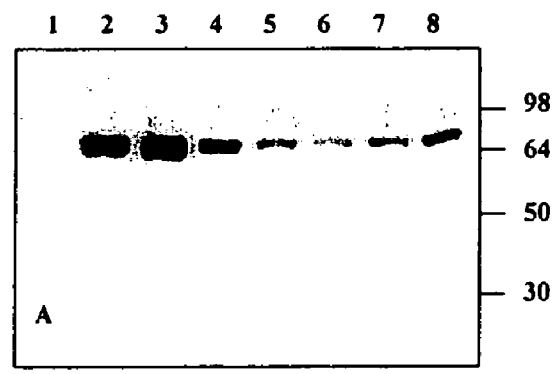
Figure 17:
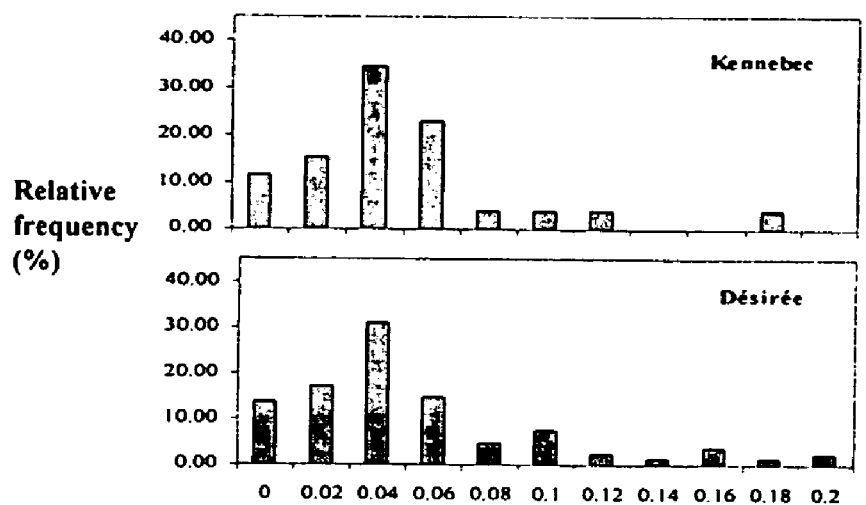
FIG. 17 is a frequency histogram including percentage Kennebec and Désirée transgenic plants expressing different HAS levels.

Nuclear Transformation: The human HSA CDNA was cloned from human liver cells and the patatin promoter (whose expression is tuber specific (107)) fused along with the leader sequence of PIN II (proteinase II inhibitor potato transit peptide that directs HSA to the apoplast (108)). Leaf discs of Desiree and Kennebec potato plants were transformed using *Agrobacterium tumefaciens*. A total of 98 transgenic Desiree clones and 30 Kennebec clones were tested by PCR and western blots. Western blots showed that the recombinant albumin (rHSA) had been properly cleaved by the proteinase 11 inhibitor transit peptide (FIG. 16). Expression levels of both cultivars were very different among all transgenic clones as expected (FIG. 17), probably because of position effects and gene silencing (89,90). The population distribution was similar in both cultivars: majority of transgenic clones showed expression levels between 0.04 and 0.06% of rHSA in the total soluble protein. The maximum recombinant HSA amount expressed was 0.2%. Between one and five T-DNA insertions per tetraploid genome were observed in these clones. Plants with higher protein expression were always clones with several copies of the HSA gene. Levels of mRNA were analyzed by Northern blots. There was a correlation between transcript levels and recombinant albumin accumulation in transgenic tubers. The N-terminal sequence showed proper cleavage of the transit peptide and the amino terminal sequence between recombinant and human HSA was identical. Inhibition of patatin expression using the antisense technology did not improve the amount of rHSA. Average expression level among 29 transgenic plants was 0.032% of total soluble protein, with a maximum expression of 0.1%.

Transformation of the tobacco chloroplast genome was initiated for hyperexpression of HSA. The codon composition is ideal for chloroplast expression and no changes in nucleotide sequences were necessary. For all the constructs pLD vector was used. Several vectors were designed to optimize HSA expression. All these contained ATG as the first amino acid of the mature protein.

RBS-ATG-HSA The first vector included the gene that codes for the mature HSA plus an additional ATG as a translation initiation codon. We included the ATG in one of the primers of the PCR, 5 nucleotides downstream of the chloroplast preferred RBS sequence GGAGG. The cDNA sequence of the mature HSA (cloned in Dr. Mingo-Castel's laboratory) was used as a template. The PCR product was cloned into PCR 2.1 vector, excised as an EcoRI-NotI fragment and introduced into the pLD vector. (Update "Human Therapeutic Proteins") The vector includes the chloroplast preferred Ribosome Binding Site (RBS) sequence GGAGG.

5'UTRpsbA-ATG-HSA: The 200 bp tobacco chloroplast DNA fragment containing the 5' psbA UTR was amplified using PCR and tobacco DNA as template. The fragment was cloned into PCR 2.1 vector, excised EcoRI-Ncol fragment was inserted at the Ncol site of the ATG-HSA and finally inserted into the pLD vector as an EcoRI-NotI fragment downstream of the 16S rRNA promoter to enhance translation of the protein. (Update "Human Therapeutic Proteins") HSA was cloned downstream of the psbA 5' UTR including the promoter and untranslated region, which has been shown to enhance translation.

BtORF1+2-ATG-HSA: ORF 1 and ORF2 of the Bt Cry2Aa2 operon were amplified in a PCR using the complete operon as a template. The fragment was cloned into PCR 2.1 vector, excised as an EcoRI-EcoRV fragment, inserted at EcoRV site with the ATG-HSA sequence and introduced into the pLD vector as an EcoRI-NotI fragment. The ORF1 and ORF2 were fused upstream of the ATG-HSA. (Update "Human Therapeutic Proteins") This introduced the putative chaperonin (ORF2) of the B.t. cry2Aa2 operon upstream of the HSA gene, which has been shown to fould foreign proteins and form crystals, aiding in protein stability and purification.

BtORF1+2-5'UTRpsbA-ATG-HSA: The 5'UTRpsbA was introduced in the above vector upstream of the HSA at the EcoRV-Ncol site.

Figure 18:
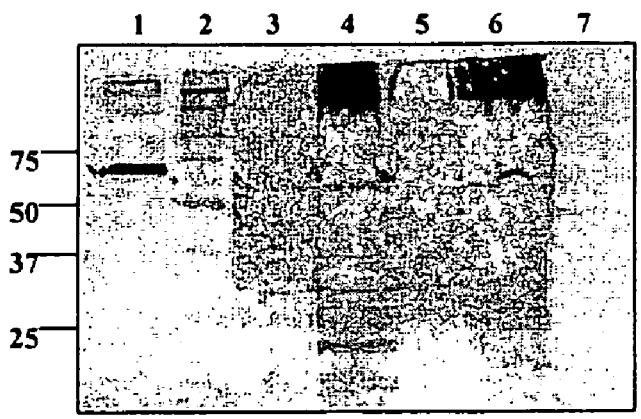
FIG. 18 is a Western Blot of HAS Expression in E. coli.
Figure 19A:
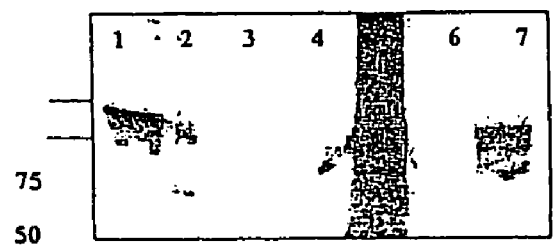
FIG. 19 shows the Western Blot of tobacco protein extracts showing expression of HSA via the chloroplast genome.
Figure 19B:
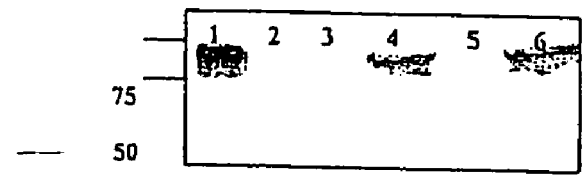
Figures 20A, 20B:
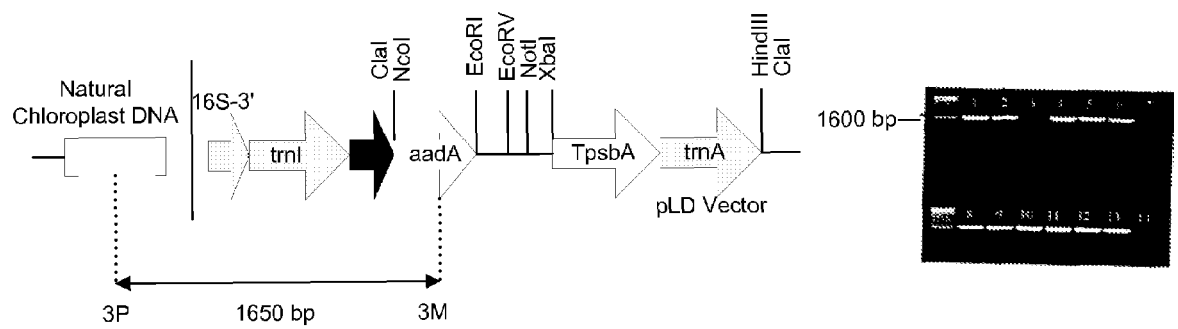
FIG. 20 shows the PCR analysis of transformants to determine integration of HSA gene into the chloroplast genome.

Because of the similarity of protein synthetic machinery (109), expression of all chloroplast vectors was first tested in *E. coli* before their use in tobacco transformation. Different levels of expression were obtained in *E. coli* depending on the construct (FIG. 18). Using the psbA 5' UTR and the ORF1 and ORF2 of the cry2Aa2 operon, we obtained higher levels of expression than using only the RBS. We have observed in previous experiments that HSA in *E. coli* is completely insoluble (as is shown in ref 14), probably due to an improper folding resulting from the absence of disulfide bonds. This is the reason why the protein is precipitated in the gel (FIG. 18). Different polypeptide sizes were observed, probably due to incomplete translation. Assuming that *E. coli* and chloroplast have similar protein synthesis machinery, one could expect different levels of expression in transgenic tobacco chloroplasts depending on the regulatory sequences, with the advantage that disulfide bonds are formed in chloroplasts (9). These three vectors were bombarded into tobacco leaves via particle bombardment (10) and after 4 weeks small shoots appeared as a result of independent transformation events. They all were tested by PCR to check integration in the chloroplast genome as shown in FIGS. 10A and B. The positive clones were transferred to pots. Transgenic leaves analyzed by western blots showed different levels of expression depending on the 5' region used in the transformation vector. Maximum levels were observed in the plants transformed with the HSA preceded by the 5' UTR of the psbA gene. Quantification of the HSA and molecular analysis of these transformants are in progress. (Update "Human Therapeutic Proteins") All chloroplast vectors were bombarded into tobacco leaves via particle bombardment and after 4 weeks shoots appeared as a result of independent transformation events. All shoots were tested by PCR to verify integration into the chloroplast genome. The positive clones were passed through a second round of selection to achieve homoplasmy and transferred to pots. The phenotype of these plants was completely normal. Transgenic leaves analyzed by western blots showed consistently the same pattern of expression depending on the 5' region used in the transformation vector (see FIG. 19). Maximum levels of expression were observed in the plants transformed with the HSA preceded by the psbA 5' UTR and promoter. Molecular characterization of the first generation is in progress. Southern blots of several clones showed homoplasmy in all transgenic lines except one (see clone #6, FIG. 8A). Northern blots showed different length of transcripts depending on the 5' regulatory region that was inserted upstream of the HSA gene (see FIG. 25). The most abundant transcript was the monocistron in plants with the 5'psbA promoter upstream of the HSA gene. Polycistrons of different length were observed based on the number of promoters used in each construct and differential processing.

We have observed different levels of HSA in ELISA depending on the extraction buffer used and further optimization of this procedure is in progress. With incomplete extraction procedures, the highest HSA level of expression in plants transformed with pLD-5'psbA-HSA was up to 11.1% of total soluble protein; this is more than 100 fold the expression observed with other two constructs (see FIG. 26). Because we have routinely observed high levels of foreign gene expression with other two vectors, we anticipate that the actual level of HSA expression in pLD-5'psbA-HSA may exceed 50% of total soluble protein. Since the expression of HSA under the 5'psbA control is light dependent, the time of the tissue harvest for expression studies is important. Such changes in HSA accumulation are currently being investigated using ELISA and Northerns.

Characterization of HSA from transgenic chloroplasts for proper folding, disulfide bond formation and functionality is in progress. The stromal pH within chloroplasts and the presence of both thioredoxin and disulfide isomerase systems provide optimal conditions for proper folding and disulfide bond formation within folded HSA.

Interferon-α5

Interferon-α5 has not been expressed yet as a commercial recombinant protein. The first attempt has been made recently. The IFN-α5 gene was cloned and the sequence of the mature protein was inserted into the pET28 vector, that included the ATG, histidine tag for purification and thrombin cleavage sequences. The tagged IFN-α5 was purified first by binding to a nickel column and biotinylated thrombin was then used to eliminate the tag on IFN-α5. Biotinylated thrombin was removed from the preparation using streptavidin agarose. The expression level was 5.6 micrograms per liter of broth culture and the recombinant protein was active in antiviral activity similar or higher than commercial IFN-α2 (Intron A, Schering Plouth).

(Update "Human Therapeutic Proteins") As proposed, we have cloned human IFNα5, fused with a Histidine tag and introduced the gene into the chloroplast transformation vector (pLD). Western blots demonstrated expression of the IFNα5 protein in *E. coli* using pLD vectors, and the maximum level was observed with the 5'psbA UTR and promoter. IFNα5 gene was cloned into the pLD using both sequences and bombarded into tobacco leaves. Shoots appeared after 5 weeks and the second round of selection is in progress.

Insulin-Like Growth Factor-I (IGF-I) Recent studies have demonstrated that treatment with low doses of IGF-I induced significant improvements in nutritional status (52), intestinal absorption (53-55), osteopenia (56), hypogonadism (57) and liver function (58) in rats with experimental liver cirrhosis. These data support that IGF-I deficiency plays a pathogenic role in several systemic complications occurring in liver cirrhosis. Clinical studies are in progress to ascertain the role of IGF-I in the management of cirrhotic patients. Unpublished studies indicate that IGF-I could also be used in patients with articular degenerative disease (osteoarthritis).

(Update "Human Therapeutic Proteins") From previous studies we observed that IGF-I gene coding sequence is not suitable for high levels of expression in chloroplasts. Therefore, we have determined the optimal chloroplast sequence and employed a recursive PCR method for total gene synthesis (see FIG. 27). The newly synthesized gene was cloned into a PCR 2.1 vector. Insertion of zz-tev sequence upstream of IGF1 coding sequence for facilitating subsequent purification is in progress.

To demonstrate expression, purification and proper cleavage of the fusion protein we also cloned the full length IGF-I (including the pre-sequence) in an alphavirus vector and expressed the protein in human cultured cells. Alphavirus system has been used because it expresses adequate amounts of protein to induce a very good immune response in test animals. We observed that the protein had the predicted size, is properly cleaved in cells to produce the mature protein and is exported into the growth medium. This secreted protein could be immunoprecipitated using anti-IGF-I antibody. The zz-tev-IGF-I was also cloned in an alphavirus vector, expressed and labeled in human cultured cells. This has allowed us to see that the protein had the predicted size and as expected, is not secreted. To cleave zz tag after purification from chloroplasts, TEV protease is necessary. Therefore, we have expressed and purified TEV protease in bacteria. After purification we could obtain approximately 0.5 mg. This TEV protease cleaved the labeled zz-tev-IGF-I producing two fragments, zz-tev and mature IGF-I. We are currently labeling more fusion protein to optimize conditions for TEV cleavage.

EXPERIMENTAL

Example 1

Evaluation of Chloroplast Gene Expression: A systematic approach is used to identify and overcome potential limitations of foreign gene expression in chloroplasts of transgenic plants. This experiment increases the utility of chloroplast transformation system by scientists interested in expressing other foreign proteins. Therefore, it is important to systematically analyze transcription, RNA abundance, RNA stability, rate of protein synthesis and degradation, proper folding and biological activity. The rate of transcription of the introduced HSA gene is compared with the highly expressing endogenous chloroplast genes (rbcL, psbA, 16S rRNA), using run on transcription assays to determine if the 16SrRNA promoter is operating as expected. The transcription efficiency of transgenic chloroplast containing each of the three constructs with different 5' regions is tested. Similarly, transgene RNA levels are monitored by northerns, dot blots and primer extension relative to endogenous rbcL, 16S rRNA or psbA. These results, along with run on transcription assays, provide valuable information of RNA stability, processing, etc. RNA appears to be extremely stable based on northern blot analysis. This systematic study is valuable to advance utility of this system by other scientists. Most importantly, the efficiency of translation is tested in isolated chloroplasts and compared with the highly translated chloroplast protein (psbA). Pulse chase experiments help assess if translational pausing, premature termination occurs. Evaluation of percent RNA loaded on polysomes or in constructs with or without 5'UTRs helps to determine the efficiency of the ribosome binding site and 5' stem-loop translational enhancers. Codon optimized genes (IGF-I, IFN) are compared with unmodified genes to investigate the rate of translation, pausing and termination. A 200-fold difference in accumulation of foreign proteins due to decreases in proteolysis conferred by a putative chaperonin (3) was observed. Therefore, proteins from constructs expressing or not expressing the putative chaperonin (with or without ORF1+2) provide valuable information on protein stability.

Example 2

Expression of the Mature Protein

HSA, Interferon and IGF-I are pre-proteins that need to be cleaved to secrete mature proteins. The codon for translation initiation is in the presequence. In chloroplasts, the necessity of expressing the mature protein forces introduction of this additional amino acid in coding sequences. In order to optimize expression levels, we first subclone the sequence of the mature proteins beginning with an ATG. Subsequent immunological assays in mice demonstrates the extra-methionine causes immunogenic response and low bioactivity. Alternatively, systems may also produce the mature protein. These systems can include the synthesis of a protein fused to a peptide that is cleaved intracellularly (processed) by chloroplast enzymes or the use of chemical or enzymatic cleavage after partial purification of proteins from plant cells.

Use of Peptides that are Cleaved in Chloroplast: Staub et al. (9) reported chloroplast expression of human somatotropin similar to the native human protein by using ubiquitin fusions that were cleaved in the stroma by an ubiquitin protease. However, the processing efficiency ranged from 30-80% and the cleavage site was not accurate. In order to process chloroplast expressed proteins a peptide which is cleaved in the stroma is essential. The transit peptide sequence of the RuBisCo (ribulose 1,5-bisphosphate carboxylase) small subunit is an ideal choice. This transit peptide has been studied in depth (111). RuBisCo is one of the proteins that is synthesized in cytoplasm and transported postranslationally into the chloroplast in an energy dependent process. The transit peptide is proteolytically removed upon transport in the stroma by the stromal processing peptidase (112). There are several sequences described for different species (113). A transit peptide consensus sequence for the RuBisCo small subunit of vascular plants is published by Keegstra et al. (114). The amino acids that are proximal to the C-terminal (41-59) are highly conserved in the higher plant transit sequences and belong to the domain which is involved in enzymatic cleavage (111). The RuBisCo small subunit transit peptide has been fused with various marker proteins (114,115), even with animal proteins (116,117), to target proteins to the chloroplast. Prior to transformation studies, the cleavage efficiency and accuracy are tested by in vitro translation of the fusion proteins and in organello import studies using intact chloroplasts. Thereafter, knowing the correct fusion sequence for producing the mature protein, such sequence encoding the amino terminal portion of tobacco chloroplast transit peptide is linked with the mature sequence of each protein. Codon composition of the tobacco RuBisCo small subunit transit peptide is compatible with chloroplast optimal translation (see section d3 and table 1 on page 30). Additional transit peptide sequences for targeting and cleavage in the chloroplast have been described (111). The lumen of thylakoids could also be a good target because thylakoids are readily purified. Lumenal proteins can be freed either by sonication or with a very low triton X100 concentration, although this requires insertion of additional amino acid sequences for efficient import (111).

Example 3

Use of Chemical or Enzymatic Cleavage: The strategy of fusing a protein to a tag with affinity for a certain ligand has been used extensively for more than a decade to enable affinity purification of recombinant products (118-120). A vast number of cleavage methods, both chemical and enzymatic, have been investigated for this purpose (120). Chemical cleavage methods have low specificity and the relatively harsh cleavage conditions can result in chemical modifications of the released products (120). Some of the enzymatic methods offer significantly higher cleavage specificities together with high efficiency, e.g. H64A subtilisin, IgA protease and factor Xa (119,120), but these enzymes have the drawback of being quite expensive.

Trypsin, which cleaves C-terminal of basic amino-acid residues, has been used for a long time to cleave fusion proteins (14,121). Despite expected low specificity, trypsin has been shown to be useful for specific cleavage of fusion proteins, leaving basic residues within folded protein domains uncleavaged (121). The use of trypsin only requires that the N-terminus of the mature protein be accessible to the protease and that the potential internal sites are protected in the native conformation. Trypsin has the additional advantage of being inexpensive and readily available. In the case of HSA, when it was expressed in *E. coli* with 6 additional codons coding for a trypsin cleavage site, HSA was processed successfully into the mature protein after treatment with the protease. In addition, the N-terminal sequence was found to be unique and identical to the sequence of natural HSA, the conversion was complete and no degradation products were observed (14). This in vitro maturation is selective because correctly folded albumin is highly resistant to trypsin cleavage at inner sites (14). This system could be tested for chloroplasts HSA vectors using protein expressed in *E. coli*.

Staub et al. (9) demonstrated that the chloroplast methionine aminopeptidase is active and they found 95% of removal of the first methionine of an ATG-somatotropin protein that was expressed via the chloroplast genome. There are several investigations that have shown a very strict pattern of cleavage by this peptidase (122). Methionine is only removed when second residues are glycine, alanine, serine, cysteine, threonine, proline or valine, but if the third amino acid is proline the cleavage is inhibited. In the expression of our three proteins we use this approach to obtain the mature protein in the case of Interferon because the penultimate aminoacid is cystein followed by aspartic acid. For HSA the second aminoacid is aspartic acid and for IGF-I glycine but it is followed by proline, so the cleavage is not dependable.

For IGF-I expression, the use of the TEV protease (Gibco cat n 10127-017) would be ideal. The cleavage site that is recognized for this protease is Glu-Asn-Leu-Tyr-Phe-Gln-Gly (SEQ ID NO. 10) and it cuts between Gln-Gly. This strategy allows the release of the mature protein by incubation with TEV protease leaving a glycine as the first amino acid consistent with human mature IGF-I protein.

The purification system of the *E. coli* Interferon-.alpha.5 expression method was based on 6 Histidine-tags that bind to a nickel column and biotinylated thrombin to eliminate the tag on IFN-α5. Thrombin recognizes Leu-Val-Pro-Arg-Gly-Ser (SEQ ID NO. 11) and cuts between Arg and Gly. This leaves two extra amino acids in the mature protein, but antiviral activity studies have shown that this protein is at least as active as commercial IFN-α2.

Example 4

Optimization of Gene Expression: Foreign genes are expressed between 3% (cry2Aα2) and 47% (cry2Aα2 operon) in transgenic chloroplasts (3,85). Based on the outcome of the evaluation of HSA chloroplast transgenic plants, several approaches can be used to enhance translation of the recombinant proteins. In chloroplasts, transcriptional regulation of gene expression is less important, although some modulations by light and developmental conditions are observed (123). RNA stability appears to be one among the least problems because of observation of excessive accumulation of foreign transcripts, at times 16,966-fold higher than the highly expressing nuclear transgenic plants (124). Chloroplast gene expression is regulated to a large extent at the post-transcriptional level. For example, 5' UTRs are necessary for optimal translation of chloroplast mRNAs. Shine-Dalgarno (GGAGG) sequences, as well as a stem-loop structure located 5' adjacent to the SD sequence, are required for efficient translation. A recent study has shown that insertion of the psbA 5' UTR downstream of the 16S rRNA promoter enhanced translation of a foreign gene (GUS) hundred-fold (125a). Therefore, the 200-bp tobacco chloroplast DNA fragment (1680-1480) containing 5' psbA UTR should be used. This PCR product is inserted downstream of the 16S rRNA promoter to enhance translation of the recombinant proteins.

Yet another approach for enhancement of translation is to optimize codon compositions. Since all the three proteins are translated in *E. coli* (see section b), it would be reasonable to expect efficient expression in chloroplasts. However, optimizing codon compositions to match the psbA gene could further enhance the level of translation. Although rbcL (RuBisCO) is the most abundant protein on earth, it is not translated as highly as the psbA gene due to the extremely high turnover of the psbA gene product. The psbA gene is under stronger selection for increased translation efficiency and is the most abundant thylakoid protein. In addition, the codon usage in higher plant chloroplasts is biased towards the NNC codon of 2-fold degenerate groups (i.e. TTC over TTT, GAC over GAT, CAC over CAT, AAC over AAT, ATC over ATT, ATA etc.). This is in addition to a strong bias towards T at third position of 4-fold degenerate groups. There is also a context effect that should be taken into consideration while modifying specific codons. The 2-fold degenerate sites immediately upstream from a GNN codon do not show this bias towards NNC. (TTT GGA is preferred to TTC GGA while TTC CGT is preferred to TTT CGT, TTC AGT to TTT AGT and TTC TCT to TTT TCT)(125b,126). In addition, highly expressed chloroplast genes use GNN more frequently that other genes. Codon composition was optimized by comparing different species. Abundance of amino acids in chloroplasts and tRNA anticodons present in chloroplast must be taken into consideration. We also compared A+T % content of all foreign genes that had been expressed in transgenic chloroplasts in our laboratory with the percentage of chloroplast expression. We found that higher levels of A+T always correlated with high expression levels (see table 1). It is also possible to modify chloroplast protease recognition sites while modifying codons, without affecting their biological functions.

The study of the sequences of HSA, IGF-I and Interferon-.quadrature.5 was done. The HSA sequence showed 57% of A+T content and 40% of the total codons matched with the psbA most translated codons. According to the data of table 1, we expected good chloroplast expression of the HSA gene without any modifications in its codon composition. IFN-.quadrature.5 has 54% of A+T content and 40% of matching with psbA codons. The composition seems to be good but this protein is small (166 amino acids) and the sequence was optimized to achieve A+T levels close to 65%. Finally, the analysis of the IGF-I sequence showed that the A+T content was 40% and only 20% of the codons are the most translated in psbA. Therefore, this gene needed to be optimized. Optimization of these two genes is done using a novel PCR approach (127,128) which has been successfully used to optimize codon composition of other human proteins.

Example 5

Vector Constructions

For all the constructs pLD vector is used. This vector was developed in this laboratory for chloroplast transformation. It contains the 16S rRNA promoter (Prrn) driving the selectable marker gene aadA (aminoglycoside adenyl transferase conferring resistance to spectinomycin) followed by the psbA 3' region (the terminator from a gene coding for photosystem II reaction center components) from the tobacco chloroplast genome. The pLD vector is a universal chloroplast expression/integration vector and can be used to transform chloroplast genomes of several other plant species (73,86) because these flanking sequences are highly conserved among higher plants. The universal vector uses trnA and trnI genes (chloroplast transfer RNAs coding for Alanine and Isoleucine) from the inverted repeat region of the tobacco chloroplast genome as flanking sequences for homologous recombination. Because the universal vector integrates foreign genes within the Inverted Repeat region of the chloroplast genome, it should double the copy number of the transgene (from 5000 to 10,000 copies per cell in tobacco). Furthermore, it has been demonstrated that homoplasmy is achieved even in the first round of selection in tobacco probably because of the presence of a chloroplast origin of replication within the flanking sequence in the universal vector (thereby providing more templates for integration). Because of these and several other reasons, foreign gene expression was shown to be much higher when the universal vector was used instead of the tobacco specific vector (88).

The following vectors are used to optimize protein expression, purification and production of proteins with the same amino acid composition as in human proteins.

a) In order to optimize expression, translation is increased using the psbA 5'UTR and optimizing the codon composition for protein expression in chloroplasts according to criteria discussed previously. The 200 bp tobacco chloroplast DNA fragment containing 5' psbA UTR is amplified by PCR using tobacco chloroplast DNA as template. This fragment is cloned directly in the pLD vector multiple cloning site (EcoRI-NcoI) downstream of the promoter and the aadA gene. The cloned sequence is exactly the same as in the psbA gene.

b) For enhancing protein stability and facilitating purification, the cry2Aa2 *Bacillus thuringiensis* operon derived putative chaperonin is used. Expression of the cry2Aa2 operon in chloroplasts provides a model system for hyper-expression of foreign proteins (46% of total soluble protein) in a folded configuration enhancing their stability and facilitating purification (3). This justifies inclusion of the putative chaperonin from the cry2Aa2 operon in one of the newly designed constructs. In this region there are two open reading frames (ORF1 and ORF2) and a ribosomal binding site (rbs). This sequence contains elements necessary for Cry2Aa2 crystallization which help to crystallize the HSA, IFG-I and IFN-α proteins aiding in the subsequent purification. Successful crystallization of other proteins using this putative chaperonin has been demonstrated (94). We amplify the ORF1 and ORF2 of the Bt Cry2Aa2 operon by PCR using the complete operon as template. The fragment is cloned into a PCR 2.1 vector and excised as an EcoRI-EcoRV product. This fragment is then cloned directly into the pLD vector multiple cloning site (EcoRI-EcoRV) downstream of the promoter and the aadA gene.

c) To obtain proteins with the same amino acid composition as mature human proteins, we first fuse all three genes (codon optimized and native sequence) with the RuBisCo small subunit transit peptide. Also other constructions are done to allow cleavage of the protein after isolation from chloroplast. These strategies also allow affinity purification of the proteins.

The first set of constructs includes the sequence of each protein beginning with an ATG, introduced by PCR using primers. Processing to get the mature protein may be performed where the ATG is shown to be a problem (determined by mice immunological assays). First, we use the RuBisCo small subunit transit peptide. This transit peptide is amplified by PCR using tobacco DNA as template and cloned into the PCR 2.1 vector. All genes are fused with the transit peptide using a MluI restriction site that is introduced in the PCR primers for amplification of the transit peptide and genes coding for three proteins. The gene fusions are inserted into the pLD vectors downstream of the 5'UTR or ORF1+2 using the restriction sites NcoI and EcoRV respectively. If use of tags or protease sequences is necessary, such sequences can be introduced by designing primers including these sequences and amplifying the gene with PCR. After completing vector constructions, all the vectors are sequenced to confirm correct nucleotide sequence and in frame fusion. DNA sequencing is done using a Perkin Elmer ABI prism 373 DNA sequencing system.

Because of the similarity of protein synthetic machinery (109), expression of all chloroplast vectors is first tested in *E. coli* before their use in tobacco transformation. For *Escherichia coli* expression XL-1 Blue strain is used. *E. coli* can be transformed by standard $CaCl_2$ transformation procedures and grown in TB culture media. Purification, biological and immunogenic assays are done using *E. coli* expressed proteins.

Example 6

Bombardment, Regeneration and Characterization of Chloroplast Transgenic Plants

Tobacco (*Nicotiana tabacum* var. Petit Havana) plants are grown aseptically by germination of seeds on MSO medium. This medium contains MS salts (4.3 g/liter), B5 vitamin mixture (myo-inositol, 100 mg/liter; thiamine-HCl, 10 mg/liter; nicotinic acid, 1 mg/liter; pyridoxine-HCl, 1 mg/liter), sucrose (30 g/liter) and phytagar (6 g/liter) at pH 5.8. Fully expanded, dark green leaves of about two month old plants are used for bombardment.

Leaves are placed abaxial side up on a Whatman No. 1 filter paper laying on the RMOP medium (79) in standard petri plates (100×15 mm) for bombardment. Gold (0.6 μm) microprojectiles are coated with plasmid DNA (chloroplast vectors) and bombardments are carried out with the biolistic device PDS1000/He (Bio-Rad) as described by Daniell (110). Following bombardment, petri plates are sealed with parafilm and incubated at 24° C. under 12 h photoperiod. Two days after bombardment, leaves are chopped into small pieces of ~5 mm² in size and placed on the selection medium (RMOP containing 500 μg/ml of spectinomycin dihydrochloride) with abaxial side touching the medium in deep (100×25 mm) petri plates (~10 pieces per plate). The regenerated spectinomycin resistant shoots are chopped into small pieces (~2 mm²) and subcloned into fresh deep petri plates (~5 pieces per plate) containing the same selection medium. Resistant shoots from the second culture cycle are then transferred to the rooting medium (MSO medium supplemented with IBA, 1 mg/liter and spectinomycin dihydrochloride, 500 mg/liter). Rooted plants are transferred to soil and grown at 26° C. under 16 hour photoperiod conditions for further analysis.

PCR Analysis of Putative Transformants

PCR is done using DNA isolated from control and transgenic plants in order to distinguish a) true chloroplast transformants from mutants and b) chloroplast transformants from nuclear transformants. Primers for testing the presence of the aadA gene (that confers spectinomycin resistance) in transgenic plants are landed on the aadA coding sequence and 16S rRNA gene. In order to test chloroplast integration of the genes, one primer lands on the aadA gene while another lands on the native chloroplast genome. No PCR product is obtained with nuclear transgenic plants using this set of primers. The primer set is used to test integration of the entire gene cassette without any internal deletion or looping out during homologous recombination. Similar strategy was used successfully to confirm chloroplast integration of foreign genes (3,85-88). This screening is essential to eliminate mutants and nuclear transformants. In order to conduct PCR analyses in transgenic plants, total DNA from unbombarded and transgenic plants is isolated as described by Edwards et al. (129). Chloroplast transgenic plants containing the desired gene are then moved to second round of selection in order to achieve homoplasmy.

Southern Analysis for Homoplasmy and Copy Number

Southern blots are done to determine the copy number of the introduced foreign gene per cell as well as to test homoplasmy. There are several thousand copies of the chloroplast genome present in each plant cell. Therefore, when foreign genes are inserted into the chloroplast genome, some of the chloroplast genomes have foreign genes integrated while others remain as the wild type (heteroplasmy). Therefore, in order to ensure that only the transformed genome exists in cells of transgenic plants (homoplasmy), the selection process is continued. In order to confirm that the wild type genome does not exist at the end of the selection process is continued. In order to confirm that the wild type genome does not exist at the end of the selection cycle, total DNA from transgenic plants are probed with the chloroplast border (flanking) sequences (the trnI-trnA fragment). When wild type genomes are present (heteroplasmy), the native fragment size is observed along with transformed genomes. Presence of a large fragment (due to insertion of foreign genes within the flanking sequences) and absence of the native small fragment confirms homoplasmy (85,86,88).

The copy number of the integrated gene is determined by establishing homoplasmy for the transgenic chloroplast genome. Tobacco chloroplasts contain 5000~10,000 copies of their genome per cell (86). If only a fraction of the genomes are actually transformed, the copy number, by default, must be less than 10,000. By establishing that in the transgenics the gene inserted transformed genome is the only one present, one can establish that the copy number is 5000~10,000 per cell. This is usually done by digesting the total DNA with a suitable restriction enzyme and probing with the flanking sequences that enable homologous recombination into the chloroplast genome. The native fragment present in the control should be absent in the transgenics. The absence of native fragment proves that only the transgenic chloroplast genome is present in the cell and there is no native, untransformed, chloroplast genome, without the foreign gene present. This establishes the homoplasmic nature of our transformants, simultaneously providing us with an estimate of 5000~10,000 copies of the foreign genes per cell.

Northern Analysis for Transcript Stability

Northern blots are done to test the efficiency of transcription of the genes. Total RNA is isolated from 150 mg of frozen leaves by using the "Rneasy Plant Total RNA Isolation Kit" (Qiagen Inc., Chatsworth, Calif.). RNA (10-40 µg) is denatured by formaldehyde treatment, separated on a 1.2% agarose gel in the presence of formaldehyde and transferred to a nitrocellulose membrane (MSI) as described in Sambrook et al. (130). Probe DNA (proinsulin gene coding region) is labeled by the random-primed method (Promega) with $^{32}$P-dCTP isotope. The blot is pre-hybridized, hybridized and washed as described above for southern blot analysis. Transcript levels are quantified by the Molecular Analyst Program using the GS-700 Imaging Densitometer (Bio-Rad, Hercules, Calif.).

Expression and Quantification of the Total Protein Expressed in Chloroplast

Chloroplast expression assays are done for each protein by Western Blot. Recombinant protein levels in transgenic plants are determined using quantitative ELISA assays. A standard curve is generated using known concentrations and serial dilutions of recombinant and native proteins. Different tissues are analyzed using young, mature and old leaves against these primary antibodies: goat anti-HAS (Nordic Immunology), anti-IGF-I and anti-Interferon alpha (Sigma). Bound IgG is measured using horseradish peroxidase-labelled anti-goat IgG.

Inheritance of Introduced Foreign Genes

While it is unlikely that introduced DNA would move from the chloroplast genome to nuclear genome, it is possible that the gene could get integrated in the nuclear genome during bombardment and remain undetected in Southern analysis. Therefore, in initial tobacco transformants, some are allowed to self-pollinate, whereas others are used in reciprocal crosses with control tobacco (transgenics as female accepters and pollen donors; testing for maternal inheritance). Harvested seeds (T1) will be germinated on media containing spectinomycin. Achievement of homoplasmy and mode of inheritance can be classified by looking at germination results. Homoplasmy is indicated by totally green seedlings (86) while heteroplasmy is displayed by variegated leaves (lack of pigmentation, 83). Lack of variation in chlorophyll pigmentation among progeny also underscores the absence of position effect, an artifact of nuclear transformation. Maternal inheritance is be demonstrated by sole transmission of introduced genes via seed generated on transgenic plants, regardless of pollen source (green seedlings on selective media). When transgenic pollen is used for pollination of control plants, resultant progeny do not contain resistance to chemical in selective media (will appear bleached; 83). Molecular analyses confirm transmission and expression of introduced genes, and T2 seed is generated from those confirmed plants by the analyses described above.

Example 7

Purification Methods

The standard method of purification employs classical biochemical techniques with the crystallized proteins inside the chloroplast. In this case, the homogenates are passed through miracloth to remove cell debris. Centrifugation at 10,000×g palletizes all foreign proteins (3). Proteins are solubilized using pH, temperature gradient, etc. This is possible if the ORF1 and 2 of the cry2Aa2 operon (see section c) can fold and crystallize the recombinant proteins as expected. Where there is no crystal formation, other purification methods must be used (classical biochemistry techniques and affinity columns with protease cleavage).

HSA: Albumin is typically administered in tens of gram quantities. At a purity level of 99.999% (a level considered sufficient for other recombinant protein preparations), recombinant HSA (rHSA) impurities on the order of one mg will still be injected into patients. So impurities from the host organism must be reduced to a minimum. Furthermore, purified rHSA must be identical to human HSA. Despite these stringent requirements, purification costs must be kept low. To purify the HSA obtained by gene manipulation, it is not appropriate to apply the conventional processes for purifying HSA originating in plasma as such. This is because the impurities to be eliminated from rHSA completely differ from those contained in the HSA originating in plasma. Namely, rHSA is contaminated with, for example, coloring matters characteristic to recombinant HSA, proteins originating in the host cells, polysaccharides, etc. In particular, it is necessary to sufficiently eliminate components originating in the host cells, since they are foreign matters for living organisms including human and can cause the problem of antigenicity.

In plants two different methods of HSA purification have been done at laboratory scale. Sijmons et al. (23) transformed potato and tobacco plants with *Agrobacterium tumefaciens*. For the extraction and purification of HSA, 1000 g of stem and leaf tissue was homogenized in 1000 ml cold PBS, 0.6% PVP, 0.1 mM PMSF and 1 mM EDTA. The homogenate was clarified by filtration, centrifuged and the supernatant incubated for 4 h with 1.5 ml polyclonal antiHSA coupled to Reactigel spheres (Pierce Chem) in the presence of 0.5% Tween 80. The complex HSA-anti HSA-Reactigel was collected and washed with 5 ml 0.5% Tween 80 in PBS. HSA was desorbed from reactigel complex with 2.5 ml of 0.1 M glycine pH 2.5, 10% dioxane, immediately followed by a buffer exchanged with Sephadex G25 to 50 mM Tris pH 8. The sample was then loaded on a HR5/5 MonoQ anion exchange column (Pharmacia) and eluted with a linear NaCl gradient (0-350 mM NaCl in 50 mM Tris ph 8 in 20 min at 1 ml/min). Fractions containing the concentrated HSA (at 290 mM NaCl) were lyophilized and applied to a HR 10/30 Sepharose 6 column (Pharmacia) in PBS at 0.3 ml/min. However, this method uses affinity columns (polyclonal anti-HSA) that are very expensive to scale-up. Also the protein is released from the column with 0.1M glycine pH 2.5 that will most probably, denature the protein. Therefore, this method can suitably modified to reduce these drawbacks.

The second method is for HSA extraction and purification from potato tubers (Dr. Mingo-Castel's laboratory). After grinding the tuber in phosphate buffer pH 7.4 (1 mg/2 ml), the homogenate is filtered in miracloth and centrifuged at 14.000 rpm 15 minutes. After this step homogenate another filtration of the supernatant in 0.45 µm filters is necessary. Then, chromatography of ionic exchange in FPLC using a DEAE Sepharose Fast Flow column (Amersham) is required. Fractions recovered are passed though an affinity column (Blue Sepharose fast flow Amersham) resulting in a product of high purity. HSA purification based on either method is acceptable.

IDF-1: All earlier attempts to produce IGF-I in *E. coli* or *Saccharomyces cerevisiae* have resulted in misfolded proteins. This has made it necessary to perform additional in vitro refolding or extensive separation techniques in order to recover the native and biological form of the molecule. In addition, IFG-I has been demonstrated to possess an intrinsic thermodynamic folding problem with regard to quantitatively folding in to a native disulfide-bonded conformation in vitro (131). Samuelsson et al. (131) and Joly et al. (132) co-expressed IGF-I with specific proteins of *E. coli* that significantly improved the relative yields of correctly folded protein and consequently facilitating purification. Samuelson et al. (132) fused the protein to affinity tags based on either the IgG-binding domain (Z) from Staphylococcal protein A or the two serum albumin domains (ABP) from Streptococcal protein G (134). The fusion protein concept allows the IGF-I molecules to be purified by IgG or HSA affinity chromatography. We also use this Z tags for protein purification including the double Z domain from *S. aureus* protein and a sequence recognized by TEV protease (see section d.2). The fusion protein is incubated with an IgG column where binding via the Z domain occurs. Z domain-IgG interaction is very specific and has high affinity, so contaminant proteins can be easily washed off the column. Incubation of the column with TEV protease elutes mature IGF-I from the column. TEV protease is produced in bacteria in large quantities fused to a 6 histidine tag that is used for TEV purification. This tag can be used to separate IGF-I from contaminant TEV protease.

IFN-α: In the *E. coli* expression method used, the purification system was based on using 6 Histidine-tags that bind to a nickel column and biotinylated thrombin to eliminate the tag on IFN-α5.

Example 8

Characterization of the Recombinant Proteins

For the safe use of recombinant proteins as a replacement in any of the current applications, these proteins must be structurally equivalent and must not contain abnormal host-derived modifications. To confirm compliance with these criteria we compare human and recombinant proteins using the currently highly sensitive and highly resolving techniques expected by the regulatory authorities to characterize recombinant products (135).

Amino Acid Analysis
Amino acid analysis to confirm the correct sequence is performed following off-line vapour phase hydrolysis using ABI 420A amino acid derivatizer with an on line 130A phenylthiocarbamyl-amino acid analyzer (Applied Biosystems/ABI). N-terminal sequence analysis is performed by Edman degradation using ABI 477A protein sequencer with an on-line 120A phenylthiohydantoin-amino acid analyzer. Automated C-terminal sequence analysis uses a Hewlett-Packard G1009A protein sequencer. To confirm the C-terminal sequence to a greater number of residues, the C-terminal tryptic peptide is isolated from tryptic digests by reverse-phase HPLC.

Protein Folding and Disulfide Bridges Formation
Western blots with reducing and non-reducing gels are done to check protein folding. PAGE to visualize small proteins will be done in the presence of tricine. Protein standards (Sigma) are loaded to compare the mobility of the recombinant proteins. PAGE is performed on PhastGels (Pharmacia Biotech). Proteins are blotted and then probed with goat anti-HSA, interferon alpha and IGF-I polyclonal antibodies. Bound IgG is detected with horseradish peroxidase-labelled anti goat IgG and visualized on X-ray film using ECL detection reagents (Amersham).

Tryptic Mapping
To confirm the presence of chloroplast expressed proteins with disulfide linkages identical to native human proteins, the samples are subjected to tryptic digestion followed by peptide mass mapping using matrix-assisted laser desorption ionization mass spectrometry (MALDI-MS). Samples are reduced with dithiothreitol, alkylated with iodoacetamide and then digested with trypsin comprising three additions of 1:100 enzyme/substrate over 48 h at 37° C. Subsequently tryptic peptides are separated by referse-phase HPLC on a Vydac C18 column.

Mass Analysis
Electrospray mass spectrometry (ESMS) is performed using a VG Quattro electrospray mass spectrometer. Samples are desalted prior to analysis by reverse-phase HPLC using an acetonitrile gradient containing trifluoroacetic acid. Spectra are measured in a nitrogen atmosphere using a Jasco J600 spectropolarimeter.

Chromatographic Techniques
For HSA, analytical gel-permeation HPLC is performed using a TSK G3000 SWxl column. Preparative gel permeation chromatography of HSA is S200 HR column. The monomer fraction, identified by absorbance at 280 nm, is dialyzed and reconcentrated to its starting concentration. For IGF-I, the reversed-phase chromatrography the SMART system (Pharmacia Biotech) is used with mPRC C2/18 SC 2.1/10 column.

Viscosity
This is a classical assay for recombinant HSA. Viscosity is a characteristic of proteins related directly to their size, shape, and conformation. The viscosities of HSA and recombinant HSA can be measured at 100 mg. Ml-1 in 0.15 M NaCl using a U-tube viscosimeter (M2 type, Poulton, Selfe and Lee Ltd. Essex, UK) at 25° C.

Glycosylation
Chloroplast proteins are not known to be glycosylated. However there are no publications to confirm or refute this assumption. Therefore glycosylation should be measured using a scaled-up version of the method of Ahmed and Further (136).

Example 9

Biological Assays

Since HSA does not have enzymatic activity, it is not possible to run biological assays. However, three different techniques can be used to check IGF-I functionally. All of them are based on the proliferation of IFG-I responding cells. First, radioactive thymidine uptake can be measured in 3T3 fibroblasts, that express IFG-I receptor, as an estimate of DNA synthesis. Also, a human megakaryoblastic cell line, HU-3, can be used. As HU-3 grows in suspension, changes in cell number and stimulation of glucose uptake induced by IGF-I are assayed using AlamarBlue or glucose consumption, respectively. AlmarBlue (Accumed International, Westlake, Ohio) is reduced by mitochondrial enzyme activity. The reduced form of the reagent is fluorescent and can be quantitatively detected, with an excitation of 530 nm and an emission of 590 nm. AlamarBlue is added to the cells for 24 hours after 2 days induction with different doses of IGF-I and in the absence of serum. Glucose consumption by HU-3 cells is then measured using a colorimetric glucose oxidase procedure provided by Signma. HU-3 cells are incubated in the absence of serum with different doses of IGF-I. Glucose is added for 8 hours and glucose concentration is then measured in the supernatant. All three methods to measure IFG-I functionally are precise, accurate and does dependent, with a linear range between 0.5 and 50 ng/ml (137).

The method to determine IFN activity is based on their anti-viral properties. This procedure measures the ability of IFN to protect HeLa cells against the cytopathic effect of encephalomyocarditis virus (EMC). This assay is performed in 96-well microtitre plate. First, HeLa cells are seeded in the wells and allowed to grow to confluency. Then, the medium is removed, replaced with medium containing IFN dilutions, and incubated for 24 hours. EMC virus is added and 24 hours later the cytopathic effect is measured. For that, the medium is removed and wells are rinsed two times with PBS and stained with methyl violet dye solution. The optical density is read at 540 nm. The values of optical density are proportional to the antiviral activity of IFN (138). Specific activity is determined with reference to standard IFN-α (code 82/576) obtained from NIBSC.

Example 10

Animal Testing and Pre-Clinical Trials

Once albumin is produced at adequate levels in tobacco and the physicochemical properties of the product correspond to those of the natural protein, toxicology studies need to be done in mice. To avoid mice response to the human protein, transgenic mice carrying HSA genomic sequences are used (139). After injection of none, 1, 10, 50 and 100 mg of purified recombinant protein, classical toxicology studies are carried out (body weigh and food intake, animal behavior, piloerection, etc). Albumin can be tested for blood volume replacement after paracentesis to eliminate the fluid from the peritoneal cavity in patients with liver cirrhosis. It has been shown that albumin infusion after this maneuver is essential to preserve effective circulatory volume and renal function (140).

IGF-I and IFN-α are tested for biological effects in vivo in animal models. Specifically, woodchucks (marmota monax) infected with the woodchuck hepatitis virus (WHV), are widely considered as the best animal model of hepatitis B virus infection (141). Preliminary studies have shown a significant increase in 5' oligoadenylate synthase RNA levels by real time polymerase chain reaction (PCR) in woodchuck peripheral blood mononuclear cells upon incubation with human IFN-α5, a proof of the biological activity of the human IFN-α5 in woodchuck cells. For in vivo studies, a total of 7 woodchucks chronically infected with WHV (WHV surface antigen and WHV-DNA positive in serum) are used: 5 animals are injected subcutaneously with 500,000 units of human IFN-α5 (the activity of human IFN-α5 is determined as described previously) three times a week for 4 months; the remaining two woodchucks are injected with placebo and used as controls. Follow-up includes weekly serological (WHV surface antigen and anti-WHV surface antibodies by ELISA) and viorological (WHV DNA in serum by real time quantitative PCR) as well as monthly immunological (T-helper responses against WHV surface and WHV core antigens measured by interleukin 2 production from PBMC incubated with those proteins) studies. Finally, basal and end of treatment liver biopsies should be performed to score liver inflammation and intrahepatic WHV-DNA levels. The final goal of treatment is decrease of viral replication by WHV-DNA in serum, with secondary end points being histological improvement and decrease in intrahepatic WHV-DNA levels.

For IFG-1, the in vivo therapeutic efficacy is tested in animals in situations of IGF-I deficiency such as liver cirrhosis in rats. Several reports (56-58) have been published showing that recombinant human IGF-I has marked beneficial effects in increasing bone and muscle mass, improving liver function and correcting hypogonadism. Briefly, the induction protocol is as follows: Liver cirrhosis is induced in rats by inhalation of carbon tetrachloride twice a week for 11 weeks, with a progressively increasing exposure time from 1 to 5 minutes per gassing session. After the 11$^{th}$ week, animals continue receiving $CCl_4$ once a week (3 minutes per inhalation) to complete 30 weeks of $CCl_4$ administration. During the whole induction period, Phenobarbital (400 mg/L) is added to drinking water. To test the therapeutic efficacy of tobacco-derived IGF-I, cirrhotic rats receive 2 μg/100 g body weight/day of this compound in two divided doses, during the last 21 days of the induction protocol (weeks 28, 29, and 30). On day 22, animals are sacrificed and liver and blood samples collected. The results are compared to those obtained in cirrhotic animals receiving placebo instead of tobacco-derived IGF-I, and to healthy control rats.

Expression of the Native Cholera Toxin B Subunit Gene as Oligomers

Bacterial antigens like the B subunit proteins, CTB and LTB, which are two chemically, structurally and immunologically similar candidate vaccine antigens of prokaryotic enterotoxins, have been expressed in plants. CTB is a candidate oral subunit vaccine for cholera that causes acute watery diarrhea by colonizing the small intestine and producing the enterotoxin, cholera toxin (CT). Cholera toxin is a hexameric $AB_5$ protein consisting of one toxic 27 kDa A subunit having ADP ribosyl transferase activity and a nontoxic pentamer of 11.6 kDa B subunits (CTB) that binds to the A subunit and facilitates its entry into the intestinal epithelial cells. CTB when administered orally is a potent mucosal immunogen, which can neutralize the toxicity of the CT holotoxin by preventing it from binding to the intestinal cells (4). This is believed to be a result of it binding to eukaryotic cell surfaces via $G_{M1}$ gangliosides, receptors present on the intestinal epithelial surface, eliciting a mucosal immune response to pathogens and enhancing the immune response when chemically coupled to other antigens (5,6).

Native CTB and LTB genes have been expressed at low levels via the plant nucleus. Since, both CTB and LTB are AT-rich compared to plant nuclear genes, low expression was probably due to a number of factors such as a aberrant mRNA splicing, mRNA instability or inefficient codon usage. To avoid these undesirable features synthetic "plant optimized" genes encoding LTB were created and expressed in potato, resulting in potato tubers expressing up to 10-20 μg of LTB per gram of fresh weight (7). However, extensive codon modification of genes is laborious, expensive and often not available due to patent restrictions. One of the consequences of these constitutively expressed high LTB levels, was the stunted growth of transgenic plants that was eventually overcome by tissue specific expression in potato tubers. The maximum amount of CTB protein detected in auxin induced, nuclear transgenic potato leaf tissues was approximately 0.3% of the total soluble leaf protein when the native CTB gene was fused to an endoplasmic reticulum retention signal, thus targeting the protein to the endoplasmic reticulum for accumulation and assembly (8).

Increased expression of levels of several proteins have been attained by expressing foreign proteins in chloroplasts of higher plans (9-11). Human somatotropin has been expressed in chloroplasts with yields of 7% of the total soluble protein (12). The accumulation levels of the Bt Cry2Aa2 operon in tobacco chloroplasts are as high as 46.1% of the total soluble plant protein (1 3). This high level of expression is attributed to the putative chaperoning, orf1 and orf2, upstream of Cry2Aa2 in the operon that may help to fold the protein into a crystalline form that is stable and resistant to proteolytic degradation. Besides the ability to express polycistrons, yet another advantage of chloroplast transformation I, is the lack of recombinant protein expression in pollen of chloroplast transgenic plants. As there is no chloroplast DNA in pollen of most crops, pollen mediated outcross of recombinant genes into the environment is minimized (10-15).

Since the transcriptional and translational machinery of plastids is prokaryotic in origin and the *N. tabaccum* chloroplast genome has 62.2% AT content, it was likely that native CTB genes would be efficiently expressed in this organelle without the need for codon modification. Also, codon comparison of the CTB gene with psbA, the major translation product of the chloroplast, showed 47% homology with the most frequent codons of the psbA gene. Highly expressed plastid genes display a codon adaptation, which is defined as a bias towards a set of codons which are complimentary to abundant tRNAs (16). Codon analysis showed that 34% of the codons of CTB are complimentary to the tRNA population in the chloroplasts in comparison with 51% of psbA codons that are complimentary to the chloroplast tRNA population.

Also, stable incorporation of the CTB gene into the precise location between the trnA and trnI genes of the chloroplast genome by homologous recombination, should eliminate the 'position effect' frequently observed in nuclear transgenic plants. This should allow uniform expression levels in different transgenic lines. Amplification of the transgene, should result in a high level of CTB gene expression since each plant cell contains up to 50,000 copies of the plastid genome (17). Another significant advantage of the production of CTB in chloroplasts, is the ability of chloroplasts to form disulfide bridges (12,18,19) which are necessary for the correct folding assembly of the CTB pentamer (20).

In this study, we report the integration of the CTB gene into the inverted repeat region of the tobacco chloroplast genome, allowing 2 copies/chloroplast genome of the CTB gene per cell, resulting in chloroplasts accumulating high levels of CTB. This eliminates the need to modify the CTB gene for optimal expression in plants.

Construction of the Chloroplast Expression Vector pLD-CTB: The leader sequence (63 bp) of the native CTB gene was deleted and a start codon was introduced at the 5' end. Primers were designed to introduce an rbs site 5 bases upstream of the start codon. The CTB PCR product was then cloned into the multiple cloning site of the pCR2. 1 vector (Invitrogen) and subsequently into the chloroplast expression vector pLD-CtV2 using suitable restriction sites. Restriction enzyme digestions of the pLD-LH-CTM vector were done to confirm the correct orientation of the inserted fragment.

Expression of the pLD-LH-CTB vector was tested in *E. coli* XL-1 Blue MRF$_{TC}$ strain before tobacco transformation. *E. coli* was transformed by standard $CaCl_2$ transformation procedures. Transformed *E. coli* (24 and 28 hrs culture in 100 ml TB with 100 μg/ml ampicillin) and untransformed *E. coli* (24 and 48 hrs culture in 100 ml TB with 12.5 μg/ml tetracycline) were centrifuged for 15 min. The pellet obtained was washed with 200 mM Tris-Cl twice, resuspended in 500 μl extraction buffer (200 mM Tris-Cl, pH 8.0, 100 mM NaCl, 10 mM EDTA, 2 mM PMSF) and sonicated. To aliquots of 100 μl transformed and untransformed sonicates [containing 50-100 μg of crude protein extract as determined by Bradford protein assay (Bio-rad)] and purified CTB (100 ng, Sigma), 2×SDS sample buffer was added. These sample mixtures were loaded on a 15% sodium SDS-PAGE gel and electrophoresed at 200 v for 45 min. in Tris-glycine buffer (25 mM Tris, 250 mM glycine, pH 8.3, 0.1% SDS). The separated protein was transferred to a nitrocellulose membrane by electroblotting at 70 v for 90 min.

Immunoblot Analysis of CTB Production in *E. coli*: Nonspecific antibody reactions were blocked by incubation of the membrane in 25 ml of 5% non-fat dry milk in TBS buffer for 2 h on a rotary shaker (40 rpm) followed by washing in TBS buffer for 5 min. The membrane was incubated for 1 h in 30 ml of a 1:5000 dilution of rabbit anti-chloera antiserum (Sigma) in TBST (TBS with 0.5% Tween-20), containing 1% non-fat dry milk, followed by washing thrice in TBST. Incubation for an hour at room temperature in 30 ml of a 1:10,000 dilution of alkaline phoshphatase conjugated mouse anti-rabbit IgG. (Sigma) in TBST, washing thrice in TBST and once with TBS was followed by incubation in the Alkaline Phosphatase Color Development Reagents, BCIP/NBT in AP color development buffer (Bio-Rad) for an hour.

Bombardment and Regeneration of Chloroplast Transgenic Plants: Fully expanded, dark green leaves of about two-month old *Nicotiana tabcum* var. Petit Havana plants were placed abaxial side up on filter papers in RMOP (21) petridish plates. Microprojectiles coated with pLD-LH-CTB DNA were bombarded into the leaves using the biolistic device PDSIOOO/He (Bio-Rad), as described by Daniell (21). Following incubation at 24° C. in the dark for two days, the bombarded leaves were cut into small (~5 $mm^2$) pieces and placed abaxial side up (5 pieces/plate) on selection medium (RMOP containing 500 mg/L spectinomycin dihydrochloride). Spectinomycin resistant shoots obtained after about 1-2 months were cut into small pieces (~2 $mm^2$) and placed on the same selection medium.

PCR Analysis: Total plant DNA from putative transgenic and untransformed plants was isolated using the DNeasy kit (Qiagen). PCR primers 3P (5AAAACCCGTCCTCAGT-TCGGATTGC-3') (SEQ ID NO. 13) and 3M (5'-CCGCGT-TGTTTCATCAAGCCTTACTG-3') (SEQ ID NO. 14) were used for PCR on putative transgenic and untransformed plant total DNA. Samples were carried though 30 cycles using the following temperature sequence: 94° C. for 1 min, 62° C. for 1.5 min and 72° C. for 2 min. Cycles were preceded by denaturation for 5 min at 94.degree. C. PCR confirmed shoots from the second selection were transferred to rooting medium (MSO medium containing 500 mg/L spectinomycin).

Southern Blot Analysis: Ten micrograms of total plant DNA (isolated using DNeasy kit) per sample were digested with BglII, separated on a 0.7% agarose gel and transferred to a nylon membrane. A 0.8 kb fragment probe, homologous to the chloroplast border sequences, was generated when vector DNA was digested with BglII and BamHI. Hybridization was performed using the Ready To Go protocol (Pharmacia). Southern blot confirmed plants were transferred to pots. On flowering, seeds obtained from $T_0$ lines were germinated on spectinomycin dihydrochloride-MSO media and $T_1$ seedlings were grown in bottles containing MSO with spectinomycin (500 mg/L) for 2 weeks. The plants were later transferred to pots.

Western Blot Analysis of Plant Protein: Transformed and untransformed leaves (100 mg) were ground in liquid nitrogen and resuspended in 500 μl of extraction buffer (200 mM Tris-Cl, pH 8.0, 100 mM NaCl, 10 mM EDTA, 2 mM PMSF). Leaf extracts (100-120 μg as determined by Lowry assay) were boiled (4 min) and unboiled in reducing sample buffer (BioRad) and electrophoresed in 12% polyacrylamide gels using the buffer system of Laemmli (22). The separated proteins were transferred to a nitrocellulose membrane by electroblotting at 85 v for 1 h. The immunoblot detection procedure was similar to that done for *E. coli* blots described above. For the chemiluminescent detection, the S. Tag™ AP Lumiblot kit (Novagen) was used.

ELISA Quantification of CTB: Different concentrations (100 µl/well) of 100 mg leaves (transformed and untransformed plants) ground with liquid nitrogen and resuspended in bicarbonate buffer, pH 9.6 (15 mM $Na_2CO_3$, 35 mM $NaHCO_3$) were bound to a 96 well polyvinyl chloride microliter plate (Costar) overnight at 4° C. The background was blocked with 1% Bovine serum albumin (BSA) in 0.01M phosphate buffered saline (PBS) for 2 h at 37° C., washed thrice with washing buffer, PBST (PBS and 0.05% Tween 20) and rabbit anti-cholera serum diluted 1:8,000 in PBST containing 0.5% BSA was added and incubated for 2 h at 37° C. The wells were washed and incubated with 1:50,000 mouse anti rabbit IgG-alkaline phosphatase conjugate in PBST containing 0.5% BSA for 2 h at 37° C. The plate was developed with Sigma Fast pNPP substrate (Sigma) for 30 minutes at room temperature and the reaction was ended by addition of 3N NaOH and plates were read at 405 nm.

Figure 21A:
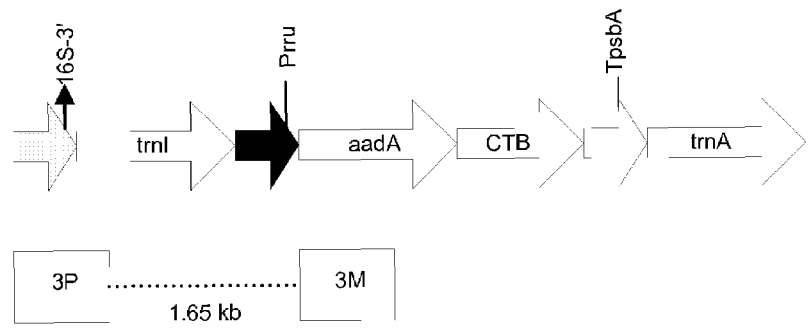
Figure 22A:
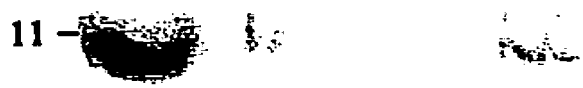
Figure 22B:
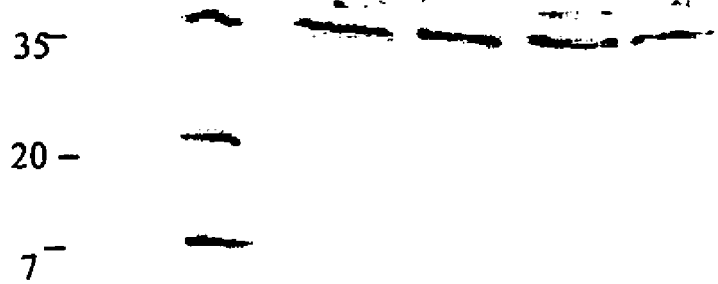

$GM_1$ Ganglioside Binding Assay: To determine the affinity of chloroplast derived CTB for $GM_1$-gangliosides, microliter plates were coated with monosialoganglioside-$GM_1$ (Sigma) (3.0 µg/ml in bicarb buffer) and incubated at 4° C. overnight. As a control, BSA (3.0 µg/ml in bicarb buffer) was coated on some wells. The wells were blocked with 1% BSA in PBS for 2 h at 37° C., washed thrice with washing buffer, PBST and incubated with dilutions of transformed plant protein, untransformed plant protein and bacterial CTB in PBS. Incubation of plates with primary and secondary antibody dilutions and detection was similar to the CTB ELISA procedure described above.

pLD-LH-CTB vector construction and *E. coli* expression: The pLD-LH-CTB vector integrates the genes of interest into the inverted repeat regions of the chloroplast genome between the trnI and trnA genes. Integration occurs through homologous recombination events between the trnI and trnA chloroplast genome as shown in FIG. 21A. The chimeric aminoglycoside 3' adenyltransferase (aadA) gene that confers resistance to spectinomycin-streptomycin and the CTB gene downstream of it are driven by the constitutive promoter of the rRNA operon (Prrn) and transcription is terminated by the psbA3' untranslated region. Since the protein synthetic machinery of chloroplasts is similar to that of *E. coli* (23), CTB expression of the pLD-LH-CTB vector in *E. coli* was tested. Western blot analysis of sonicated *E. coli* whole cell extract showed the presence of 11 kDa CTB monomers, similar to that obtained when purified commercially available CTB was treated in the same manner as shown in FIG. 22A. Oligomeric expression of CTB was not observed in *E. coli*, as expected, due to the absence of a leader peptide sequence present in the native CTB gene that directs the CTB monomer into the periplasmic space allowing for concentration and oligomeric assembly.

Selection and Regeneration of Transgenic Plants: Bombarded leaf pieces when placed on selection medium continued to grow but were bleached. Green shoots emerged from the part of the leaf in contact with the medium. Five rounds of bombardment (5 leaves each) resulted in 68 independent transformation events. Each such transgenic line was subjected to a second round of antibiotic selection. These putative transformants were subjected to PCR analysis to distinguish from nuclear transformants and mutants.

Figure 21B:
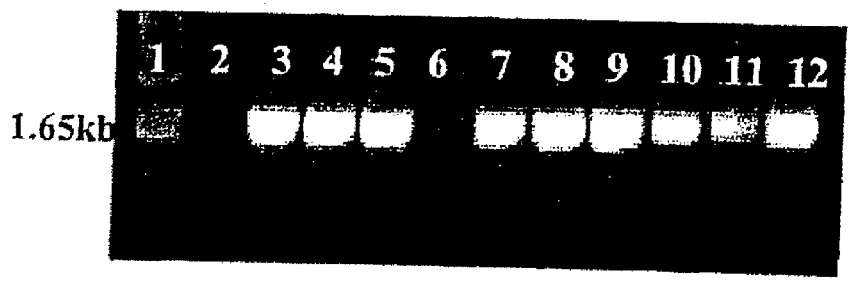

Determination of Chloroplast Integration and Homoplasmy: PCR and Southern hybridization were used to determine integration of the CTB gene into the chloroplast genome. Primers, 3P and 3M, designed to confirm incorporation of the gene cassette into the chloroplast genome were used to screen putative transgenics initially. The primer, 3P, landed on the chloroplast genome outside of the chloroplast flanking sequence used for homologous recombination as shown in FIG. 21A. The primer, 3M, landed on the aadA gene. No PCR product should be obtained if foreign genes are integrated into the nuclear genome or in mutants lacking the aadA gene. The presence of the 1.6 kb PCR product in 9 of the 10 putative transgenics screened, confirmed the site-specific integration of the gene cassette into the chloroplast genome. Database searches showed that no random priming took place as both the 3P and 3M primers showed no homology with other gene sequences. This is confirmed by the absence of PCR product in untransformed plants (FIG. 21B). Similar strategy has been used successfully by us in order to confirm chloroplast integration of foreign genes (13,14,24,25). This screening is essential to eliminate mutants and nuclear transformants and saves space and labor of maintaining hundreds of transgenic lines.

Southern blot analysis of three of the PCR positive transgenic lines was done to further confirm site specific integration and to establish copy number. In the chloroplast genome, BgIII sites flank the chloroplast border sequences 5' of 16S rRNA and 3' of the trnA region as shown in FIG. 23A. A 6.17 kb fragment from a transformed plant and a 4.47 kb fragment from an untransformed plant were obtained when total plant DNA from transformed and untransformed plants was digested with BglII. The blot of the digested products was probed with a $^{32}$P random primer-labeled 0.81 kb trnI-trnA fragment. The probe hybridized with the control giving a 4.47 kb fragment as expected, while for the transgenic lines a 6.17 kb fragment was observed, indicating that all plastid genomes had the gene cassette inserted between the tmI and trnA regions. The absence of a 4.47 kb fragment in transgenic lines indicates that homoplasmy has been achieved, to the detection level of a Southern blot. These results explain the high levels of CTB observed in transgenic tobacco plants. Southern blot confirmed plants transferred to pots were seen to have no adverse pleiotropic effects when compared to untransformed plants as shown in FIG. 4A. Southern blot analysis of $T_1$ plants in FIG. 3C shows that all 4 gransgenic lines analyzed maintained homoplasmy.

Figure 22C:

Immunoblot Analysis of Chloroplast Synthesized CTB: Antichloera toxin antibodies did not show significant cross-reaction with tobacco plant protein as can be seen in FIG. 22C, lanes 1 & 2. Boiled and unboiled leaf homogenates were run on 12% SDS PAGE gels. Unboiled chloroplast synthesized CTB protein appeared as compact 45 kDa oligomers as shown in FIG. 22C, lane 4 similar to the unboiled, pentameric bacterial CTB which appeared to have partially dissociated into tetramers, trimers and monomers upon storage at 4° C. over a period of several months from FIG. 22C, lane 7.

While heat treatment (4 min. boiling) prior to SDS PAGE of pentameric bacterial CTB, gave CTB monomers predominantly, with some protein in the dimeric and trimeric form as shown in FIG. 22C, lane 6, chloroplast synthesized CTB dissociated into dimmers and trimers only, when subjected to similar heat treatment as in FIG. 22C, lanes 3 & 5. These results are different from the heat induced dissociation of potato plant nucleus synthesized CTB; oligomers into monomers (8). A probable reason for this stability could be a more stable conformation of chloroplast synthesized CTB which may be an added advantage in storage and administration of edible vaccines. Leaf homogenates from four different transgenic plants showed almost similar expression levels of CTB protein (see FIG. 22B). This suggests very little clonal variation of CTB expression, as was confined later by ELISA quantification assays. Consistent expression levels of recombinant proteins in plants (as obtained for CTB in this research) may be essential for production of edible vaccines in plants.

ELISA Quantification of CTB Expression: Comparison of the absorbance at 405 nm of a known amount of bacterial CTB—antibody complex (linear standard curve) and that of a known concentration of transformed plant total soluble protein was used to estimate CTB expression levels. Optimal dilutions of total soluble protein from two transgenic lines were loaded in wells of the microliter plate. As reported previously (8), it was necessary to optimize the dilutions of total soluble protein, as levels of CTB protein detected varied with the concentration of total soluble protein, resulting in too high concentrations of total soluble protein inhibiting the CTB protein from binding to the wells of the plate. Both $T_0$ lines yielded CTB protein levels ranging between 3.5% to 4.1% of the total soluble protein (40 µg of chloroplast synthesized CTB protein in 1 mg of total soluble protein) as shown in FIG. 8A. Also, estimation of CTB protein expression levels from different stages of leaves—young, mature and old determined that mature leaves have the highest levels of CTB protein expression. This is in accordance with the results obtained when similar experiments were performed when the Bt Cry2aA2 gene was expressed without the putative chaperonin genes, but contrary to results with the Bt Cry2aA2 operon, which showed high expression levels in older leaves, probably due to the stable crystalline structure (13).

$GM_1$ Ganglioside ELISA Binding Assays: Both chloroplast synthesized and bacterial CTB demonstrated a strong affinity for GM1, -gangliosides (see FIG. 8B) indicating that chloroplast synthesized CTB conserved the antigenic sites necessary for binding of the CTB pentamer to the pentasaccharide $GM_1I$. The $GM_1$ binding ability also suggest proper folding of CTB molecules resulting in the pentameric structure. Since oxidation of cysteine residues in the B subunits is a prerequisite for in vivo formation of CTB pentamers (20), proper folding is a further confirmation of the ability of chloroplasts to form disulfide bonds.

High levels of expression of CTB in transgenic tobacco did not affect growth rates, flowering or seed setting as has been observed in this laboratory, unlike previously reported for the synthetic LTB gene, constitutively expressed via the nuclear genome (7). Transformed plant seedlings were green in color while untransformed seedlings lacking the aadA gene were bleached white as shown in FIG. 4B when germinated on antibiotic medium.

The potential use of this technology is three-fold. While, it can be used for large scale production of purified CTB, it can also be used as an edible vaccine if expressed in an edible plant or as a transmucosal carrier of peptides to which it is fused to, so as to either enhance mucosal immunity or to induce oral tolerance to the products of these peptides (5). Large-scale production of purified CTB in bacteria involves the use of expensive fermentation techniques and stringent purification protocols (26) making this a prohibitively expensive technology for developing countries. The cost of producing 1 kg of recombinant protein in transgenic crops has been estimated to be 50 times lower than the cost of producing the same amount by *E. coli* fermentation, assuming that recombinant protein is 20% of total *E. coli* protein (27). Thus, isolation and lysis of CTB producing chloroplasts from chloroplast transformed plants could serve as a cost-effective means of mass production of purified CTB. If used as an edible vaccine, a selection scheme eliminating the use of antibiotic resistant genes should be developed. One such scheme uses the betaine aldehyde dehydogenase (BADH) gene, which converts toxic betaine aldehyde to nontoxic glycine betaine, an osmoprotectant (28). Also, several other strategies have been proposed to eliminate antibiotic-resistant genes from transgenic plants (29.)

Transgenic potato plants that synthesize a CTB-insulin fusion protein at levels of up to 0.1% of the total soluble tuber protein have been found to show a substantial reduction in pancreatic islet inflammation and a delay in the progression of clinical diabetes (30). This may prove to be an effective clinical approach for prevention of spontaneous autoimmune diabetes. Since, increased CTB expression levels have been shown to be achievable via the chloroplast genome through this research, expression of a CTB-proinsulin fusion protein in the chloroplasts of edible tobacco (LAMD) is currently being tested in our laboratory. While existing expression levels of CTB via the chloroplast genome are adequate for commercial exploitation, levels can be increased further (about 10 fold) by insertion of a putative chaperonin, as in the case of Bt Cry2aA2 operon, (13) which likely aids in the subsequent purification of recombinant CTB due to crystallization.

Example 11

Universal Chloroplast Integration and Expression Vectors Tobacco

Exemplary universal chloroplast vectors were constructed by first cutting out the tobacco chloroplast DNA BamHI fragment (130656-140992) containing the 16S and 23S rRNA genes and subcloning it into a commonly available bacterial plasmid pUC19. A map of the tobacco chloroplast genome is shown in FIG. 35. A 2.1 kbp HindIII-EcoRI fragment present within this fragment, containing a universal border sequence comprising trnI and trnA genes (FIG. 37A), including the spacer region between the genes, was subcloned into the pUC19 plasmid at the PvuII site (FIG. 37B). The resultant plasmid was designated pSBL-Ct Bor (FIG. 37C).

The vector pSBL-RD-EPSPS (FIG. 36) contains a mutant EPSP synthase gene that codes for the enzyme EPSP synthase. Glyphosate, the active ingredient in Mosanto's ROUND UP™, binds to the protein EPSP synthase and blocks the synthesis of essential amino acids, resulting in death of a plant. The EPSP synthase coded for by the mutant gene does not bind glyphosate, and therefore confers herbicide resistance to crop plants. In a preferred embodiment of the present invention, the EPSP synthase coding region can be spliced out of vector pSBL-RD-EPSPS and replaced with the coding sequence for HSA or an HSA fusion protein.

Other genes, such as those that confer resistance to adverse environmental factors such as salt/drought tolerance (osmotolerance genes such as betaine aldehyde dehydrogenase, (BADH), for the overproduction of glycine betaine) or thermotolerance (genes coding for heat shock proteins) or cold shock tolerance proteins, or to pathogen resistance, such as antimicrobial (lytic peptides, chitinase) or antiviral (coat proteins) can be inserted singly or in non-conflicting combinations into the universal chloroplast vector, or into different cassettes of the same universal chloroplast vector to transform the target plant into one with the desired trait.

Construction of a Universal Chloroplast Integration Vector Containing a Synthetic Spacer 2 Region: A universal chloroplast vector containing only the spacer 2 region of the tobacco chloroplast genome was constructed by first subcloning a synthetic oligonucleotide comprising the spacer 2 region into the bacterial plasmid pUC19. The positive and negative strands of the 64 base pair spacer sequence were synthesized, the sequence of the positive strand was as follows: 5'GCT-GCGCCAGGGAAAAGAATAGAAGAAG-CATCTGACTACTTCATGCATGCTCCAC TTG-GCTCGG-3' The synthetic fragments were mixed and allowed to anneal, then ligated into pUC19 at the PvuII site. (FIG. 37B) Insertion of an appropriate selectable marker gene and a heterologous gene were as described above for pSBL-CtBor.

(FIG. 37C) To prepare a longer sequence which includes the tRNAile and the TRNA la genes, the same methodology is followed.

Transformation of Different Plants

Example 12

Chloroplast Transformation of Tobacco: The following example describes a classic protocol for transformation of tobacco chloroplast for which any vector can be used including a vector containing the coding sequence for HSA or an HSA fusion protein. Two such vectors are identified below. All new chloroplast vectors were first tested in tobacco as described in Daniell, (1997). Tobacco (*Nicotiana tabacum* var. Petit Havana) plants were grown aseptically by germination of seeds on MSO medium containing MS salts (4.3 g/liter), B5 vitamin mixture (myo-inositol, 100 mg/liter; thiamine-HCl, 10 mg/liter; nicotinic acid, 1 mg/liter; pyridoxine-HCl, 1 mg/liter), sucrose (30 g/liter) and phytagar (6 g/liter) at pH 5.8. Fully expanded green leaves of about two month old plants were selected for bombardment.

Leaves were placed abaxial side up on a Whatman No. 1 filter paper laying on RMOP* medium in standard Petri plates (100×15 mm) for bombardment. Tungsten (1 um) or Gold (0.6 um) microprojectiles were coated with plasmid DNA, of interest (e.g. pSBL-RD-EPSPS or pZS-RD-EPSPS) and bombardments were carried out with the biolistic device PDS1000/He (Bio-Rad) as described by Daniell, 1997. Following bombardment, petri plates were sealed with parafilm and incubated at 24° C. under 12 h photoperiod. Two days after bombardment, leaves were chopped into small pieces of about 5 mm2 in size and placed on the lethal selection medium (RMOP containing a selectable marker such as about 500 βg/ml of spectinomycin dihydrochloride) with abaxial side touching the medium in deep (100×25 mm) petri plates (about 10 pieces per plate).

Selected from the shoots that died, the regenerated spectinomycin resistant shoots were chopped into small pieces (about 2 mm2) and subcloned into fresh deep petri plates (about 5 pieces per plate) containing the same lethal selection medium. Resistant shoots from the second culture cycle were transferred to rooting medium (MSO medium supplemented with IBA, 1 4 liter and an appropriate antibiotic like 500 βg/ml of spectinomycin dihydrochloride,). Rooted plants were transferred to soil and grown at 26° C. under continuous lighting conditions for further analysis.

After transfer to the lethal selection medium, the explants gradually became pale and in about 3-8 weeks, green calli and shoots developed from the bombarded side of the leaf. Resistant shoots from each callus were considered as a clone.

PCR screening for chloroplast transformants after the first culture cycle showed that 12 out of 20 resistant clones integrate the foreign genes like the aadA gene linked to the EG121 gene into the chloroplast genome. These 12 clones were advanced to further steps of regeneration. The entire process of regeneration, starting from bombardment until transfer to soil, takes about 3-5 months.

FIG. 38 shows transformed and untransformed tobacco plastids growing in the presence of spectinomycin indicating non-lethal selection on the medium (500 yg/ml).

I claim:

1. A stable plastid transformation and expression vector competent for stably transforming a target plastid genome, wherein said vector comprises an expression cassette comprising as operably linked components, in the 5' to the 3' direction of translation, a promoter operative in a plastid, a selectable marker sequence, a heterologous DNA sequence coding for Human Serum Albumin or an Human Serum Albumin fusion protein, a transcription termination region functional in said plastid, and, flanking each side of the expression cassette, flanking DNA sequences which are homologous to a DNA sequence comprising a transcriptionally active spacer sequence of the target plastid genome, whereby stable integration of the heterologous DNA sequence into the target plastid genome is facilitated through homologous recombination of the flanking DNA sequences with the homologous sequences in the target plastid genome.

2. The vector of claim 1, wherein the heterologous DNA sequence codes for human serum albumin.

3. The vector of claim 1, wherein said spacer sequence is conserved in plastid genomes of different plant species, whereby stable intergration of the expression cassette into the target plastid genome is facilitated through homolgous recombination of the flanking sequences with the homologous sequences in the target plastid genome.

4. A stably transformed plant which comprises plastids stably transformed with the vector of claim 1.

5. The transformed plant of claim 4 which is a tobacco or alfalfa plant.

6. A stable plastid transformation and expression vector competent for stably transforming a target plastid genome, wherein said vector comprises an expression cassette comprising, as operably linked components, a heterologous DNA sequence coding for a human serum albumin protein or human serum albumin fusion protein, regulatory sequences to control the expression of said human serum albumin or human serum albumin fusion protein, and, flanking each side of the expression cassette, flanking DNA sequences which are homologous to a DNA sequence comprising a transcriptionally active spacer sequence of the target plastid genome, whereby stable integration of the heterologous DNA sequence and regulatory sequences into the plastid genome is facilitated through homologous recombination of the flanking DNA sequences with the homologous sequences-in the target plastid genome.

7. The stable vector of claim 6, wherein the regulatory sequences include a 5' UTR sequence positioned to enhance the translation of the protein.

8. A method of producing Human Serum Albumin, said method comprising:
   a. growing a plant that contains a transgenic plastid that comprises an expression cassette comprising a promoter operative in said plastid, a selectable marker sequence, a heterologous DNA sequence coding for Human Serum Albumin or an Human Serum Albumin fusion protein, and a transcription termination region functional in said plastid inserted into a transcriptionally active spacer sequence in the plastid genome of said transgenic plastid such that it expresses human serum albumin or the human serum albumin fusion protein in the plastid,
   b. harvesting the plant, and
   c. purifying the human serum albumin or human serum albumin fusion protein from said plant.

* * * * *